US006828351B2

(12) United States Patent
Epstein et al.

(10) Patent No.: US 6,828,351 B2
(45) Date of Patent: Dec. 7, 2004

(54) METHODS AND COMPOSITIONS FOR REGULATING MEMORY CONSOLIDATION

(75) Inventors: Mel Epstein, Bristol, RI (US); Kjesten A. Wiig, Providence, RI (US)

(73) Assignee: Sention, Inc., Providence, RI (US)

( * ) Notice: Subject to any disclaimer, the term of this patent is extended or adjusted under 35 U.S.C. 154(b) by 142 days.

(21) Appl. No.: 10/003,740

(22) Filed: Oct. 31, 2001

(65) Prior Publication Data

US 2002/0115725 A1 Aug. 22, 2002

Related U.S. Application Data

(60) Provisional application No. 60/245,323, filed on Nov. 1, 2000.

(51) Int. Cl.[7] ............................................. A61K 31/135
(52) U.S. Cl. ........................................................ 514/654
(58) Field of Search ................................. 514/654, 317

(56) References Cited

U.S. PATENT DOCUMENTS

| 2,828,343 | A | 3/1958 | Tindall et al. |
| 3,996,381 | A | 12/1976 | Florvall et al. |
| 4,034,113 | A | 7/1977 | Shulgin |
| 4,105,695 | A | 8/1978 | Partyka et al. |
| 4,479,932 | A | 10/1984 | Bodor |
| 4,598,094 | A | 7/1986 | Wurtman et al. |
| 4,636,494 | A | 1/1987 | Growdon et al. |
| 5,019,594 | A | 5/1991 | Wurtman et al. |
| 5,075,338 | A | 12/1991 | Knoll et al. |
| 5,096,712 | A | 3/1992 | Wurtman |
| 5,220,068 | A | 6/1993 | Knoll et al. |
| 5,422,355 | A | 6/1995 | White et al. |
| 5,684,018 | A | 11/1997 | Alexander |
| 5,914,129 | A | 6/1999 | Mauskop |
| 6,204,245 | B1 | 3/2001 | Siegel et al. |
| 6,228,875 | B1 | 5/2001 | Tsai et al. |
| 6,251,938 | B1 | 6/2001 | Chorev et al. |
| 6,284,760 | B1 | 9/2001 | Marston et al. |

FOREIGN PATENT DOCUMENTS

| FR | 2 108 032 | 5/1972 |
| GB | 2122617 A | 1/1984 |
| WO | WO 97 17067 | 5/1997 |
| WO | WO 97 26871 | 7/1997 |
| WO | WO 99 16746 | 4/1999 |
| WO | WO 00 01379 | 1/2000 |
| WO | WO 00 32556 | 6/2000 |
| WO | WO 00 59479 | 10/2000 |
| WO | WO 02 053104 A2 | 7/2002 |

OTHER PUBLICATIONS

Kuczenski, R., et al., "Hippocampus Norepinephrine, Caudate Dopamine and Serotonin, and Behavioral Responses to the Stereoisomers of Amphetamine and Methamphetamine," *J. of Neuroscience,* 15(2):1308–1317 (1995).

Smith, R.C., et al., "Comparative Effects of d–Amphetamine, 1–Amphetamine, and Methylphenidate on Mood in Man," *Psychopharmacology* 53:1–12 (1977).

Balster, R.L., et al., "A Comparison of d–Amphetamine, 1–Amphetamine, and Methamphetamine Self–administration in Rhesus Monkeys," *Pharm. Biochem. and Behavior,* 1:67–71 (1973).

(List continued on next page.)

*Primary Examiner*—Zohreh Fay
*Assistant Examiner*—Brian-Yong S. Kwon
(74) *Attorney, Agent, or Firm*—Hamilton, Brook, Smith & Reynolds, P.C.

(57) ABSTRACT

The present invention makes available methods and reagents for enhancing and/or restoring long-term memory function and performance, e.g., to improve long-term memory (LTM) and recall ability in animal subjects.

28 Claims, 11 Drawing Sheets

OTHER PUBLICATIONS

Jelic, V., et al., "Quantitative Electroencephalography in Mild Cognitive Impairment: Longitudinal Changes and Possible Prediction of Alzheimer's Disease," *Neurobiology of Aging*, 21:533–540 (2000).

Pepeu, G., "Memory Disorders: Novel Treatments, Clinical Perspective," *Life Sciences*, 55(25–26): 2189–2194 (1994).

Bartus, R.T., "Drugs to Treat Age–Related Neurodegenerative Problems," *JAGS*, 38(6):680–695 (1990).

Blaug, S.M. & Huang, W.–T. Interaction of Dextroamphetamine Sulfate with Spray–Dried Lactose. *J. Pharmaceutical Sciences* 61, 1770–1775 (Nov. 1972).

Brown, R.W. et al. D–amphetamine facilitation of Morris water task performance is blocked by eticlopride and correlated with increased dopamine synthesis in the prefrontal cortex. *Behavioural Brain Res.* 114, 135–143 (2000).

Carr, G.D. & White, N.M. The relationship betweein stereotypy and memory improvement produced by amphetamine. *Psychopharmacology* 82, 203–209 (1984).

Corsi–Cabrera, M. et al. Gender Differences in the EEG During Cognitive Activity, *Intern. J. Neurosci.* 72, 257–264 (1993).

Ebert, U. & Kirch, W. Scopolamine model of dementia: electroencephalogram findings and cognitive performance. *Euro J. Clin. Invest.* 28, 944–949 (1998).

Finkelstein, J.E. et al. Milacemide Treatment in Mice Enhances Acquisition of a Morris–Type Water Maze Task. *Pharmacol. Biochem. & Behav.* 49, 707–710 (1994).

Harris, H. et al. Behavioral Properties of Amphetaminil Enantiomers. *NCDEU Meeting*.

Jonason, K.R. et al. et al. Effects of Amphetamine Upon Relearning Pattern and Black–White Discriminations Following Neocortical Lesions in Rats. *J. Comparative & Physiological Psychology* 73, 47–55 (1970).

Kikuchi, M. et al. EEG Changes following Scopolamine Administration in Healthy Subjects. *Neuropsychobiology* 39, 219–226 (1999).

Kumar, V. & Banker, G.S. Maillard Reaction and Drug Stability. *Maillard Reactions in Chemistry, Food, and Health*. Theodore P. Labuza et al., eds. The Royal Society of Chemistry (1994).

Martinez, J.L. et al. Central and Peripheral Actions of Amphetamine on Memory Storage. *Brain Res.* 182, 157–166 (1980).

Monmaur, P. et al. Involvement of Septal Muscarinic Receptors in Cholinergically Mediated Changes in Rat Rearing Activity. *Pharmacol. Biochem. & Behav.* 58, 577–582 (1977).

Nickel, B. et al. Effect of Enantiomers of Deprenyl (Selegiline) and Amphetamine on Physical Abuse Liability and Cortical Electrical Activity in Rats. *Neuropharmacology* 29, 983–992 (1990).

Pitsikas, N. et al. DAU 6215, A Novel 5–HT3 Receptor Antagonist, Improves Performance in the Aged Rat in the Morris Water Maze Task, *Neurobiol. Aging* 14, 561–564 (1993).

Pitsikas, N. et al. Effect of Org2766, an ACTH(4–9) Analogue, on Recovery After Bilateral Transection of the Fimbria Fomix in the Rat. *Pharmacology, Biochem. & Behav.* 38, 931–934 (1991).

Ramos, J. et al. EEG Activity During Cognitive Performance in Women. *Intern. J. Neurosci.* 69, 185–195 (1993).

Riekkinen, P. Jr. Effects of Alzene and tacrine on water maze reference and working memory function in medial septal–lesioned rats. *Brain Res.* 714, 118–124 (1996).

Sainsbury, R.S. Hippocampal Theta: a Sensory–inhibition Theory of Function. *Neurosci. & Biobehav. Rev.* 22, 237–241 (1998).

Sarter, M. et al. Behavioral screening for cognition enhancers: from indiscriminate to valid testing: Part I. *Psychopharmacology* (Berl). 107, 144–59 (1992).

Sarter, M. et al. Behavioral screening for cognition enhancers: from indiscriminate to valid testing: Part II. *Psychopharmacology* (Berl). 107, 461–73 (1992).

Squire, L.R. Cerebral protein synthesis inhibition and discrimination training: effects of D–amphetamine. *Brain Res.* 177, 401–406 (1979).

Van Rijzingen, I.M.S. et al. ACTH(4–9) Analog ORG2766 Treatment 7 Months Delayed Still Improves Morris Maze Performance of Fimbria–Lesioned Rats. *Pharmacol. Biochem. & Behav.* 53, 163–169 (1996).

Yasar, S. et al. Are metabolites of 1–deprenyl (selegiline) useful or harmful? Indications from preclinical research. *J. Neural Transmission* [Suppl 48] Springer Verlag Wien, New York (1996).

Young, G.A. Relationship Between Amphetamine–Induced Effects on EEG Power Spectra and Motor Activity in Rats. *Pharmacol. Biochem. & Behav.* 30, 489–492 (1988).

Angrist & Gershon. Some Recent Studies of Amphetamine Psychosis—Unresolved Issues. 197–203.

Axelrod, J. Amphetamine: Metabolism, Physiological Disposition and its Effects on Catecholamine Storage. *Amphetamines and Related Compounds, Proceedings of the Mario Negri Institute for Pharmacological Res.*, Milan, Italy, E. Costa & S. Garattini, eds. Raven Press, N.Y. 207–216 (1970).

Axelrod, J. The Enzymatic Deamination of Amphetamine (Benzedrine). *From the Laboratory of Chemical Pharmacology, National Heart Institute, National Institutes of Health, Public Health Service, U.S. Dept. of Health, Edu. & Wellfare, Bethesda, MD*, 753–763 (Received for publication, Nov. 23, 1954).

Beckett, A.H. et al. Metabolic oxidation on aliphatic basic nitrogen atoms and their α–carbon atoms—some unifying principles. *J. Pharm. Pharmac.* 23, 809–812 (1971).

Benzeneethanamine, α–methyl–. *SciFinder Scholar* Registry Number 51–64–9, 2 (Sep. 15, 2001).

Beil, J.H. Structure–Activity Relationships of Amphetamine and Derivatives. *Amphetamines and Related Compounds Proceedings of the Mario Negri Institute for Pharmacological Res. Milan, Italy*. E. Costa & Garattini, eds. Raven Press, N.Y. 3–19 (1970).

Biel, J.H. & Bopp, B.A. Amphetamines: Structure–Activity Relationships. 1, 1–39.

Browne, R.G. & Segal, D.S. Metabolic and Experiential Factors in the Behavioral Response to Repeated Amphetamine. *Pharmacol. Biochem. Behavior* 6, 545–552 (1977).

Buresova, O. & Bures, J. Radial Maze as a Tool for Assessing the Effect of Drugs on the Working Memory of Rats. *Psychopharmacology* 77, 268–271 (1982).

Clement, B. et al. Reduction of Amphetamine Hydroxylamine and Other Aliphatic Hydroxylamines by Benzamidoxime Reductase and Human Liver Microsomes. *Chem. Res. Toxicol.* 13, 1037–1045 (2000).

Cochran, J.C. et al. Decoupling Motor Memory Strategies: Effects of Sleep Deprivation and Amphetamine. *Intern. J. Neurosci.* 74, 45–54 (1994).

Cochran, J.C. et al. Parsing Attentional Components During a Simple Reaction Time Task Using Sleep Deprivation and Amphetamine Intervention. *Perceptual and Motor Skills.*

Crabbe, J.C. & Alpern, H.P. d–Amphetamine: Disruptive Effects on the Long–Term Store of Memory and Proactive Facilitatory Effects on Learning in Inbred Mice. *Pharmacology Biochem. & Behavior* 3, 647–652 (1975).

Dalla Croce, P. et al. A Simple Procedure for N–Propenylation and N–Propynylation of Secondary Amines.

Davis, J.M. et al. Effects of Urinary pH on Amphetamine Metabolism. *Annals of N.Y. Acad. Sci.* 179, 493–501 (6 Jul. 1971).

Dring, L.G. et al. The fate of amphetamine in man and other mammals. *J. Pharm. Pharmac.* 18, 402–405 (1966).

Dring, L.G. et al. The Metabolic Fate of Amphetamine in Man and other Species. *Biochem. J.* 116, 425–435 (1970).

Fleming, K. et al. Neuropsychrological Effects of Amphetamine May Correlate with Personality Characteristics. *Psychopharmacology Bulletin* 31, 357–362 (1995).

Gelowitz, D.L. et al. Chronic L–Deprenyl or L–Amphetamine: Equal Cognitive Enhancement, Unequal MAO Inhibition. *Pharmacol. Biochem. Behav.* 47, 41–45 (1994).

Gibbs, M.E. Effects of Amphetamine on Short–Term, Protein–Independent, Memory in Day–Old Chickens. *Pharmacology Biochem. & Behavior* 4, 305–309 (1976).

Gold, P.E. et al. Modulation of Long–Term Potentiation by Peripherally Administered Amphetamine and Epinephrine. *Brain Res.* 305, 103–107 (1984).

Gunaratna, C. & Kissinger, P.T. Investigation of stereoselective metabolism of amphetamine in rat liver microsomes by microdialysis and liquid chromatography with precolumn chiral derivatization. *J. Chromatography* 828, 95–103 (1998).

Gunne, L.–M. The Urinary Ouptut of d– and l–Amphetamine in Man. *Biochemical Pharmacology* 16, 863–869 (1967).

Haycock, J.W. et al. Effects on Retention of Posttraining Amphetamine Injections in Mice: Interaction with Pretraining Experience. *Psychopharmacology* 54, 21–24 (1977).

Hutchaleelaha, A. et al. Disposition Kinetics of d– and I–Amphetamine Following Intravenous Administration of Racemic Amphetamine to Rats. *Drug Metabolism & Disposition* 22, 406–411 (1994).

Krivanek, J.A. & McGaugh Facilitating Effects of Pre– and Posttrial Amphetamine Administration on Discrimination Learning in Mice. *Agents & Actions,* 1, 36–42 (1969).

Law, M.Y.L. et al. Selective Involvement of Cytochrome P450 2D Subfamily in In Vivo 4–Hydroxylation of Amphetamine in Rat. *Drug Metabolism & Disposition* 28, 348–353 (2000).

Law, M.Y.L. & Moody, D.E. Urinary Excretion of Amphetamine and 4'–Hydroxyamphetamine by Sprague–Dawley and Dark Agouti Rats. *Life Sciences* 54, 1073–1079 (1994).

Lee, E.H.Y. & Ma, Y.L. Amphetamine Enhances Memory Retention and Facilitates Norepinephrine Release From the Hipporcampus in Rats. *Brain Res. Bulletin* 37, 411–416 (1995).

Lin, J.S. et al. Effects of amphetamine and modafinil on the sleep/wake cycle during eperimental hypersomnia induced by sleep deprivation in the cat. *J. Sleep Res.* 9, 89–96 (Mar. 2000).

Lokiec, F. et al. A Comparison of the Kinetics of d– and l–Amphetamine in the Brain of Isolated and Aggregate Rats. *Psychopharmacology* 58, 73–77 (1978).

Magidson, O.Y. & Garkusha, G.A. The synthesis of 2–phenylisopropylamine (phenamine). *Chemical Abstracts* 35, 5868 (1941).

M'Harzi, M. et al. d–Amphetamine Enhances Memory Performance in Rats with Damage to the Fimbria. *Physiology & Behavior* 42, 575–579 (1988).

Ogata, A. Constitution of ephedrine. *Chemical Abstracts* 14, 745 (1920).

PDR 946, 1221 (1969).

Penetar, D.M. et al. Amphetamine Effects on Recovery Sleep Following Total Sleep Deprivation. *Human Psychopharmacology* 6, 319–323 (1991).

Platel, A. & Porsold, R.D. Habituation of Exploratory Activity in Mice: A Screening Test for Memory Enhancing Drugs. *Psychopharmacology* 78, 346–352 (1982).

Quartermain, D. & Altman, H.J. Facilitation of retrieval by d–amphetamine following anisomycin–induced amnesia. *Physiological Psych.* 10, 283–292 (1982).

Quartermain, D. & Jung, H. Persistence of Retrieval Enhancement by Amphetamine Following Scopolamine–Induced Amnesia. *Pharmacology Biochem. Behav.* 33, 51–54 (1989).

Quartermain, D. et al. Amphetamine Enhances Retrieval Following Diverse Sources of Forgetting. *Physiological & Behavior* 43, 239–241 (1988).

Richards, J.B. et al. Trained and Amphetamine–Induced Circling Behavior in Lesioned Transplanted Rats. *J. Neural Transplant Plast* 4, 157–166 (1993).

Richter–Levin, G. & Yaniv, D. Is LTP in the Hippocampus a Useful Model for Learning–Related Alterations in Gene Expression? *Rev. Neurosci.* 12, 28*9–296 (2001).

Riviere, G.J. et al. Disposition of Methamphetamine and its Metabolite Amphetamine in Brain and Other Tissues in Rats after Intravenous Administration. *J. Pharmacol. Exp. Ther.* 292, 1042–1047 (2000).

Sanders–Bush, E. & Sulser, F. Metabolic and Neurochemical Aspects of the Pharmacology of Amphetamine and Para–Chloramphetamine. 8, 69–70.

Sansone, M. et al. Minaprine, but not Oxiracetam, Prevents Desipramine–Induced Impairment of Avoidance Learning in Mice. *Pol. J. Pharmacol.* 47, 69–73 (1995).

Sara, S.J. & Deweer, B. Memory Retrieval Enhanced by Amphetamine after a Long Retention Interval. *Behav. Neural Biol.* 36, 146–160 (1982).

Soetens, E. et al. Amphetamine enhances human–memory consolidation. *Neurosci. Letters* 161, 9–12 (1993).

Soetens, E. et al. Effect of amphetamine on long–term retention of verbal material. *Psychopharmacology* 119, 155–162 (1995).

Strupp, B.J. et al. Time–Dependent Effects of Post–trail Amphetamine Treatment in Rats: Evidence for Enhanced Storage of Representational Memory. *Behavioral and Neural Biology* 56, 62–76 (1991).

Vree, T.B. & van Rossum, J.M. Kinetics of Metabolism and Excretion of Amphetamines in Man. *Amphetamines and Related Compounds Proceedings of the Mario Negri Institute for Pharmacological Res., Milan, Italy.* E. Costa & S. Garattini, eds. Raven Press, N.Y. 165–190 (1970).

Yi–Ping, H. & Lin, J.–S. Effects of modafinil and amphetamine on sleep–wake cycle after sleep deprivation in cats. *Acta. Pharmacol. Sin.* 20, 813–818 (Sep. 1999).

Zink, W.E. et al. Model Systems for Assessing Cognitive Function: Implications for HIV–1 Infection and Drugs of Abuse. *Neuroimmune Circuits, Drugs of Abuse, and Infectious Diseases* H. Friedman et al., eds. Kluwer Academic/Plenum Publishers 7–27 (2001).

Beckett, A.H. & Rowland, M. Urinary excretion kinetics of amphetamine in man. *J Pharm Pharmacol.* 17, 628–639 (Oct. 1965).

Jori, A. et al. Differences in the Availability of d–and l–Enantiomers after Administration of Racemic Amphetamine to Rats. *Xenobiotica* 8, 589–595 (1978).

Alles, G. Comparative Physiological Actions of Optically Isomeric Phenylisopropylamines. *Univ. of CA. Publ. Pharmacol.* 1, 129–150 (1939).

Angrist, B. et al. Comparative Psychotomimetic Effects of Stereoisomers of Amphetamine. *Nature* 234, 152–153 (19 Nov. 1971).

Arnold, L.E. et al. Levoamphetamine vs. Dextroamphetamine in Minimal Brain Dysfunction. *Arch. Gen. Psychiatry* 33, 292–301 (Mar. 1976).

Arnold, L.E. et al. Levoamphetamine and Dextroamphetamine: Comparative Efficacy in the Hyperkinetic Syndrome. *Arch. Gen. Psychiatry* 27, 816–822 (Dec. 1972).

Axelrod, J. et al. Effect of Psychotropic Drugs on the Uptake of H3–Norepinephrine by Tissues. *Science* 133, 383–384 (Feb. 10, 1961).

Brown, G.L. et al. Plasma Levels of d–Amphetamine in Hyperactive Children. *Psychopharmacology* 62, 133–140 (1979).

DeLuca, J. Cognitive Dysfunction After Aneurysm of the Anterior Communicating Artery. *J. Clin. Exp. Neuropsychology* 14, 924–934 (1992).

Goldstein L.B. Effects of amphetamines and small related molecules on recovery after stroke in animals and man. *Neuropharmacology* 39, 852–859 (2000).

Hartmann, E. & Cravens, J. Sleep: Effects of d– and l–Amphetamine in Man and Rat. *Psychopharmacology* 50, 171–175 (1976).

McIntyre, H.B. et al. Computer Anlayzed EEG in Amphetamine–Responsive Hyperactive Children. *Psychiatry Res.* 4, 189–197 (1981).

Myers, C.E. et al. Impaired Delay Eyeblink Classical Conditioning in Individuals with Anterograde Amnesia Resulting from Anterior Communicating Artery Aneurysm Rupture. *Behav. Neurosci.* 115, 560–570 (2001).

Parkes, J.D. & Fenton, G.W. Levo(–)amphetamine and dextro(+) amphetamine in the treatment of nacrolepsy. *J. Neurology, Neurosurg. & Psychiatry* 36, 1076–1081 (1973).

Parkes, J.D. et al. Amphetamines in the treatment of Parkinson's disease. *J. Neurology, Neurosurg. & Psychiatry* 38, 232–237 (1975).

Prinzmetal, M. & Alles, G.A. The Central Nervous System Stimulation Effects of Dextro–Amphetamine Sulphate. In *Stimulant Effects of Dextro–Amphetamine Sulphate* 200, 665–673 (Nov. 1940).

Simpson, L.L. Blood Pressure and Heart Rate Responses Evoked by d– and l–Amphetamine in the Pithed Rat Preparation. *J. Pharmacol. Exp. Therapeutics* 193, 149–159 (1975).

Song, J.K. et al. Neuroradiologic Diagnosis and Treatment of Vasospasm. *Cerebral Aneurysms* 7, 819–835 (Nov. 1997).

Van Kammen, D.P. & Murphy, D.L. Attenuation of the Euphoriant and Activating Effects of d– and l–Amphetamine by Lithium Carbonate Treatment, *Psychopharmacologia* 44, 215–224 (1975).

Walker–Batson, D. et al. Amphetamine Paired with Physical Therapy Acclerates Motor Recovery After Stroke, *Stroke* 26, 2254–2259 (Dec. 1995).

Wan, S.H. et al. Kinetics, salivary excretion of amphetamine isomers, and effect of urinary pH. *Clin. Pharmacol. Ther.* 23, 585–590 (May 1978).

Toxicology and Carcinogenesis Studies of dl–Amphetamine Sulfate (Cas No. 60–13–9) in F344/N Rate and B6C3F$_1$ Mice (Feed Studies), *National Toxicology Program, Technical Report Series No. 387* NIH Publication No. 91–2842 (Jun. 1991).

Richter, D., "Elimination of Amines in Man," *The Biochem. J.* 32:1763–1769 (1938).

Batterman, R.C., Combination Report to the Vicks Chemical Company, "Studies with Levo–Desoxyephedrine," Mar. 4, 1965.

Knoefel, P., "The Influence of Phenisopropyl Amine and Phenisopropyl Methyl Amine on Work Output," *Society for Pharmacol. Exp. Therapeutics*, p. 83 (1943).

Yasar, S., et al., "Preclinical Evaluation of l–Deprenyl: Lack of Amphetamine–Like Abuse Potential," *Inhibitors of Monoamine Oxidase B Pharmacology and Clinical Uses in Neurodegenerative Disorders,* I. Szelenyi, ed. (Switzerland: Birkhauser Verlag Basel), pp. 215–233 (1993).

Yasar, S. and Bergman, J., "Amphetamine–like effect of l–deprenyl (selegiline) in drug discrimination studies," *Clinical Pharmacology & Therapeutics,* 56(6): 768–773 (1994).

Shappell, S.A., et al., "Stimulated Sustained Flight Operations and Performance, Part 2: Effects of Dextro–Methamphetamine," *Military Psychology,* 4(4), 267–287 (2002).

Cook, C.F., et al., "Pharmacokinetics of Methamphetamine Self–Administered to Human Subjects by Smoking S–(+)–Methamphetamine Hydrochloride," *Drug Metabolism and Disposition,* 21(4): 717–723 (1993).

Vorhees, C.V., et al., "Adult Learning Deficits After Neonatal Exposure to D–Methamphetamine: Selective Effects on Spatial Navigation and Memory," *Journal of Neuroscience,* 20(12): 4732–4739 (2000).

Mann, J.J., et al., "A Controlled Study of the Antidepressant Efficacy and Side Effects of (–)–Deprenyl," *Arch Gen Psychiatry,* 46: 45–50 (1989).

Kohl, R.L., et al., "Arousal and Stability: The Effects of five New Sympathomimetic Drugs Suggest a New Principle for the Prevention of Space Motion Sickness," *Aviation, Space, and Environmental Medicine*: 137–143 (1986).

Wang, J.Q. and McGinty, J.F., "Dose–Dependent Alteration in *zif*268 and Preprodynorphin mRNA Expression Induced by Amphetamine or Metamphetamine in Rat Forebrain," *Journal of Pharmacology and Experimental Therapeutics,* 273(2): 909–917 (1995).

Malega, W.P., et al., "Pharmacokinetic and Pharmacodynamic Analysis of the Actions of D–Amphetamine and D–Methamphetamine on the Dopamine Terminal," *Journal of Pharmacology and Expeirmental Therpauetics,* 274(1): 90–96 (1995).

Bisagno, V., et al., "Short toxic methamphetamine schedule impairs object recognition task in male rats," *Brain Research* 940: 95–101 (2002).

Yamamoto, R., and Takasaki, K., "Involvement of Presynaptic $_{a2}$–Adrenoreceptors in the Depressor Response Produced by Repeated Administration of Dextro–Methamphetamine," *Journal Auton. Pharmac.,* 3: 79–88 (1983).

Cappon, G.D. and Vorhees, C.V., "Plasma and brain methamphetamine concentrations in neonatal rats," *Neurotoxicology and Teratology,* 23: 81–88 (2001).

Gyarmati, Z.S. et al., "Behavioural Consequences of Methamphetamine–Induced Neurotoxicity in Rats," *Neurobiology,* 9(1): 37–39 (2001).

Riviere, G.J., et al., "Spontaneous Locomotor Activity and Pharmacokinetics of Intravenous Methamphetamine and Its Matabolite Amphetamine in the Rat," *Journal of Pharmacology and Experimental Therapeutics,* 291(3): 1220–1226 (1999).

Haughey, H.M., et al., "Differential effects of methamphetamine on $NA^+/Cl^-$–dependent transporters," *Brain Research,* 863: 59–65 (2000).

Caldwell, J., et al., "Metabolism of [$^{14}$C]Methamphetamine in Man, the Guinea Pig and the Rat," *Biochem. Journal,* 129: 11–22 (1972).

Chapman, D.E., et al., "Long–Term Changes in Basal Ganglia Function after a Neurotoxic Regimen of Methamphetamine," *Journal of Pharmacology and Experimental Therapeutics,* 296(2): 520–527 (2001).

Melega, W.P., et al., "Effects of Deprenyl Metabolite, L–Methamphetamine on Striatal Dopamine Efflux," *Neurotransmissions, Neuromodulation,* A376, Abstract No. 2177.

Lin, L.Y., et al., "Cytochrome P4502D Isozymes Catalyze the 4–Hydroxylation of Methamphetamine Enantiomers," *Drug Metabolism and Disposition,* 23(6): 610–614 (1995).

Yanagisawa, Y., et al., "Association Equilibrium of d–Methamphetamine and l–Methamphetamine With Serum Albumin," *Chirality* 10: 742–746 (1998).

Melega, W.P., et al., l–Methamphetamine Pharmacokinetics and Pharmacodynamics for Assessment of in vivo Deprenyl–Derived l–Methamphetamine, *Journal of Pharmacology and Experimental Therapeutics,* 288(2): 752–758 (1999).

Yokel, R.A. and Pickens, R., "Self–Administration of Optical Isomers of Amphetamine and Methylamphetamine by Rats," *Journal of Pharmacology and Experimental Therapeutics,* 187(1): 27–33 (1973).

Ozaki, T., et al., "The Adverse Effects of l–Methamphetamine on the Development of Explanted Rat Embryos," *Asia–Oceania Journal Obstet. Gynaecol.* 18(3): 277–281 (1992).

Vidrio, H., "Cardiovascular Effects of Methamphetamine in Dogs Treated Chronically with the Amine," *Journal of Cardiovascular Pharmacology,* 4(2): 326–329 (1982).

Roth, L.W., et al., "A Comparison of the Analeptic, Circulatory and Other Properties of D– and L–Desoxyephedrine," *Arch. int. pharmacoyn.,* XCVII(3): 362–368 (1954).

Lehmann, H.E. and Ban, T.A., "Effects of Psychoactive Drugs on Conflict Avoidance Behavior in Human Subjects," *Activitas nervosa superior,* 13(2): 82–85 (1971).

Matthews, C., "Overweight Relapse: Effects of Training and Methamphetamine with Pentobarbital," *Current Therapeutic Research,* 12(1): 34–39 (1970).

Martin, W.R., et al., "Physiologic, subjective, and behavioral effects of amphetamine, methamphetamine, ephedrine, phenmetrazine, and methylphenidate in man," *Clinical Pharmacology and Therapeutics,* 12(2): 245–258 (1970).

Shimosato, K., "Urinary Excretion of p–Hydroxylated Methamphetamine Metabolites in Man. II. Effect of Alcohol Intake on Methamphetamine Metabolism," *Pharmacology Biochemistry & Behavior.* 29: 733–740 (1988).

Cookson, J. and Silverstone, T., "The Effects of Methamphetamine on Mood and Appetite in Depressed Patients: A Placebo–controlled Study," *International Clinical Psychopharmacology,* 1: 127–133 (1986).

Sim, T., et al., "Cognitive Deficits Among Methamphetamine Users with Attention Deficit Hyperactivity Disorder Symptomatology," *Journal of Addictive Diseases,* 2(1): 75–89 (2002).

Comer, S.D., et al., "Effects of repeated oral methamphetamine administration in humans," *Psychopharmacology,* 155: 397–404 (2001).

Mohs, R.C., et al. "Sensitivity of Some Human Cognitive Functions to Effects of Methamphetamine and Secobarbital," *Drug and Alcohol Dependence,* 5: 145–150 (1980).

Mohs, R.C., et al., "Methamphetamine and Diphenhydramine Effects on the Rate of Cognitive Processing," *Psychopharmacology,* 59: 13–19 (1978).

Kopell, B.S. and Wittner, W.K., "The Effects of Chlorpromazine and Methamphetamine on Visual Signal–From–Noise Detection," *Journal of Nervous and Mental Disease,* 147(4): 418–424 (1968).

Kraemer, T. and Maurer, H.H., "Determination of amphetamine, methamphetamine and amphetamine–derived designer drugs or medicaments in blood and urine," *Journal of Chromatography B,* 713: 163–187 (1998).

Kraemer, T. and Maurer, H.H., "Toxicokinetics of Amphetamines: Metabolism and Toxicokinetic Data of Designer Drugs, Amphetamine, Methamphetamine, and Their N–Alkyl Derivatives," *Therapeutic Drug Monitoring,* 24(2): 277–289 (2002).

Berlyne, D.E., "Arousal, Reward and Learning," *Annals New York Academy of Sciences,* 159(3): 1059–1070 (1969).

Chang, L., et al., "Perfusion MRI and computerized cognitive test abnormalities in abstinent methamphetamine users," *Psychiatry Research Neuroimaging,* 114: 65–79 (2002).

Mayfield, D.G., "The Effect of Intravenous Methamphetamine on Mood," *International Journal of Addictions,* 8(3): 565–568 (1973).

Volkow, N.D., et al., "Loss of Dopamine Transporters in Methamphetamine Abusers Recovers with Protracted Abstinence," *Journal of Neurosciences,* 21(23): 9414–9418 (2001).

Herrell, J.M., et al., "A Multisite Study of the Effectiveness of Methamphetamine Treatment: An Initiative of the Center for Substance Abuse Treatment," *Journal of Psychoactive Drugs,* 32(23): 143–147 (2000).

Perez–Reyes, M., et al., "Clinical Effects of Methamphetamine Vapor Inhalation," *Life Sciences,* 49(13): 953–959 (1991).

Karch, S.B., et al., "Methamphetamine–Related Deaths in San Francisco: Demographic, Pathologic, and Toxicologic Profiles," *Journal of Forensic Sciences,* 44(2): 359–368 (1999).

Hart, C.L., et al., "Methamphetamine self–administration by humans," *Psychopharmacology,* 157: 75–81 (2001).

Lechmann, H.E., et al., "The Effect of Psychostimulants on Psychometric Test Performance With Special Reference to Conflict Avoidance Behavior," *Current Therapeutic Research,* 12(6): 390–393 (1970).

Yui, K., et al., "Noradrenergic activity and spontaneous recurrence of methamphetamine psychosis," *Drug and Alcohol Dependence* 44: 183–187 (1997).

Perez–Reyes, M., "Differences in Sedative Susceptibility Between Types of Depression," *Arch Gen Psychiat.* 19: 64–71 (1968).

Shutter, L. and Garell, D.C., "Obesity in Children and Adolescents: A Double–Blind Study with Cross–Over," *Journal of School Health,* 273–275 (1966).

Ong, Y.I., et al., "Suppression of Bulimic Symptoms with Methylamphetamine," *Brit. Journal Psychiat.,* 143: 288–293 (1983).

Kopell, B.S., et al., "The Effects of Methamphetamine and Secobarbital on the Continent Negative Variation Amplitude," *Psychopharmacoligia (Berl.),* 34: 55–62 (1974).

Tariot, P.N., et al., "Cognitive effects of L–deprenyl in Alzheimer's Disease," *Psychopharmacology,* 91:489–495 (1987).

Filip, V. and Kolibas, E., "Selegiline in the treatment of Alzeheimer's disease: a long–term randomized placebo–controlled trial," *Journal of Psychiatry & Neuroscience,* 23(3): 234–243 (1999).

Finali, G. et al., "Alzheimer–type dementia and verbal memory performances: influence of selegiline therapy," *Ital. J. Neurol. Sci.* 13: 141–148 (1992).

Finali, G., et al., "L–Depreynl Therapy Improves Verbal Memory in amnesic Alzheimer Patients," *Clinical Neuropharmacology,* 14(6): 523–536 (1991).

Birks, J. and Flicker, L., "Selegiline for Alzheimer's disease," (Cochrane Review). In: *The Cochrane Library, Issue 2* (2002). Oxford: Update Software.

Yui, K. and Miura, T., "Behavioral Response Induced by Repeated Treatment with Methamphetamine Alone and in Combination with Scopolamine in Rats," *Neuropsychobiology,* 33: 21–27 (1996).

Mewaldt, S.P., and Ghoneim, M.M. "The Effects and Interactions of Scopolamine, Physostigmine and Methamphetamine on Human Memory", *Pharmacology Biochemistry & Behavior.* 10: 205–210 (1979).

Gordon, M.N., et al., "Oral Versus Transdermal Selegiline: Antidepressant–Like Activity in Rats," *Pharmacology Biochemistry and Behavior,* 63(3): 501–506 (1999).

Fang, J. and Yu, P.H., "Effect of L–Deprenyl, its Structural Analogues and some Monoamine Oxidase Inhibitors on Dopamine Uptake," *Neuropharmacology,* 33(6): 763–768 (1994).

Czub, M., et al., "Effects of Selegiline in a retroviral rat model for neurodegenerative disease," *Journal of NeuroVirology,* 5: 458–464 (1999).

Grasing, K., et al., "Biphasic Effects of Selegiline on Striatal Dopamaine: Lack of Effect on Methamphetamine–Induced Dopamine Depletion," *Neurochemical Research,* 26(1): 65–74 (2001).

Simpson, L.L., "Evidence That Deprenyl, A Type B Monoamine Oxidase Inhibitor, Is an Indirectly Acting Sympathomimetic Amine," *Biochemical Pharmacology,* 27: 1591–1595 (1978).

ThyagaRajan, S., et al., "Region–specific alterations in the concentration of catecholamines and indoleamines in the brains of young and old F344 rats after L–deprenyl treatment," *Brain Research Bulletin,* 48(5): 513–520 (1999).

Mills, D. and Ledger, R., "The Effects of Oral Selegiline Hydrochloride on Learning and Training in the Dog: A Psychobiological Interpretation," *Prog. Neuro–Psychopharmacol. & Biol. Psychiat.,* 25: 1597–1613 (2001).

Kim, E.M., et al., "Determination of Enantiomeric Metabolites of L–deprenyl, d–methamphetamine, and racemic methamphetamine in urine by capillary electrophoresis: comparison of deprenyl use and methamphetamine use," *Journal Anal Toxicol.,* 24(4): 238–244 (May–Jun. 2000).

Maruyama, W. and Naoi, M., "Neuroprotection by (–)–deprenyl and related compounds," *Mechanisms of Ageing and Development,* 111: 189–200 (1999).

Matsubara, K., et al., "L–Deprenyl Prevents the cell hyposia induced by dopaminergic neurotoxins, MPP+ and $\beta$–carbolinium: a microdialysis study in rats," *Neuroscience Letters,* 302: 65–68 (2001).

Dringenberg, H.C., et al., "Increased effectiveness of tacrine by deprenyl co–treatment in rats: EEG and behavioral evidence," *Neuropharmacology and Neurotoxicology,* 11(16): 3513–3516 (2000).

Szende, B., et al., "Anti–apoptotic and apoptotic action of (–)–deprenyl and its metabolites," *Journal Neral. Transm.,* 108: 25–33 (2001).

Szoko, E., et al., "Biotransformation of deprenyl enantiomers," *European Journal of Drug Metabolism and Pharmacokinetics,* 24(4): 315–319 (1999).

Milgram, N.W., et al., "The Effect of L–Deprenyl on Behavior, Cognitive Function, and Biogenic amines in the Dog," *Neurochemical Research,* 18(12): 1211–1219 (1993).

Sprague, J.E. and Nichols, D.E., "The Monoamine Oxidase–B Inhibitor L–Deprenyl Protects Against 3,4–Methylenedioxymethamphetamine–Induced Lipid Peroxidation and Long–term Serotonergic Deficits," *Journal of Pharmacology and Experimental Therapeutics,* 273(2): 667–673 (1995).

Kuhn, D.M., and Geddes, T.J., "Molecular Footprints and Neurotoxic Amphetamine Action," *Annals of the New York Academy of Sciences,* 914: 92–103 (2000).

Anisman, H. and Waller, T.G., "Effects of Methamphetamine and Shock Duration During Inescapable Shock Exposure on Subsequent Active and Passive Avoidance," *Journal of Comparative and Physiological Psychology,* 77(1): 143–151 (1971).

Miyamoto, K., "Conditioned Drug Effects of Pimozide, Haloperidol and Chlorpromazine on Methamphetamine–Induced Behavior," *Japanese Journal of Psychiatry and Neurology,* 44(3): 629–636 (1990).

Yamamura, T., et al., "Effects of daily administration of methamphetamine on multiple active/passive avoidance performance in rats," *Behavioural Brain Research,* 53: 105–112 (1993).

Munzar, P., et al., "Potentiation of the discriminative–stimulus effects of methamphetamine by the histamine $H_3$ receptor antagonists thioperamide in rats," *European Journal of Pharmacology,* 363: 93–101 (1998).

Shimada, A., et al., "Neurochemical Analysis of the Psychotoxicity of Methamphetamine and Cocaine by Microdialysis in the Rat Brain," *Annals of the New York Academy of Sciences,* 801(1): 361–370 (1996).

Arakawa, O., "Effects of Methamphetamine and Methylphenidate on Single and Paired Rat Open–Field Behaviors," *Physiology of Behavior,* 55(3): 441–446 (1994).

Plasznik, A. and Kostowski, W., "Effects of p–Bromo–Methamphetamine (V–111) on Conditioned Avoidance Behavior in Rats with Lesioned *Raphe Nuclei,*" *Fol. Journal Pharmacol. Pharm.* 21, 193–198 (1997).

Metcalf, F.U., et al., "Methamphetamine Effects Upon Avoidance Behavior during Limbic Seizures in the Cat," *Psychopharmacologia (Berl.),* 21: 390–400 (1971).

Sansome, M., et al., "Interaction between Nootropic Drugs and Methamphetamine on Avoidance Acquisition but not on Locomoter Activity in Mice," *Arch. Int. Pharmacodyn.,* 278: 229–235 (1985).

Cho, D., et al., "Behavioral Teratogenicity of Methamphetamine," Department of Toxicology, National Institute of Safety Research, Seoul, Korea., *Journal Toxicol. Sci.,* 16 (Supp. 1): 37–49 (1991).

Kasirsky, G. and Tansy, M.F., "Teratogenic Effects of Methamphetamine in Mice and Rabbits," *Teratology,* 4: 131–134 (1971).

Courtney, K.D. and Valerio, D.A., "Teratology in the *Macaca mulatta,*" *Teratology,* 1: 163–172 (1968).

Yamamura, T., et al., "Effects of Methamphetamine and Ethanol on Learning and Brain Neurotransmitters in Rats," *Pharmacology Biochemistry and Behavior,* 42: 389–400 (1992).

Moretti, R., et al., "Effects of selegiline on fronto–temporal dementia: a neuropsychological evaluation," *International Journal of Geriatric Psychiatry,* 17: 391–392 (2002).

Kulig, B. and Calhoun, W.H., "Enhancement of Successive Discrimination Reversal Learning by Methamphetamine," *Psychopharmacologia (Berl.),* 27: 233–240 (1972).

Witkin, J.M. et al., "Behavioral, Toxic and Neurochemical Effects of Sydnocarb, a Novel Psychomotor Stimulant: Comparisons with Methamphetamine," *Pharmacology and Experimental Therapeutics.* 288(3): 1298–1310 (1999).

Itoh, J., et al., "Utility of an elevated plus–maze for dissociation of amnesic and behavioral effects of drugs in mice," *European Journal of Pharmacology,* 194: 71–76 (1991).

Glennon, R.A., et al., "A Preliminary Behavioral Investigation of PMMA, the 4–Methoxy Analog of Methamphetamine," *Pharmacology Biochemistry & Behavior,* 31: 9–13 (1988).

Wolthuis, O.L., "Experiments With UCB 6215, A Drug Which Enhances Acquisition In Rats: Its Effects Compared With Those of Methamphetamine," *European Journal of Pharmacology,* 16: 238–297 (1971).

Johnson, B.A., et al., "Effects of Isradipine, A Dihydropyridine–Class Calcium Channel Antagonist, on D–Methamphetamine–Induced Cognitive and Physiological Changes in Humans," *Neurophychopharmacology,* 22(5): 504–512 (2000).

Cook, C.E., et al., Pharmacokinetics of Oral Methamphetamine and Effects of Repeated Daily Dosing in Humans, *Drug Metabolism and Disposition,* 20(6): 856–862 (1992).

Wiegmann, D.A., et al., "Methamphetamine Effects on Cognitive Processing During Extended Wakefulness," *The International Journal of Aviation Psychology,* 6(4): 379–397 (1996).

Scheinin, H., et al., "CYP2D6 polymorphism is not crucial for the disposition of selegiline," *Clinical Pharmacology & Therapeutics* 64(4): 402–411 (1998).

Musshoff, F., "Illegal of Legitimate Use? Precursor Compounds to Amphetamine and Methamphetamine," *Drug Metabolism Reviews,* 32(1): 15–44 (2000).

Cody, J.T., "Metabolic Precursors to Amphetamine and Methamphetamine," *Forensic Science Review,* 5(2): 110–127 (1993).

Elsworth, J.D., et al., "The Contribution of Amphetamine Metabolites of (–)Deprenyl to its Antiparkinsonian Properties," *Journal Neural Transmission,* 54: 105–110 (1982).

Ernst, M., et al., "Selegiline in Adults With Attention Deficit Hyperactivity Disorder: Clinical Efficacy and Safety," *Psychopharmacology Bulletin,* 32(3): 327–334 (1996).

Ernst, M., et al., "Seleginine in ADHD Adults: Plasma Monoamines and Monoamine Metabolits," *Neuropsychopharmacology,* 16(4): 276–284 (1997).

Heinonen, E., et al., "Pharmacokinetic aspects of l–deprenyl (selegiline) and its metabolites," *Clinical Pharmacology & Therapeutics,* 56(6), part 2, 742–749 (1994).

Van Alvea, O.E., and Donnelly, W.A., "Systemic Effects of Intranasal Medication," *Eye, Ear, Nose & Throat Monthly,* 31: 476–480 (1952).

Bromage, P.R., "Comparison of Vasoactive Drugs in Man," *British Medical Journal,* 72–74 (Jul. 12, 1952).

Jirovsky, D., et al., "The Pilot Study of Methamphetamine Anantiometer Metabolism in Man by Capillary Electrophoresis," *Chemica,* 40: 25–34 (2001).

Foster, B.S. and Gilbert, D.D., "Enantiometric Determination of Amphetamine and Methamphetamine in Urine by Precolumn Derivatization with Marfey's Reagent and HPLC," *Journal of Analytical Toxicology,* 22: 265–269 (1998).

Teter, D.F., "Metabolism of Diet Pill to Amphetamine and Methamphetamine," (Letters to the Editor), *JOEM,* 41(3): 139 (1999).

Jirovsky, D., et al., "Methamphetazmine—properties and anlaytical methods of enantiometer determination," *Forensic Science International,* 96: 61–70 (1998).

Cooke, B.J.A., "Chirality of Methamphetamine and Amphetamine from Workplace Urine Samples", *Journal of Analytical Toxicology,* 18: 49–51 (1994).

Hornbeck, C.L. and Czarney, R.J., "Retrospective Analysis of Some L–Methamphetamine/L–Amphetamine Urine Data," *Journal of Analytical Toxicology,* 17: 23–25 (1993).

Haley, T.J., "Desoxyephedrine—A Review of the Literature, ", *Journal of the American Pharmaceutical Association,* 36(6): 161–169 (1947).

Fitzgerald, R.L., et al., "Resolution of Methamphetamine Stereosiomers in Urine Testing: Urinary Excretion of R(–)–Methamphetamine Following Use of Nasal Inhalers," *Journal of Analytical Toxicology,* 12: 255–259 (Sep.–Oct. 1988).

Cody, J.T. and Schwarzhoff, R., "Interpretation of Methamphetamine and Amphetamine Enantiomer Data," *Journal of Anlaytical Toxicology,* 17: 321–326 (Oct., 1993).

Ferrando, R.L., et al., "Biazarre Behavior Following the Ingestion of Levo–Desoxyephedrine," *Drug Intelligence and Clinical Pharmacy,* 22: 214–216 (1988).

Tatton, W.G., "Selegiline Can Mediate Neuronal Rescue Rather Than Neuronal Protection," *Movement Disorder Society,* 8(Suppl. 1): S20–S30 (1993).

Laine, K., et al., "Multiple–Dose Pharmaceokinetics of Selegiline and Desmethylselegiline Suggest Saturable Tissue Binding," *Clinical Neuropharmacology,* 23(1): 22–27 (2000).

Ebadi, M., et al., "Neuroprotective Actions of Selegiline," *Journal of Neuroscience Research,* 67: 285–289 (2002).

Dixit, S.N., et al., "Effect of Selegiline on Cognitive Functions in Parkinson's Disease," *JAPI*, 47(8): 784–786 (1999).

Bodkin, J.A. and Amsterdam, J.D., "Transdermal Selegiline in Major Depression: a Double–Blind, Placebo–Controlled, Parallel–Group Study in Outpatients," *Am. J. Psychiatry*, 159(11): 1869–1875 (2002).

Riederere, P. and Przuntek, H. (eds.), "MAO–B–Inhibitor Selegiline R–(–)–Deprenyl), A New Therapeutic Concept in the Treatment of Parkinson's Disease," *Journal of Neural Transmission*, Supp. 25: (1987).

Bartzokis, G., et al., "Selegiline Effects on Cocaine–Induced Changes in Medial Temporal Lobe Metabolism and Subjective Ratings of Euphoria," *Neuropsychopharmacology*, 20(6): 582–590 (1999).

Alafuzoff, I., et al., "Selegiline treatment and the extent of degenerative changes in brain tissue of patients with Alzheimer's disease," *Eur. J. Clin. Pharmacol*, 55: 815–819 (2000).

Yoshida, T., et al., "Metabolism of deprenyl, a selective monoamine oxidase (MAO) β inhibitor in rat: relationship of metabolism to MAO–β–inhibitory potency," *Zenobiotica*, 16(2): 129–136 (1986).

Lajtha, A., et al., "Mebabolism of (–)–Deprenyl and PF–(–)–Deprenyl in Brain After Central and Peripheral Administration," *Neurochemical Research*, 21(10): 1155–1160 (1996).

Golbe, L.I., et al., "Selegiline and Parkinson's Disease: Protective and Symptomatic Considerations," *Drugs*, 39(5): 646–651 (1990).

Riley, D.E., "Reversible Transverse Fetishism in a Man With Parkinson's Disease Treatment With Selegiline," *Clinical Neuropharmacology*, 25(4): 234–237 (2002).

Heinonen, E.H., et al., "Pharmacokinetics and Metabolism of Selegiline," *Acta Nerol Scand.*, 126: 93–99 (1989).

Tariot, P.N., et al., "L–Deprenyl in Alzheimer's Disease," *Arch. Gen Psychiatry*, 44: 427–433 (1987).

Karoum, F., et al., "Metabolism of (–) deprenyl to amphetamine and methamphetamine may be responsible for deprenyl's therapeutic benefit: A biochemical assessment," *Neurology (Ny)*, 32: 503–509 (1982).

Donnan, P.T., et al., "Selegiline and mortality in subjects with Parkinson's disease: A longitudinal community study," (Reply from the authors), *Neurology*, 57(2): Correspondence (2001).

Przuntek, H., et al., "SELEDO: a 5–year long–term trial on the effect of selegiline in early parkinsonian patients treated with levodopa," *European Journal of Neurology*, 6: 141–150 (1999).

Schachter, M., et al., "Deprenyl in the management of response fluctiation in patients with Parkinson's disease on levodopa," *Journal of Neurology, Neurosurgery, and Psychiatry*, 43: 1016–1021 (1980).

Sano, M., et al., "A Controlled Trial of Selegiline, Alpha–Tocopherol, or Both as Treatment for Alzheimer's Disease," *The New England Journal of Medicine*, 336(17): 1216–1222 (1997).

Reynolds, G.P., et al., "Deprenyl is Metabolized to Methamphetamine and Amphetamine in Man," *Br. J. Clin. Pharmac.*, 6: 542–544 (1978).

Riederer, P., et al., "On The Mode of L–Deprenyl in the Human Central Nervous System," *Journal of Neural Transmission*, 43: 217–226 (1978).

Knoll, J., "The Pharmacology of (–)Deprenyl," *Journal Neural Transm. (Suppl)*, 22: 75–89 (1986).

Knoll. J., "The Possible Mechanisms of Action of (–)Deprenyl in Parkinson's Disease," *Journal Neural Transmission*, 43: 177–198 (1978).

Fowler, J.S., et al., "Evidence that L–deprenyl treatment for one week does not inhibit MAO A or the dopamine transporter in the human brain," *Life Sciences*, 68: 2759–2768 (2001).

Parkinson Study Group, "Impact of Deprenyl and Tocopherol Treatment on Parkinson's Disease in DATATOP Subjects Not Requiring Levodopa," *Annals of Neurology*, 39(1): 29–36 (1996).

Wilcock, G.K., et al., "The effect of selegiline in the treatment of people with Alzheimer's disease: a meta–analysis of published trials," *International Journal of Geriatric Psychiatry* 17: 175–183 (2002).

Chrisp, P., et al., "Selegiline: A Review of its Pharmacology, Symptomatic Benefits and Protective Potential in Parkinson's Disease," *Drugs & Aging*, 1(3): 228–248 (1991).

Birkmayer, W., "Long Term Treatment With L–Deprenyl", *Journal of Neural Transmission*, 43: 239–244 (1978).

Csanda, E., et al., "Experiences with L–Deprenyl in Parkinsonism," *Journal Neural Transmission*, 43: 263–269 (1978).

Larsen, J.P., et al., "Doses selegilien modify the progression of early Parkinson's disease? Results from a five–year study," *European Journal of Neurology*, 6: 539–547 (1999).

Bauer and Evey, "Differential Effects of L–Amphetamine on Ontogeny of Active Avoidance, Intertitial Responses, and Locomotor Activity", *Psychopyharmacology* 75: 299–304 (1981).

Yasar, S. et al., "Evaluation of the Stereoisomers of Deprenyl for Amphetamine–Like Discriminative Stimulus Effects in Rats," *J. Pharmacology and Experimental Therapeutics* 265: 1–6 (1993).

Brandeis, R. et al., "Improved of Cognitive Function by MAO–B Inhibitor L–Deprenyl in Aged Rats," *Pharmacology Biochemistry and Behavior*, 39: 297–304 (1991).

Mangoni, "Effects of a MAO–B Inhibitor in the Treatment of Alzheimer Diseease," *Eur. Neurol.* 31: 100–107 (1991).

Kirrane et al., "Effects of Amphetamine on Visuospatial Working Memory Performance in Schizophrenia Spectrum Personality Disorder," *Neuropsychopharmacology* 22(1): 14–18 (1999).

Barch, D.M., et al., "The Effects of D–Amphetamine on Language Function in Schizophrenia," *Society for Neuroscience Abstracts* 23(1–2): p. 1952 (1997).

Stein, L., et al., "Memory Enhancement by Central Administration of Norepinephrine," Online Database Biosis, Accession No. PREV197559062381, *Brain Research* 84(1): 329–335 (1975).

Nicholaus, B.J.R., "Symbiotic Approach to Drug Design," *Decision Making in Drug Research*, pp. 173–186 (1983).

Quartermain, D., et al., "Alleviation of Scopolamine Amnesia by Different Retrieval Enhancing Treatments," *Pharmacol. Biochem. Behav.* 30(4): 1093–1096 (1988).

Reus, V.I., et al., "d–Amphetamine: Effects on memory in a Depressed Population," *Biol. Psychol.*, 14(2): 345–356 (1979).

Yonkov, D.I., "Participation of Cholinergic Mechanics in The Memory Effects of CNS Stimulants," *Advanced In The Bioscience, Pergamon Press, GB.*, 59: 347–350 (1986).

METHODS AND COMPOSITIONS FOR REGULATING MEMORY CONSOLIDATION

REFERENCE TO RELATED APPLICATIONS

This application claims priority to U.S. Provisional Patent Application No. 60/245,323 filed on Nov. 1, 2000, the specification of which is incorporated by reference herein.

BACKGROUND OF THE INVENTION

The term "memory" subsumes many different processes and requires the function of many different brain areas. Overall, human memory provides declarative recall, e.g., for facts and events accessible to conscious recollection, and non-declarative recall, e.g., procedural memory of skills and operations not stored regarding time and place. Research in recent years has provided information necessary to understand many of the various components of memory and has identified associated brain regions. A newly acquired experience initially is susceptible to various forms of disruption. With time, however, the new experience becomes resistant to disruption. This observation has been interpreted to indicate that a labile, working, short-term memory is consolidated into a more stable, long-term memory.

Behavioral research has found that the human mind consolidates memory at certain key time intervals. The initial phase of memory consolidation occurs in the first few minutes after an exposure to a new idea or learning experience. The next phase occurs over a longer period of time, such as during sleep. If a learning experience has on-going meaning to us, the next week or so serves as a further period of memory consolidation. In effect, in this phase, the memory moves from short-term to long-term storage.

Moreover, various mechanisms have been proposed to account for the formation of long-term memory. A wide range of observations suggest an evolutionarily conserved molecular mechanism involved with the formation of long-term memory. These include increased release of synaptic transmitter, increased number of synaptic receptors, decreased $K_D$ of receptors, synthesis of new memory factors either in the presynaptic or postsynaptic element, sprouting of new synaptic connections, increase of the active area in the presynaptic membrane and many others. Synaptic plasticity, the change in the strength of neuronal connections in the brain, is thought to underlie long-term memory storage.

"Memory consolidation", or long-term memory is also believed to play a crucial role in a variety of neurological and mental disorders, including mental retardation, Alzheimer's disease and depression. Indeed, loss or impairment of long-term memory is a significant feature of such diseases, and no effective therapy for that effect has emerged. Short-term, or "working" memory, is generally not significantly impaired in such patients.

Accordingly, methods and compositions that enhance long-term memory function and/or performance, or prophylactically (e.g., as a neuroprotective treatment) prevent or slow degradation of long-term memory function and/or performance would be desirable. Similarly, methods and compositions for restoring long-term memory function and/or performance are needed.

SUMMARY OF THE INVENTION

The present invention relates to the discovery that the amphetamine class of compounds (collectively referred to herein as "amphetamine compounds") can be used to enhance, prevent and/or restore long-term memory function and performance, e.g., to improve long-term memory (LTM) in animal subjects. More particularly, the invention relates to the discovery that a particular enantiomer of amphetamine compounds is effective for such therapeutic use.

One aspect of the invention features a pharmaceutical kit comprising one or more amphetamine compound(s) in an amount sufficient to enhance long-term memory in a patient, a pharmaceutically acceptable carrier, and instructions (written and/or pictorial) describing the use of the formulation for enhancing memory.

Another aspect of the invention features a pharmaceutical preparation comprising one or more amphetamine compounds provided as a single oral dosage formulation in an amount sufficient to enhance long-term memory in a patient but resulting in a concentration in the patient lower than its EC50 as a CNS stimulant.

Another aspect of the invention features a pharmaceutical preparation comprising one or more amphetamine compounds provided in the form of a transdermal patch and formulated for sustained release of the amphetamine(s) in order to administer an amount sufficient to enhance long-term memory in a patient but resulting in a concentration in the patient lower than its EC50 as a CNS stimulant.

In preferred embodiments the pharmaceutical kits and preparations of this invention comprise at least one of the amphetamine compounds represented by Formula I, or a pharmaceutically acceptable salt, solvate, metabolite or prodrug thereof:

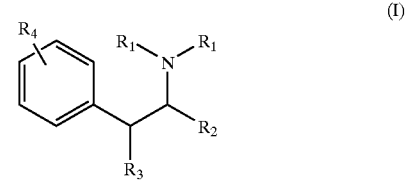

(I)

wherein, as valence and stability permit, $R_1$, independently for each occurrence, represents hydrogen or substituted or unsubstituted lower alkyl, lower alkenyl, lower alkynyl, aratkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulflydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido.

In certain embodiments, $R_3$ represents hydrogen, while in other embodiments, $R_3$ represents lower alkyl, such as methyl, ethyl, propyl, isopropyl, n-butyl, isobutyl, t-butyl, etc., hydroxy, amino, or carbonyl.

In certain embodiments, $R_4$ represents hydrogen, while in other embodiments, $R_4$ represents from 1 to 3 substituents on the ring to which it is attached selected from halogen, hydroxy, amino, sulfhydryl, cyano, nitro, lower alkyl, and sulfate.

In certain embodiments, $R_4$ represents hydrogen and at least one of R1, $R_2$, and $R_3$ represents hydrogen. In certain embodiments, $R_4$ represents hydrogen and at least two of $R_1$, $R_2$, and $R_3$ represents hydrogen. In certain embodiments, $R_4$ represents hydrogen and at least three of $R_1$, $R_2$, and $R_3$ represent hydrogen. In certain embodiments, $R_4$ represents hydrogen and all four of $R_1$, $R_2$, and $R_3$ represent hydrogen.

In certain embodiments, one $R_1$ represents hydrogen, one $R_1$ represents lower alkyl, such as methyl, ethyl, propyl, isopropyl, n-butyl, isobutyl, t-butyl, etc., $R_2$ represents lower alkyl, such as methyl, ethyl, propyl, isopropyl, n-butyl, isobutyl, t-butyl, etc., $R_3$ and $R_4$ represent hydrogen.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 3 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, R2 represents methyl, and $R_3$ and $R_4$ independently and for each occurrence represent hydrogen.

In other preferred embodiments the pharmaceutical kits and preparations of this invention comprise at least one of the amphetamine compounds as a pharmaceutically acceptable salt represented by Formula II:

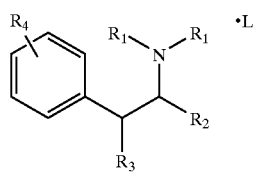

(II)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido; and L is a non-toxic organic or inorganic acid.

In certain embodiments, $R_3$ represents hydrogen, while in other embodiments, $R_3$ represents lower alkyl, such as methyl, ethyl, propyl, isopropyl, n-butyl, isobutyl, t-butyl, etc., hydroxy, amino, or carbonyl.

In certain embodiments, $R_4$ represents hydrogen, while in other embodiments, $R_4$ represents from 1 to 3 substituents on the ring to which it is attached selected from halogen, hydroxy, amino, sulfhydryl, cyano, nitro, lower alkyl, and sulfate.

In certain embodiments, $R_4$ represents hydrogen and at least one of $R_1$, $R_2$, and $R_3$ represents hydrogen. In certain embodiments, $R_4$ represents hydrogen and at least two of $R_1$, $R_2$, and $R_3$ represents hydrogen. In certain embodiments, $R_4$ represents hydrogen and at least three of $R_1$, $R_2$, and $R_3$ represent hydrogen. In certain embodiments, $R_4$ represents hydrogen and all four of $R_1$, $R_2$, and $R_3$ represent hydrogen.

In certain embodiments, one RI represents hydrogen, one $R_1$ represent lower alkyl, such as methyl, ethyl, propyl, isopropyl, n-butyl, isobutyl, t-butyl, etc., R2 represents lower alkyl, such as methyl, ethyl, propyl, isopropyl, butyl, isobutyl, t-butyl, etc., $R_3$ and $R_4$ represent hydrogen.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

In other preferred embodiments the pharmaceutical kits and preparations of this invention comprise at least one of the amphetamine compounds as an amphetamine metabolite represented by Formula III:

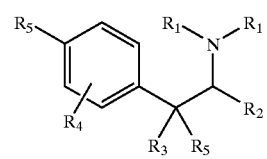

(III)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_2$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, $R_3$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, $R_4$ represents from 1 to 3 substituents on the ring to which it is attached, e.g., selected from hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido;

$R_5$ independently for each occurrence, represents hydrogen or hydroxy.

In certain embodiments, $R_3$ represents hydrogen, while in other embodiments, $R_3$ represents lower alkyl, such as methyl, ethyl, propyl, isopropyl, n-butyl, isobutyl, t-butyl, etc., hydroxy, amino, or carbonyl.

In certain embodiments, $R_4$ represents hydrogen, while in other embodiments, $R_4$ represents from 1 to 3 substituents on the ring to which it is attached selected from halogen, hydroxy, amino, sulflydryl, cyano, nitro, lower alkyl, and sulfate.

In certain embodiments, $R_4$ represents hydrogen and at least one of $R_1$, $R_2$, and $R_3$ represents hydrogen. In certain embodiments, $R_4$ represents hydrogen and at least two of $R_1$, $R_2$, and $R_3$ represent hydrogen. In certain embodiments, $R_4$ represents hydrogen and at least three of $R_1$, $R_2$, and $R_3$ represent hydrogen. In certain embodiments, $R_4$ represents hydrogen and all four of $R_1$, $R_2$, and $R_3$ represent hydrogen.

In certain embodiments, one $R_1$ represents hydrogen, one $R_1$ represent lower alkyl, such as methyl, ethyl, propyl, isopropyl, n-butyl, isobutyl, t-butyl, etc., R2 represents lower alkyl, such as methyl, ethyl, propyl, isopropyl, n-butyl, isobutyl, t-butyl, etc., $R_3$ and $R_4$ represent hydrogen.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

In certain preferred embodiments a metabolite of amphetamine compounds is selected from p-hydroxyamphetamine, benzyl methyl ketone, 1-phenylpropan-2-ol, benzoic acid, glycine, hippuric acid, p-hydroxynorephedrine, and N-hydroxylaamphetamine.

In certain preferred embodiments of the kits, preparations, compositions and methods, the invention features a pharmaceutical kit or preparation comprising a mixture of at least a single species of amphetamine compounds-or at least two different species of amphetamine compounds. The different species of amphetamine compounds can be present in equal or in differing amounts with respect to one another.

In other preferred embodiments of the kits, preparations, compositions and methods, the invention features a composition comprising at least 51 mol percent, 75 mol percent, 95 mol percent, or 99 mol percent of the eutomer with respect to the distomer of that amphetamine compound.

In other preferred embodiments of the kits, preparations, compositions and methods, the invention features one or more amphetamine compound(s) provided in an amount sufficient to enhance long-term memory in a patient by a statistically significant amount when assessed by a standardized performance test.

In certain embodiments of the kits, preparations, compositions and methods, the invention features one or more amphetamine compound(s) comprising at least 2-fold less, or at least 4-fold less of R-(−)-amphetamine as compared to an equally effective long term memory enhancing dose of S-(+)-amphetamine.

In certain embodiments of the kits, preparations, composition and methods, the invention features one or more amphetamine compound(s) provided in an amount sufficient to enhance long-term memory in a patient by a statistically significant amount when assessed by one or more of a Cambridge Neuropsychological Test Automated Battery (CANTAB); a Children's Memory Scale (CMS); a Contextual Memory Test; a Continuous Recognition Memory Test (CMRT); a Denman Neuropsychology Memory Scale; a Fuld Object Memory Evaluation (FOME); a Graham-Kendall Memory for Designs Test; a Guild Memory Test; a Learning and Memory Battery (LAMB); a Memory Assessment Clinic Self-Rating Scale (MAC-S); a Memory Assessment Scales (MAS); a Randt Memory Test; a Recognition Memory Test (RMT); a Rivermead Behavioral Memory Test; a Russell's Version of the Wechsler Memory Scale (RWMS); a Test of Memory and Learning (TOMAL); a Vermont Memory Scale (VMS); a Wechsler Memory Scale; and a Wide Range Assessment of Memory and Learning (WRAML).

In certain embodiments of the kits, preparations, compositions and methods, the invention features one or more amphetamine compound(s) provided in an amount sufficient to enhance long-term memory in a patient by a statistically significant amount when assessed by a Providence Recognition Memory Test.

In certain embodiments of the kits, preparations, compositions and methods, the invention features one or more amphetamine compound(s) provided in the form of a saccharate, a sulfate or an aspartate.

In another embodiment of the kits, preparations, compositions and methods, the invention further features a neuronal growth factor, a neuronal survival factor, a neuronal trophic factor, a cholinergic modulator, an adrenergic modulator, a nonadrenergic modulator, a dopaminergic modulator, a glutaminergic modulator or an agent that stimulates PKC, PKA, GABA, NMDA, cannabinoid, AMPA, kainate, phosphodiesterase (PDE), CREB or nootropic pathways. In another embodiment of the kits, preparations, compositions and methods, the invention further features methylphenidate.

Another aspect of the invention features the use of the pharmaceutical composition of amphetamine compounds in the manufacture of a medicament for prophylaxis or treatment of an animal susceptible to or suffering from anxiety, depression, age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, mental retardation, Alzheimer's disease, age, attention deficit disorder, attention deficit hyperactivity disorder, or AIDS-related dementia, which amphetamine compound is represented by Formula I, or a pharmaceutically acceptable salt, solvate, metabolite or pro-drug thereof:

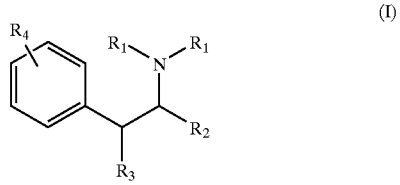

(I)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylarnino, sulfhydryl, alkylthio, cyano, nitro, ester, ketone, formyl, amido, acylamino; acyloxy, lower alkyl, lower alkenyl, sulfonate ester, amidino, sulfonyl, sulfoxido, sulfamoyl, and sulfonamido.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

Another aspect of the invention features the use of an amphetamine compound in the manufacture of a medicament for prophylaxis or treatment of an animal susceptible to or suffering from anxiety, depression, age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, mental retardation, Alzheimer's disease, age, attention deficit disorder, attention deficit hyperactivity disorder, or AIDS-related dementia, which amphetamine compound is represented by Formula II:

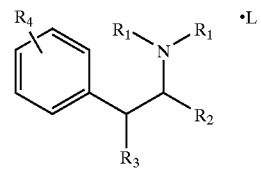

(II)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido; and L is a non-toxic organic or inorganic acid.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

Another aspect of the invention features the use of an amphetamine compound in the manufacture of a medicament for prophylaxis or treatment of an animal susceptible to or suffering from anxiety, depression, age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, mental retardation, Alzheimer's disease, age, attention deficit disorder, attention deficit hyperactivity disorder, or AIDS-related dementia, which amphetamine compound is represented by Formula m:

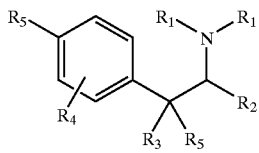

(III)

wherein, as valence and stability permit,
  $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;
  $R_2$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;
  $R_3$ is absent or represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;
  $R_4$ represents from 1 to 3 substituents on the ring to which it is attached, e.g., selected from hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido;
  $R_5$ independently for each occurrence, represents hydrogen or hydroxy.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, $R_2$ represents methyl, and $R_3$ and $R_4$ independently and for each occurrence represent hydrogen.

In certain embodiments, the animal to be treated is a mammal. In certain preferred embodiments the animal to be treated is a human, dog, cat, cattle, horse, sheep, hog or goat.

In certain embodiments, the pharmaceutical composition is for oral administration.

In certain other embodiments the pharmaceutical composition is a transdermal patch. In certain embodiments the transdermal patch includes one or more penetration enhancers.

In certain embodiments, the pharmaceutical composition features an amphetamine compound provided as at least 51 mol percent, or at least mol 75 percent, or at least 95 mol percent, or at least 99 mol percent of the of the eutomer with respect to the distomer of that amphetamine compound.

In certain embodiments, the pharmaceutical composition features an amphetamine compound provided in an amount sufficient to enhance long-term memory in a patient by a statistically significant amount when assessed by a standardized performance test.

In certain embodiments, the pharmaceutical composition features one or more amphetamine compound(s) provided in an amount sufficient to enhance long-term memory in a patient by a statistically significant amount when assessed by one or more of a Cambridge Neuropsychological Test Automated Battery (CANTAB); a Children's Memory Scale (CMS); a Contextual Memory Test; a Continuous Recognition Memory Test (CMRT); a Denman Neuropsychology Memory Scale; a Fuld Object Memory Evaluation (FOME); a Graham-Kendall Memory for Designs Test; a Guild Memory Test; a Learning and Memory Battery (LAMB); a Memory Assessment Clinic Self-Rating Scale (MAC-S); a Memory Assessment Scales (MAS); a Randt Memory Test; a Recognition Memory Test (RMT); a Rivermead Behavioral Memory Test; a Russell's Version of the Wechsler Memory Scale (RWMS); a Test of Memory and Learning (TOMAL); a Vermont Memory Scale (VMS); a Wechsler Memory Scale; and a Wide Range Assessment of Memory and Learning (WRAML).

In certain embodiments, the pharmaceutical composition features one or more amphetamine compound(s) provided in an amount sufficient to enhance long-term memory in a patient by a statistically significant amount when assessed by a Providence Recognition Memory Test.

In certain embodiments, the pharmaceutical composition features one or more amphetamine compound(s) provided in the form of a saccharate, a sulfate or an aspartate.

In other embodiments of the kits, preparations, compositions and methods, the invention further features amphetamine compound(s) being provided as a single oral dosage formulation in an amount sufficient to enhance long-term memory in a patient but resulting in a concentration in the patient lower than its EC50 as a CNS stimulant.

In other embodiments of the kits, preparations, compositions and methods, the invention further features amphetamine compound(s) being provided for treating and/or preventing memory impairment, wherein the memory impairment results from one or more of anxiety, depression, age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, mental retardation, Alzheimer's disease, age, attention deficit disorder, attention deficit hyperactivity disorder, or AIDS-related dementia.

In other embodiments of the kits, preparations, compositions and methods, the invention further features amphetamine compound(s) being provided for enhancing memory in normal individuals.

In certain preferred embodiments of the kits, preparations, compositions and methods, the invention features one or more amphetamine compound(s), wherein the amphetamine compound is (R)-(–)-amphetamine.

In certain preferred embodiments of the kits, preparations, compositions and methods, the invention features one or more amphetamine compound(s), wherein the amphetamine compound is (R)-(–)-methamphetamine.

In certain preferred embodiments of the kits, preparations, compositions and methods, the invention features single oral dosage formulations of 2.5 mg to 25, 50, 75, 100 or even 125 mg of (R)-(–)-amphetamine and a pharmaceutically acceptable carrier.

In certain embodiments, the invention features a method for enhancing memory in an animal, comprising administering to the animal a composition of an amphetamine compound in an amount sufficient to enhance long-term memory in the animal, wherein the composition includes at least 51 mol percent of the eutomer of the amphetamine compound represented by Formula I, or pharmaceutically acceptable salt, solvate, metabolite or pro-drug thereof, relative to the distomer of that amphetamine compound:

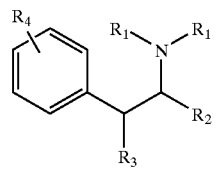

(I)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylaldyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylarnino, acyloxy, lower alkyl, lower alkenyl, sulfonate ester, amidino, sulfonyl, sulfoxido, sulfamoyl, and sulfonamido.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, R2 represents methyl, and $R_3$ and $R_4$ independently and for each occurrence represent hydrogen.

In certain embodiments, the invention features a method for enhancing memory in an animal, comprising administering to the animal a composition of an amphetamine compound in an amount sufficient to enhance long-term memory in the animal, wherein the composition includes at least 51 mol percent of the eutomer of the amphetamine compound, relative to the distomer of that amphetamine compound, wherein the amphetamine compound is a pharmaceutically acceptable salt represented by Formula II:

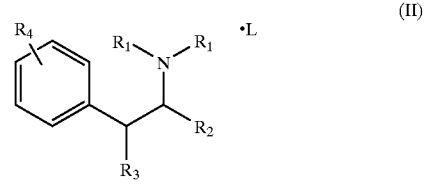

(II)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;

$R_4$ represents from 1 to 3 substituents on the ring to which it is attached, selected from the group consisting of hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido; and L is a non-toxic organic or inorganic acid.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, R2 represents methyl, and $R_3$ and $R_4$ independently and for each occurrence represent hydrogen.

In certain embodiments, the invention features a method for enhancing memory in an animal, comprising administering to the animal a composition of an amphetamine compound in an amount sufficient to enhance long-term memory in the animal, wherein the composition includes at least 51 mol percent of the eutomer of the amphetamine compound, relative to the distomer of that amphetamine compound, wherein the amphetamine compound is an amphetamine metabolite represented by Formula III, or pharmaceutically acceptable salt, solvate, or pro-drug thereof.

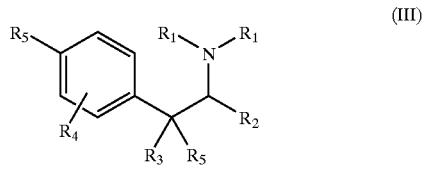

(III)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_2$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_3$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;

$R_4$ represents from 1 to 3 substituents on the ring to which it is attached, e.g., selected from hydrogen, halogen, hydroxy, alkoxy, amino, alkylamino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido;

$R_5$ independently for each occurrence, represents hydrogen or hydroxy.

In certain preferred embodiments, one occurrence of $R_1$ represents hydrogen, the second occurrence of $R_1$ represents hydrogen, or lower alkyl; $R_2$ represents hydrogen or lower alkyl, $R_3$ represents hydrogen or lower alkyl, and $R_4$ represents hydrogen or from 1 to 2 substituents on the ring to which it is attached, selected from halogen, trifluoromethyl, hydroxy, amino, cyano, nitro, and lower alkyl.

In certain preferred embodiments, $R_4$ represents hydrogen and at least one of $R_1$, $R_2$, and $R_3$ represents hydrogen.

In certain preferred embodiments, $R_4$ represents hydrogen and at least two of $R_1$, $R_2$, and $R_3$ represent hydrogen.

In certain preferred embodiments, both occurrences of $R_1$ represent independently hydrogen, $R_2$ represents methyl, $R_3$ represents hydrogen and $R_4$ represents hydrogen.

In certain preferred embodiments, one occurrence of $R_1$ represents hydrogen, the second occurrence of $R_1$ represents methyl, $R_2$ represents methyl, $R_3$ represents hydrogen and $R_4$ represents hydrogen.

In most preferred embodiments, $R_1$, independently and for each occurrence, represents hydrogen, R2 represents methyl, and $R_3$ and $R_4$ independently and for each occurrence represent hydrogen.

In certain embodiments, the invention features a kit comprising an amphetamine compound formulation, e.g., as described herein and preferably provided in single oral dosage form or as a transdermal patch for enhancing memory in a patient (preferably a human), and in association with instructions (written and/or pictorial) describing the use of the formulation for enhancing memory, and optionally, warnings of possible side effects and drug-drug or drug-food interactions.

Another aspect of the invention relates to a method for conducting a pharmaceutical business, which includes: (a) manufacturing the kits, preparations, and compositions of the present invention; and (b) marketing to healthcare providers the benefits of using the kits, preparations, and compositions of the present invention to enhance memory of treated patients.

Another aspect of the invention relates to a method for conducting a pharmaceutical business, comprising: (a) providing a distribution network for selling the kits, preparations, and compositions of the present invention; and (b) providing instruction material to patients or physicians for using the kits, preparations, and compositions of the present invention to enhance memory of treated patients.

Yet another aspect of the invention relates to a method for conducting a pharmaceutical business, comprising: (a) determining an appropriate dosage of an amphetamine compound to enhance memory function in a class of patients; (b) conducting therapeutic profiling of one or more formulations of the amphetamine compound identified in step (a), for efficacy and toxicity in animals; and (c) providing a distribution network for selling the formulations identified in step (b) as having an acceptable therapeutic profile.

For instance, the subject business method can include an additional step of providing a sales group for marketing the preparation to healthcare providers.

Another aspect of the invention relates to a method for conducting a pharmaceutical business, comprising: (a) determining an appropriate dosage of an amphetamine compound to enhance memory function in a class of patients; and (b) licensing, to a third party, the rights for further development and sale of the amphetamine compound for enhancing memory.

In certain embodiments of the method, the class of patients suffer from memory impairment. In preferred embodiments of the method, the memory impairment results from one or more of anxiety, depression, age-associated memory impairment, minimal cognitive impairment, amnesia, dementia, learning disabilities, memory impairment associated with toxicant exposure, brain injury, brain aneurysm, Parkinson's disease, head trauma, Huntington's disease, Pick's disease, Creutzfeldt-Jakob disease, stroke, schizophrenia, epilepsy, mental retardation, Alzheimer's disease, age, attention deficit disorder, attention deficit hyperactivity disorder, or AIDS-related dementia. In other preferred embodiments of the method, the class of patients are normal individuals.

Another aspect of the invention features solid dosage form comprising an amphetamine compound represented by Formula I, or a pharmaceutically acceptable salt, solvate, metabolite or pro-drug thereof, in an amount of 25 mg or less:

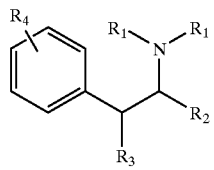

(I)

wherein, as valence and stability permit,
  $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;
  $R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;
  $R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;
  $R_4$ represents from 1 to 3 substituents on the ring to which it is attached, selected from the group consisting of hydrogen, halogen, hydroxy, alkoxy, amino, alkylarnino, sulfhydryl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, and sulfonamido.

Another aspect of the invention features solid dosage form comprising a pharmaceutically acceptable salt of an amphetamine compound represented by Formula II, solvate, metabolite or pro-drug thereof, in an amount of 25 mg or less:

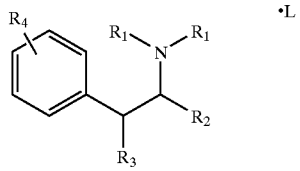

(II)

wherein, as valence and stability permit,
  $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl;
  $R_2$ represents hydrogen or substituted or unsubstituted lower alkyl, lower alkenyl, lower alkynyl, aralkyl, aryl, heteroaralkyl, heteroaryl, cycloalkyl, or cycloalkylalkyl;
  $R_3$ represents hydrogen or substituted or unsubstituted lower alkyl, lower alkenyl, lower alkynyl, aralkyl, aryl, heteroaralkyl, heteroaryl, cycloalkyl, or cycloalkylalkyl;
  $R_4$ represents from 1 to 3 substituents on the ring to which it is attached, selected from the group consisting of hydrogen, halogen, hydroxy, alkoxy, amino, alkylarnino, sulfhydryl, alkylthio, cyano, nitro, ester, ketone, formyl, amido, acylamino, acyloxy, lower alkyl, lower alkenyl, ester, amidino, sulfonyl, sulfoxido, sulfamoyl, and sulfonamido; and
  L is a non-toxic organic or inorganic acid.

Another aspect of the invention features solid dosage form comprising an amphetamine metabolite represented by Formula III, solvate or pro-drug thereof, in an amount of 25 mg or less:

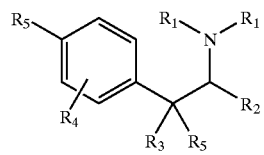

(III)

wherein, as valence and stability permit,
  $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;
  $R_2$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;
  $R_3$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy;
  $R_4$ represents from 1 to 3 substituents on the ring to which it is attached, e.g., selected from hydrogen, halogen, hydroxy, alkoxy, amino, alkylarnino, sulfhydryl, alkylthio, cyano, nitro, ester, ketone, formyl, amido, acylarnino, acyloxy, lower alkyl, lower alkenyl, sulfonate ester, amidino, sulfonyl, sulfoxido, sulfamoyl, sulfonamido;
  $R_5$ independently for each occurrence, represents hydrogen or hydroxy.

The practice of the present invention will employ, unless otherwise indicated, conventional techniques of synthetic chemistry, organic chemistry, inorganic chemistry, organometallic chemistry, pharmaceutical chemistry, and behavioral science, which are within the skill of the art. Such techniques are described in the literature. See, for example, *Advanced Organic Chemistry: Reactions, Mechanisms, And Structure* by J. March (John Wiley and Sons, N.Y., 1992); *The Chemist's Companion: A Handbook Of Practical Data, Techniques, And References* by A. J. Gordon and R. A. Ford (Wiley, N.Y., 1972); *Synthetic Methods Of Organometallic And Inorganic Chemistry* by W. A. Herrmann and Brauer (Georg Thieme Verlag, N.Y., 1996); *Experimental Organic Chemistry* by D. Todd (Prentice-Hall, N.J., 1979); *Experimental Organic Chemistry: Standard And Microscale* by L. M. Harwood (Blackwell Science, M.A., 1999); *Experimental Analysis Of Behavior* by I. H. Iversen and K. A. Lattal (Elsevier, N.Y., 1991); *A Practical Guide To Behavioral Research: Tools And Techniques* by R. Sommer and B. Sommer (Oxford University Press, N.Y., 2002); *Advances In Drug Discovery Techniques* by A. L. Harvey (Chichester, N.Y., 1998); *Quantitative Calculations In Pharmaceutical Practice And Research* by T. P. Hadjiioannou (VCH, N.Y., 1993); *Drug Fate And Metabolism: Methods And Techniques* by E. R. Garrett and J. L. Hirtz (M. Dekker, N.Y., 1977); *Behavioral Science Techniques: An Annotated Bibliography For Health Professionals* by M. K. Tichy (Praeger Publishers, N.Y., 1975).

DETAILED DESCRIPTION OF THE INVENTION

I. Overview

Figure 1:
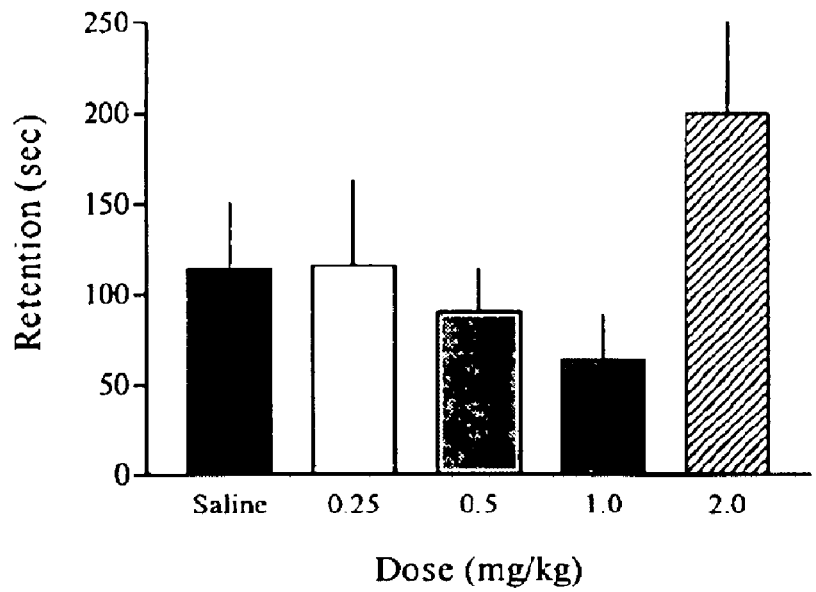
FIG. 1 presents the effectiveness of various doses of S-(+)-amphetamine on Performance in the Inhibitory Avoidance Task.

The present invention relates to the discovery that the amphetamine class of compounds (collectively referred to herein as "amphetamine compounds") can be used to enhance and/or restore long-term memory function and performance, e.g., to improve long-term memory (LTM) in animal subjects. More particularly, the invention relates to the discovery that a particular enantiomer of amphetamine compounds is effective for therapeutic use.

Amphetamine is a nervous system stimulant that depresses blood pressure, appetite and breathing. Abuse of amphetamine has been shown to cause severe side effects including dependence and possibly induced psychosis. Amphetamine is synonymous with actedron; actemin; adderall; adipan; akedron; allodene; alpha-methyl-(±)-benzeneethanamine; alpha-methylbenzeneethanamine; alpha-methylphenethylamine; amfetamine; amphate; anorexine; benzebar; benzedrine; benzyl methyl carbinamine; benzolone; beta-amino propylbenzene; beta-phenylisopropylamine; biphetamine; desoxynorephedrine; dietamine; DL-amphetamine; elastonon; fenopromin; finam; isoamyne; isomyn; mecodrin; monophos; mydrial; norephedrane; novydrine; obesin; obesine; obetrol; octedrine; oktedrin; phenamine; phenedrine; phenethylamine, alpha-methyl-; percomon; profamina; profetamine; propisamine; racephen; raphetamine; rhinalator, sympamine; simpatedrin; simpatina; sympatedrine; and weckamine.

The present invention contemplates, in part, the use of an amphetamine composition which is enriched for one enantiomer. In particular, we describe herein the use of pharmaceutical preparations for increasing long-term potentiation and/or improving long-term memory in animals, such as humans, which include R-(−)-amphetamine or a derivative thereof. R-(−)-amphetamine is at least 4 times more effective as a memory enhancer as compared to the commonly prescribed S-(+) enantiomer of amphetamine. In addition, unlike S-(+)-amphetamine, the R-(−) enantiomer has not been shown to be addictive.

In certain embodiments, a mixture of enantiomers of the subject compounds may be employed, e.g., a racemic mixture containing both enantiomers of a chosen compound, e.g., with each enantiomer being present in equal amounts, or in differing amounts. In certain embodiments, the therapeutic preparation may be enriched to provide predominantly one enantiomer of a subject compound. An enantiomerically enriched mixture may comprise, for example, at least 60 mol percent of one enantiomer, or more preferably at least 75, 90, 95 or even 99 mol percent. In preferred embodiments, the amphetamine compound provided in the formulation is at least 60 mol percent of the eutomer relative to the distomer of the amphetamine compound, and more preferably at least 75, 90, 95 or even 99 mol percent.

The subject amphetamine compounds can also be provided in the form of pharmaceutical salts and as prodrugs.

In certain embodiments, the method includes administering, conjointly with the pharmaceutical preparation, one or more of a neuronal growth factor, a neuronal survival factor, and a neuronal trophic factor. Additionally or alternatively, a subject compound may be administered in conjunction with a cholinergic, adrenergic, nonadrenergic, dopaminergic, or glutaminergic modulator. Other agents directed at modulating GABA, NMDA, cannabinoid, AMPA, kainate, phosphodiesterase (PDE), PKA, PKC, CREB or nootropic systems may be important to the improvement of cognitive function and may be administered in conjunction with a subject compound. An agent to be administered conjointly with a subject compound may be formulated together with a subject compound as a single pharmaceutical preparation, e.g., as a pill or other medicament including both agents, or may be administered as a separate pharmaceutical preparation.

In another aspect, the present invention provides pharmaceutical preparations comprising, as an active ingredient, an enantiomerically enriched preparation of R-(−) amphetamine or a derivative thereof The subject amphetamine compound is formulated in an amount sufficient to improve LTM in an animal. The subject preparations and methods can be treatments using amphetamine compounds effective for human and/or animal subjects. In addition to hunans, other animal subjects to which the invention is applicable extend to both domestic animals and livestock, raised either as pets or for commercial purposes. Examples are dogs, cats, cattle, horses, sheep, hogs, and goats.

Still another aspect of the invention relates to the use of enantiomerically enriched preparations of amphetamine compounds for lessening the severity or prophylactically preventing the occurrence of learning and/or memory defects in an animal, and thus, altering the learning ability and/or memory capacity of the aninmal. As a result, the compounds of the present invention may be useful for treating and/or preventing memory impairment, e.g., due to toxicant exposure, brain injury, brain aneurysm, age-associated memory impairment, mild cognitive impairment, epilepsy, mental retardation in children, and dementia resulting from a disease, such as Parkinson's disease, Alzheimer's disease, AIDS, head trauma, Huntington's disease, Pick's disease, Creutzfeldt-Jakob disease, and stroke. In addition, the compounds of the invention may be useful in enhancing memory in normal individuals.

The invention also relates to the conjoint use of an amphetamine compound with agents that mimic or stimulate PKC and/or PKA pathways.

II. Definitions

For convenience, certain terms employed in the specification, examples, and appended claims are collected here.

As used herein, the terms "amphetamine" and "amphetamine compounds" are 20 meant to include amphetamine, analogs of amphetamine, enantiomerically or isomerically enriched amphetamine, and enantiomerically or isomerically enriched analogs of amphetamine, as well as pharmaceutically acceptable salts of such compounds and prodrugs. In particular, amphetamine compounds of the invention, or analogs thereof, include compounds having the structure as given in Formula I above. The dextro isomer of "amphetamine" is referred to in the art as the d, (+), D or S isomer and is represented by the general formula:

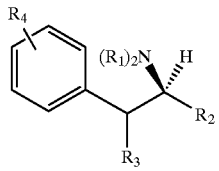

wherein $R_1$ for both occurrences represents hydrogen, $R_2$ represents methyl, $R_3$ represents hydrogen, and $R_4$ represents hydrogen. Similarly, for the purpose of this application dextro isomers of "amphetamine compounds", referred also as (+), D or S isomers, are defined by the same absolute configuration at the specified chiral center in the formula above, wherein $R_1$, $R_2$, $R_3$ and $R_4$ substituents are defined throughout this application. In certain circumstances, the identity of the R2 group may result in the opposite absolute configuration at the chiral center as defined above. However, for simplicity, all compounds with the absolute configuration at the specified chiral center as defined in the formula above will be referred to as (+), D or S amphetamine isomers. The levo isomer of "amphetamine" is referred to in the art as the 1, (−), L or R isomer and is represented by the general formula:

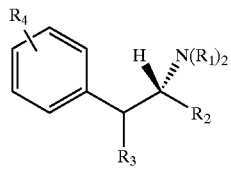

wherein $R_1$ for both occurrences represents hydrogen, $R_2$ represents methyl, $R_3$ represents hydrogen, and $R_4$ represents hydrogen. Similarly, for the purpose of this application levo isomers of "amphetamine compounds", referred also as (−), L or R isomers, are defined by the same absolute configuration at the specified chiral center in the formula above, wherein $R_1$, $R_2$, $R_3$ and $R_4$ substituents are defined throughout this application. In certain circumstances, the identity of the $R_2$ group may result in the opposite absolute configuration at the chiral center as defined above. However, for simplicity, all compounds with the absolute configuration at the specified chiral center as defined in the formula above will be referred to as (−), L or R amphetamine isomers. The racemic mixtures may be referred to as d,l or (+,−) or (±) or DL or (R)(S).

The term "$ED_{50}$" means the dose of a drug which produces 50% of its maximum response or effect.

An "effective amount" of, e.g., an amphetamine compound, with respect to the subject method of treatment, refers to an amount of the activator in a pharmaceutical preparation which, when applied as part of a desired dosage regimen brings about enhanced LTM according to clinically acceptable standards.

The term "$LD_{50}$" means the dose of a drug which is lethal in 50% of test subjects.

A "patient" or "subject" to be treated by the subject method can mean either a human or non-human animal.

The term "prodrug" represents compounds which are rapidly transformed in vivo, for example, by hydrolysis in blood into the therapeutically active agents of the present invention. A common method for making a prodrug is to include selected moieties which are converted under physiologic conditions (enzymatic or nonenzymnatic) to reveal the desired molecule. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergarnon Press, 1987, both of which are incorporated herein by reference.

The term "therapeutic index" refers to the therapeutic index of a drug defined as $LD_{50}/ED_{50}$.

By "transdermal patch" is meant a system capable of delivery of a drug to a patient via the skin, or any suitable external surface, including mucosal membranes, such as those found inside the mouth. Such delivery systems generally comprise a flexible backing, an adhesive and a drug retaining matrix, the backing protecting the adhesive and matrix and the adhesive holding the whole on the skin of the patient. On contact with the skin, the drug-retaining matrix delivers drug to the skin, the drug then passing through the skin into the patient's system.

The term "adrenergic" refers to neurotransmitters or neuromodulators chemically related to adrenaline (epinephrine) or to neurons which release such adrenergic mediators. Examples are dopamine, norepinephrine, epinephrine. Such agents are also referred to as catecholamines, which are derived from the amino acid tyrosine.

The term "biogenic amines" refers to a class of neurotransmitters which include catecholamines (e.g., dopamine, norepinephrine, and epinephrine) and serotonin.

The term "catecholamines" refers to neurotrarsmitters that have a catechol ring (e.g., a 3,4-dihydroxylated benzene ring). Examples are dopamine, norepinephrine, and epinephrine.

The term "cholinergic" refers to neurotransmitters or neuromodulators chemically related to choline or to neurons which release such cholinergic mediators.

The term "dopaminergic" refers to neurotransmitters or neuromodulators chemically related to dopamine or to neurons which release such dopaminergic mediators.

The term "dopamine" refers to an adrenergic neurotransmitter, as is known in the art.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxy groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O-$(CH_2)_m$—$R_8$, where $R_8$ represents an aryl, a cycloalkyl, a cycloalkenyl, a heterocycle or a polycycle; and m is zero or an integer in the range of 1 to 8.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 8 or fewer carbon atoms in its backbone (e.g., $C_1$–$C_8$ for straight chains, $C_3$–$C_8$ for branched chains), and more preferably 5 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be fuirther substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to eight carbons, more preferably from one to five carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S-$(CH2)_m$—$R_8$, wherein $R_8$ represents an aryl, a cycloalkyl, a cycloalkenyl, a heterocycle or a polycycle; and in is zero or an integer in the range of 1 to 8. Representative alkylthio groups include methylthio, ethylthio, and the like.

The terms "amine" and "amino" are art-recognized and refer to both unsubstituted and substituted amines, e.g., a moiety that can be represented by the general formula:

wherein $R_9$ and $R_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and in is zero or an integer in the range of 1 to 8. In preferred embodiments, $R_9$ and $R_{10}$ each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

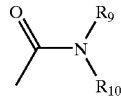

wherein $R_9$, $R_{10}$ are as defined above. Preferred embodiments of the amide will not include imides which may be unstable.

The term "aralkyl", as used herein, refers to an alkyl group substituted with an aryl group (e.g., an aromatic or heteroaromatic group).

The term "aryl" as used herein includes 5-, and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles", "heteroaryls", or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle" or "cyclic alkyl", as used herein, refers to an aromatic or non-aromatic ring in which each atom of the ring is carbon.

The term "carbonyl" is art-recognized and includes such moieties as can be represented by the general formula:

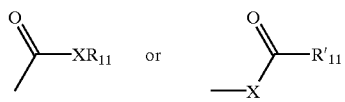

wherein X is a bond or represents an oxygen or a sulfur, and $R_{11}$ represents a hydrogen, an alkyl, an alkenyl, —$(CH2)_m$—$R_8$ or a pharmaceutically acceptable metal or aminergic counterion, $R'_{11}$ represents a hydrogen, an alkyl, an alkenyl or —$(CH2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_1$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are nitrogen, oxygen and sulfur.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "metabolites" refers to active derivatives produced upon introduction of a compound into a biological milieu, such as a patient.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2nd ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "statistically significant" as used herein means that the obtained results are not likely to be due to chance fluctuations at the specified level of probability. The two most commonly specified levels of significance are 0.05 (p=0.05) and 0.01 (p=0.01). The level of significance equal to 0.05 and 0.01 means that the probability of error is 5 out of 100 and 1 out of 100, respectively.

The term "sulfamoyl" is art-recognized and includes a moiety that can be represented by the general formula:

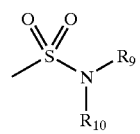

in which $R_9$ and $R_{10}$ are as defined above.

The term "sulfate" is art recognized and includes a moiety that can be represented by the general formula:

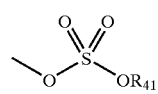

in which $R_{41}$ is absent or represents a metal or aminergic counterion, hydrogen, alkyl, cycloalkyl, or aryl.

The term "sulfonamido" is art recognized and includes a moiety that can be represented by the general formula:

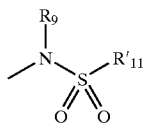

in which $R_9$ and $R'_{11}$ are as defined above.

The term "sulfonate" is art-recognized and includes a moiety that can be represented by the general formula:

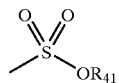

in which $R_{41}$ is as defined above.

The terms "sulfoxido" or "sulfinyl", as used herein, refers to a moiety that can be represented by the general formula:

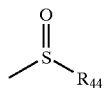

in which $R_{44}$ is selected from the group consisting of hydrogen, alkyl, alkenyl, alkynyl, cycloalkyl, heterocyclyl, aralkyl, or aryl.

The term "sulfonyl", as used herein, refers to a moiety that can be represented by the general formula:

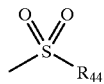

in which $R_{44}$ is selected from the group consisting of hydrogen, alkyl, alkenyl, alkynyl, cycloalkyl, heterocyclyl, aryl, or heteroaryl.

Analogous substitutions can be made to alkenyl and alkynyl groups to produce, for example, aminoalkenyls, aminoalkynyls, amidoalkenyls, amidoalkynyls, iniinoalkenyls, iminoalkynyls, thioalkenyls, thioalkynyls, carbonyl-substituted alkenyls or alynyls.

As used herein, the definition of each expression, e.g., alkyl, m, n, etc., when it occurs more than once in any structure, is intended to be independent of its definition elsewhere in the same structure.

Contemplated equivalents of the compounds described above include compounds which otherwise correspond thereto, and which have the same general properties thereof (e.g., the ability to effect long-term memory), wherein one or more simple variations of substituents are made which do not adversely affect the efficacy of the compound. In general, the compounds of the present invention may be prepared by the methods described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

III. Exemplary Compounds of the Invention

In preferred embodiments of the invention, a compound useful in the compositions and methods described herein has a structure of Formula I:

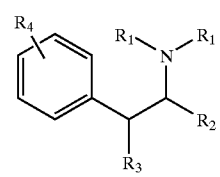

(I)

wherein, as valence and stability permit, $R_1$, independently for each occurrence, represents H or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_2$ represents H or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_3$ represents H or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_4$ is absent, or represents from 1 to 3 substituents on the ring to which it is attached, e.g., selected from halogen, hydroxy, alkoxy, amino, alkylamino, sulfhydtyl, alkylthio, cyano, nitro, ester, ketone, formyl, amido, acylamino, acyloxy, lower alkyl, lower alkenyl, sulfonate ester, amidino, sulfonyl, sulfoxido, sulfamoyl, sulfonamido, and phosphonate, etc.

In certain embodiments, at least one occurrence of $R_1$ represents hydrogen. In certain embodiments, both occurrences of $R_1$ represent hydrogen. In other embodiments, one occurrence of $R_1$ represents lower alkyl, such as methyl, ethyl, propyl, isopropyl, n-butyl, isobutyl, t-butyl, etc.

In certain embodiments, $R_2$ represents hydrogen, while in other embodiments, $R_2$ represents lower alkyl, such as methyl, ethyl, propyl, isopropyl, n-butyl, isobutyl, t-butyl, etc.

In certain embodiments, $R_3$ represents hydrogen, while in other embodiments, $R_3$ represents lower alkyl, such as methyl, ethyl, propyl, isopropyl, n-butyl, isobutyl, t-butyl, etc., hydroxy, amino, or carbonyl.

In certain embodiments, $R_4$ represents hydrogen, while in other embodiments, $R_4$ represents from 1 to 3 substituents on the ring to which it is attached selected from halogen, hydroxy, amino, sulffiydryl, cyano, nitro, and lower alky.

In certain embodiments, $R_4$ represents hydrogen and at least one of $R_1$, $R_2$, and $R_3$ represents hydrogen. In certain embodiments, $R_4$ is absent and at least two of $R_1$, $R_2$, and $R_3$ represent hydrogen. In certain embodiments, $R_4$ represents hydrogen and at least three of $R_1$, $R_2$, and $R_3$ represent hydrogen. In certain embodiments, $R_4$ represents hydrogen and all four of $R_1$, $R_2$, and $R_3$ represent hydrogen.

As set out above, certain embodiments of compounds of formula I may contain a basic functional group, such as amino or alkylamino, and thus, can be utilized in a free base form or as pharmaceutically acceptable salt forms derived from pharmaceutically acceptable organic and inorganic acids.

The pharmaceutically acceptable salts of the subject compounds represented by formula I include the conventional non-toxic salts of the compounds, e.g., from non-toxic organic or inorganic acids. For example, such conventional non-toxic salts include those derived from inorganic acids such as hydrochloric, hydrobromic, sulfuric, sulfarnic, phosphoric, nitric, and the like; and the salts prepared from organic acids such as acetic, 2-acetoxybenzoic, ascorbic, benzene sulfonic, benzoic, chloroacetic, citric, ethane disulfonic, ethane sulfonic, formic, ftimaric, gluconic, glutamic, glycolic, hydroxymaleic, isothionic, lactic, maleic, malic, methanesulfonic, oxalic, palmitic, phenylacetic, propionic, salicyclic, stearic, succinic, sulfanilic, tartaric, toluenesulfonic, and the like.

In certain embodiments, such salts have a structure represented by the general formula II:

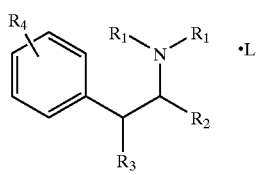

(II)

wherein, as valence and stability permit, $R_1$, $R_2$, $R_3$, and $R_4$ are defined as above;

L is a non-toxic organic or inorganic acid.

In certain embodiments, L is selected from the following inorganic acids: hydrochloric, hydrobromic, nitric, phosphoric, sulfamic, and sulfuric, or from the following organic acids: 2-acetoxybenzoic, ascorbic, benzene sulfonic, benzoic, chloroacetic, citric, ethane disulfonic, ethane sulfonic, formic, fiumaric, gluconic, glutamic, glycolic, hydroxymaleic, isothionic, lactic, maleic, malic, methanesulfonic, oxalic, palmitic, phenylacetic, propionic, salicyclic, stearic, succinic, sulfanilic, tartaric, and toluenesulfonic.

The compounds of the present invention further include metabolites of the subject amphetamine compounds, included but not limited to the following: p-hydroxyamphetamine, benzyl methyl ketone, 1-phenylpropan-2-ol, benzoic acid, glycine, hippuric acid, p-hydroxynorephedrine, and N-hydroxylamphetamine.

In certain embodiments, these metabolites have a structure represented by the general formula III:

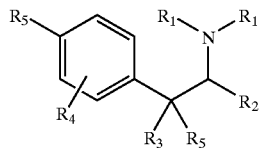

(III)

wherein, as valence and stability permit, $R_1$, independently for each occurrence, represents hydrogen or substituted or unsubstituted lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_2$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_3$ represents hydrogen or lower alkyl, lower alkenyl, lower alkynyl, aralkyl, aryl, heteroaralkyl, heteroaryl, cycloalkyl, or cycloalkylalkyl, e.g., optionally substituted by one or more substitutents such as halogen, hydroxy, alkoxy, etc.;

$R_4$ represents from 1 to 3 substituents on the ring to which it is attached, e.g., selected from hydrogen, halogen, hydroxy, alkoxy, amino, alkylamino, sulfhydryl, alkylthio, cyano, nitro, ester, ketone, formyl, amido, acylamnino, acyloxy, lower alkyl, lower alkenyl, sulfonate ester, amidino, sulfonyl, sulfoxido, sulfamoyl, sulfonamido, and phosphonate, etc.;

$R_5$ independently for each occurrence, represents hydrogen or hydroxy.

In certain embodiments, the method includes administering, conjointly with the pharnaceutical preparation, one or more of a neuronal growth factor, a neuronal survival factor, and a neuronal trophic factor. Additionally or alternatively, a subject compound may be administered in conjunction with a cholinergic, adrenergic, noradrenergic, dopaminergic, glutaminergic or other modulators. Other agents directed at modulating GABA, NMDA, cannabinoid, AMPA, kainate, phosphodiesterase (PDE), PKA, PKC, CREB or nootropic systems may be important to the improvement of cognitive function and may be administered in conjunction with a subject compound.

An agent to be administered conjointly with a subject compound may be formulated together with a subject compound as a single pharmaceutical preparation, e.g., as a pill or other medicament including both agents, or may be administered as a separate pharmaceutical preparation.

In another aspect, the present invention provides pharmaceutical preparations comprising, as an active ingredient amphetamine or a derivative thereof. The subject amphetamine compound is formulated in an amount sufficient to improve LTP in an animal. The subject preparations and methods can be treatments using amphetamine compounds effective for human and/or animal subjects In addition to humans, other animal subjects to which the invention is applicable extend to both domestic animals and livestock, raised either as pets or for commercial purposes. Examples are dogs, cats, cattle, horses, sheep, hogs, and goats.

Still another aspect of the invention relates to the use of amphetamine compounds for lessening the severity or prophylactically preventing the occurrence of learning and/or memory defects in an animal, and thus, altering the learning ability and/or memory capacity of the animal. As a result, the compounds of the present invention may be usefull for treating and/or preventing memory impairment, e.g., due to toxicant exposure, brain injury, brain aneurysm, age-associated memory impairment, mild cognitive impairment, epilepsy, mental retardation in children, and dementia resulting from a disease, such as Parkinson's disease, Alzheimer's disease, AIDS, head trauma, Huntington's disease, Pick's disease, Creutzfeldt-Jakob disease, Anterior Communicating Artery Syndrome, hypoxia, post cardiac surgery, Downs Syndrome and Stroke. In addition, the compounds of the invention may be useful in enhancing memory in normal individuals.

The invention also relates to the conjoint use of a amphetamine compound with agents that mimic or stimulate PKC and/or PKA pathways.

A. Synthesis of Amphetamine Compounds

As described in further detail below, it is contemplated that the subject methods can be carried out using amphetamine, particularly R-(−)-amphetamine, or a variety of different derivatives thereof. The suitability of use of a particular amphetamine compound can be readily determined, for example, by such drug screening assays as described herein.

The subject amphetamine compounds, and derivatives thereof, can be prepared readily by employing known synthetic methodology. As is well known in the art, these coupling reactions are carried out under relatively mild conditions and tolerate a wide range of "spectator" functionality. Additional compounds may be synthesized and tested in a combinatorial fashion, to facilitate the identification of additional amphetamine compounds which may be employed in the subject method.

Numerous methods for synthesizing amphetamine and for resolving the enantiomers of amphetamine have been described in the art, see for example: U.S. Pat. No. 5,075,338 to Knoll et al.; U.S. Pat. No. 2,828,343 to Tindall; U.S. Pat. No. 3,458,576 to Bryan; UK Patent No. GB 2,122,617; U.S. Pat. No. 3,996,381 to Florvall et al.; Croce et al., 1996, Gazz. Chim. Ital. 126:107–109; Mastagli et. al., 1950, Bull. Soc. Chim. Fr. 1045–1047; Smith et al., 1988, J. Med. Chem. 31:1558–1566; Bobranskii et al., 1941, J. Applied Chem. (U.S.S.R.) 14:410–414; Magidson, 1941, J. Gen. Chem. (U.S.S.R.) 11:339–343. The contents of these publications are incorporated herein by reference.

In one embodiment, a subject amphetamine compound can be synthesized according to the methods set forth in U.S. Pat. 5,075,338. Briefly, amphetamine compounds of the general formula:

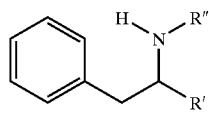

can be prepared by reacting a ketone of the formula:

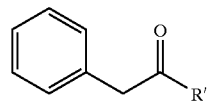

with an amine of the formula: R"NH$_2$ and reducing the ketimine intermediate formed without or after isolation. The reduction can be carried out by methods known per se, e.g., by catalytic hydrogenation (preferably in the presence of a palladium or Raney-nickel catalyst) or by using a complex metal hydride (e.g. sodium borohydride) or with the aid of a conventional reducing agent (e.g. sodium dithionite or amalgamated aluminum).

R-(−)-amphetamine and S-(+)-amphetamine may be obtained by optical resolution of racemic mixtures of R- and S-enantiomers of amphetarnine. Such a resolution can be accomplished by any conventional resolution methods well known to a person skilled in the art, such as those described in J. Jacques, A. Collet and S. Wilen, "Enantiomers, Racemates and Resolutions," Wiley, N.Y. (1981). For example, the resolution may be carried out by preparative chromatography on a chiral column. Another example of a suitable resolution method is the formation of diastereomeric salts with a chiral acid such as tartaric, malic, mandelic acid or N-acetyl derivatives of amino acids, such as N-acetyl leucine, followed by recrystallization to isolate the diastereomeric salt of the desired R enantiomer.

In one embodiment, a subject R-(−)-arnphetamine may be resolved according to the methods set forth in J. Med. Chem, 1988, 31:1558:1570. Briefly, racemic amphetamine is combined with a hot ethanol solution of D-(−)-tartaric acid. The solution is allowed to cool to room temperature and the white crystals are collected and recrystallized twice more from ethanol to give D-tartaric. acid salt of R-(−)-amphetamine. To recover R-(−)-amphetarnine, the D-tartaric acid salt of R-(−)-amphetamine is treated with sodium hydroxide in water and extracted with diethyl ether.

The compounds of the present invention may also be provided in the form of prodrugs, e.g., to protect a drug from being altered while passing through a hostile environment, such as the digestive tract. Prodrugs can be prepared by forming covalent linkages between the drug and a modifier. See, for example, Balant at al., Eur. J. Drug Metab. Phannacokinetics, 1990, 15(2), 143–153. The linkage is usually designed to be broken under defined circumstances, e.g., pH changes or exposure to specific enzymes. The covalent linkage of the drug to a modifier essentially creates a new molecule with new properties such as an altered log P value and/or as well as a new spatial configuration. The new molecule can have different solubility properties and be less susceptible to enzymatic digestion. For general references on prodrug design and preparation, see: Bundraard, Design of Prodrugs, Elsevier Science Pub. Co., N.Y. (1985), and Prodrugs as Novel Drug Delivery Systems Symposium, 168.sup.th Annual Meeting, American Chemical Society, Atlantic City, N.J., Eds. T. Higuchi and V. Stella, ACS Symposium Series 14, 1975, which are herein incorporated by reference.

Prodrugs of arnine-containing compounds are well known in the art and have been prepared, e.g., by reacting the amine moiety of a drug with a carboxylic acid, acid chloride, chloroforrnate, or sulfonyl chloride modifiers, and the like, resulting in the formation of amnides, sulfonarnides, carboxyamides, carbamates, and similar compounds. See, for example, Abuchowski et al., J. Biol. Chem. 1977, 252, 3578–358; Senter et al., J. Org. Chem., 1990, 55, 2975–2978; Amsberry et al., J. Org. Chem., 1990, 55, 5867–5877; Klotz, Clin. Pharmacokinetics, 1985, 10, 285–302, which are herein incorporated by reference. Similar and other protocols may be followed for the formation of prodrugs of the compounds of the present invention.

The compounds of the present invention, particularly libraries of amphetamine analogs having various representative classes of substituents, are amenable to combinatorial chemistry and other parallel synthesis schemes (see, for example, PCT WO 94/08051). The result is that large libraries of related compounds, e.g., a variegated library of compounds represented above, can be screened rapidly in high throughput assays in order to identify potential amphetamine analogs, as well as to refine the specificity, toxicity, and/or cytotoxic-kinetic profile of a lead compound.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject amphetamine compounds. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. No. 5,736,412 and 5,712,171; Chen et al. (1994) *JACS* 116:2661: Kerr et al. (1993) *JACS* 115:252; PCT publications WO92/10092, WO93/09668 and WO91/07087; and the Lemer et al. PCT publication WO93/20242). Accordingly, a variety of libraries on the order of about 100 to 1,000,000 or more diversomers of the subject amphetamine compounds can be synthesized and screened for particular activity or property.

In an exemplary embodiment, a library of candidate amphetamine compound diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate regulators or a substituent of a synthetic intermediate. According to the Still et al. technique, the library is synthesized on a set of beads, each bead including a set of tags identifying the particular diversomer on that bead. The bead library can then be "plated" with cells for which an amphetamine compound is sought. The diversomers can be released from the bead, e.g., by hydrolysis.

Many variations on the above and related pathways permit the synthesis of widely diverse libraries of compounds which may be tested as amphetamine compounds.

B. Generation of Animal Models to Test Agents

Applicants have previously described an animal model for studying fornix-mediated memory consolidation. See, for example, Taubenfield et al., Supra. The fornix-lesioned animals can be used for drug screening, e.g., to identify dosages of the subject compositions which enhance memory consolidation. The lesioned mammal can have a lesion of the fornix or a related brain structure that disrupts memory consolidation (e.g., perirhinal cortex, amygdala, media septal nucleus, locus coeruleus, hippocarnpus, mammallary bodies). Lesions in the mammal can be produced by mechanical or chemical disruption. For example, the fornix lesion can be caused by surgical ablation, electrolytic, neurotoxic and other chemical ablation techniques, or reversible inactivation such as by injection of an anesthetic, e.g., tetrodotoxin or lidocaine, to temporarily arrest activity in the fornix.

To further illustrate, fimbrio-fornix (rodents) and fornix (primates) lesions can be created by stereotactic ablation. In particular, neurons of the fomix structure are axotomized, e.g., by transection or aspiration (suction) ablation. A complete transection of the fornix disrupts adrenergic, cholinergic and GABAergic function and electrical activity, and induces morphological reorganization in the hippocampal formation. In general, the fomix transection utilized in the subject method will not disconnect the parahippocampal region from the neocortex. In those embodiments, the fomix transection will not disrupt functions that can be carried out by the parahippocampal region independent of processing by the hippocampal formation, and hence would not be expected to produce the full-blown amnesia seen following more complete hippocampal system damage.

In one embodiment, the animal can be a rat. Briefly, the animals are anesthetized, e.g., with intraperitoneal injections of a ketamine-xylazine mixture and positioned in a Kopf stereotaxic instrument. A sagittal incision is made in the scalp and a craniotomy is performed extending 2.0 mm posterior and 3.0 mm lateral from Bregma. An aspirative device, e.g., with a 20 gauge tip, is mounted to a stereotaxic frame (Kopf Instruments) and fimbria-fomix is aspirated by placing the suction tip at the correct sterotaxic location in the animal's brain. Unilateral aspirative lesions are made by suction through the cingulate cortex, completely transecting the fimbria fomix unilaterally, and (optionally) removing the dorsal tip of the hippocampus as well as the overlying cingulate cortex to inflict a partial denervation on the hippocampus target. See also, Gage et al., (1983) Brain Res. 268:27 and Gage et al. (1986) Neuroscience 19:241.

In another exemplary embodiment, the animal can be a monkey. The animal can be anesthetized, e.g., with isoflurane (1.5–2.0%). Following pretreatment with mannitol (0.25 glkg, iv), unilateral transections of the left fomix can be performed, such as described by Kordower et al. (1990) J. Comp. Neurol., 298:443. Briefly, a surgical drill is used to create a parasagittal bone flap which exposes the frontal superior sagittal sinus. The dura is retracted and a self-retaining retractor is used to expose the interhemispheric fissure. The corpus callosum is longitudinally incised. At the level of the foramen of Monro, the fornix is easily visualized as a discrete 2–3 mm wide white fiber bundle. The fornix can be initially transected using a ball dissector. The cut ends of the fornix can then be suctioned to ensure completeness of the lesion.

In still other illustrative embodiments, the fornix lesion can be created by excitotoxically, or by other chemical means, inhibiting or ablating fornix neurons, or the cells of the hippocampus which are innervated by fomix neurons. In certain preferred embodiments, the fornix lesion is generated by selective disruption of particular neuronal types, such as fornix cholinergic and adrenergic neurons.

For instance, the afferant fornix signals to the hippocampus due to cholinergic neurons can be ablated by atropine blockade. Another means for ablation of the cholinergic neurons is the use of 192IgG-saporin (192IgG-sap), e.g., intraventricularly injection into the fornix and hippocampus. The agents such as 6-OHDA and ibotenic acid can be used to selectively destroy fornix dopamine neurons as part of the ablative regimen.

In preferred embodiments, the animal is a non-human mammal, such as a dog, cat, horse, cow, pig, sheep, goat, chicken, monkey, ape, rat, rabbit, etc. In certain preferred embodiments, the animal is a non-human primate. In other preferred embodiment, the animal is a rodent.

There are a variety of tests for cognitive function, especially learning and memory testing, which can be carried our using the lesioned and normal animals. Learning and/or memory tests include, for example, inhibitory avoidance, contextual fear conditioning, visual delay non-match to sample, spatial delay non-match to sample, visual discrimination, Barnes circular maze, Morris water maze, radial arm maze tests, Ray Auditory-Visual Learning Test, the Wechsler Logical Memory Test, and the Providence Recognition Memory Test.

An exemplary passive avoidance test utilizes an apparatus that consists of a lit chamber that can be separated from a dark chamber by a sliding door. At training, the animal is placed in the lit chamber for some period of time, and the door is opened. The animal moves to the dark chamber after a short delay—the latency—that is recorded. Upon entry into the dark chamber, the door is shut closed and a foot shock is delivered. Retention of the experience is determined after various time intervals, e.g., 24 or 48 hours, by repeating the test and recording the latency. The protocol is one of many variants of the passive avoidance procedures (for review, see Rush (1988) Behav. Neural. Biol. 50:255).

An exemplary maze testing embodiment is the water maze working memory test, In general, the method utilizes an apparatus which consists of a circular water tank. The water in the tank is made cloudy by the addition of milk powder. A clear plexiglass platform, supported by a movable stand rest on the bottom of the tank, is submerged just below the water surface. Normally, a swimming rat cannot perceive the location of the platform but it may recall it from a previous experience and training, unless it suffers from some memory impairment. The time taken to locate the platform is measured and referred to as the latency. During the experiment, all orientational cues such as ceiling lights, etc., remain unchanged. Longer latencies are generally observed with rats with some impairment to their memory.

Another memory test includes the eyeblink conditioning test, which involves the administration of white noise or steady tone that precedes a mild air puff which stimulates the subject's eyeblink.

Still another memory test which can be used is fear conditioning, e.g., either "cued" and "contextual" fear conditioning. In one embodiment, a freeze monitor administers a sequence of stimuli (sounds, shock) and then records a series of latencies measuring the recovery from shock induced freezing of the animal.

Another memory test for the lesioned animals is a holeboard test, which utilizes a rotating holeboard apparatus containing (four) open holes arranged in a 4-corner configuration in the floor of the test enclosure. A mouse is trained to poke its head into a hole and retrieve a food reward from a "baited" hole which contains a reward on every trial. There is a food reward (e.g., a Froot Loop) in every exposed hole which is made inaccessible by being placed under a screen. The screen allows the odor of the reward to emanate from the hole, but does not allow access to the reinforcer. When an individual hole is baited, a reward is placed on top of the screen, where it is accessible. The entire apparatus rests on a turntable so that it may be rotated easily to eliminate reliance on proximal (e.g., olfactory) cues. A start tube is placed in the center of the apparatus. The subject is released from the tube and allowed to explore for the baited ("correct") hole.

As set out above, one use for the fornix-lesioned animals is for testing amphetamine compounds for ability to modulate memory consolidation, as well as for side effects and toxicity. In general, the subject method utilizes an animal which has been manipulated to create at least partial disruption of fomix-mediated signalling to the hippocampus, the disruption affecting memory consolidation and learned behavior in the animal. The animal is conditioned with a learning or memory regimen which results in learned behavior in the mammal in the absence of the fornix lesion. Amphetamine compounds are administered to the animal in order to assess their effects on memory consolidation. An increase in learned behavior, relative to the absence of the test agents, indicates that the administered combination enhances memory consolidation.

Another memory test especially developed for use in pharmaceutical studies is the Providence Recognition Memory Test This test consists of one pictorial and one verbal assessment of long-term declarative memory. In each of the two modes, the patient views stimuli on a computer screen and is later asked to recognize those stimuli in a two-alternative forced-choice format. The pictorial assessment mode consists of two parts: a study phase and a recognition phase. In the study phase, patients view a series of 120 pictures, for 3 seconds each. They are told to look at the pictures and remember them, so that they can recognize them later. In the recognition phase, patients view pictures two at a time and are asked to indicate by button press which of the two pictures they saw in a study phase. Recognition memory testing occurs at ten minutes, one hour, and 24 hours after the end of the study phase. The verbal assessment mode consists of two parts: a study phase and a recognition phase. In the study phase, patients view a series of 60 sentences one at a time. They are asked to read the sentences aloud and remember them, so that they can recognize them later. Each sentence remains on the computer screen until the patient has finished reading it aloud. If patients read words incorrectly, the examiner supplies the correct word or words. In the recognition phase, patients view sentences two at a time and are asked to indicate by button press which of the two sentences they saw in the study phase. Recognition memory testing occurs at ten minutes, one hour, and 24 hours after the end of the study phase.

In the methods of the present invention, retention of the learned behavior can be determined, for example, after at least about 12–24 hours, 14–22 hours, 16–20 hours and or 18–19 hours after completion of the learning phase to determine whether the agents promote memory consolidation. In a particular embodiment, retention of the learned behavior can be determined 24 hours after completion of the learning phase.

In addition to models for studying memory consolidation, models to assess side effects of amphetamine compounds on behavior have been utilized including locomotor activity models. An exemplary locomotor activity test utilizes an apparatus that consists of photocell activity cages with a wire grid base in which the photocell beam is placed. The animals are placed in individual activity cages some period of time prior to administration of agents. Locomotor activity is measured by the number of interruptions of the photoelectric beam during An maximum locomotor activity corresponds to a maximum number of interruptions of the light beam.

As used herein, a "control mammal" can be an untreated lesion mammal (i.e., a lesion animal receiving no agents or not the same combinations to be assessed), a trained control mammal (i.e., a mammal that undergoes training to demonstrate a learned behavior without any lesion) and/or an untrained control mammal (i.e., a mammal with or without a lesion, that receives no training to demonstrate a learned behavior).

C. Pharmaceutical Preparations of Amphetamine Compounds

In another aspect, the present invention provides pharmaceutical preparations comprising the subject amphetamine compounds. The amphetamine compounds for use in the subject method may be conveniently formulated for administration with a biologically acceptable, non-pyrogenic, and/or sterile medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to behavioral scientists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the amphetamine compounds, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the amphetamine compounds suitable for veterinary uses, e.g., for the treatment of livestock or domestic animals, e.g., dogs.

Methods of introduction may also be provided by rechargeable or biodegradable devices. Various slow release polymeric devices have been developed and tested in vivo in recent years for the controlled delivery of drugs. A variety of biocompatible polymers (including hydrogels), including both biodegradable and non-degradable polymers, can be used to form an implant for the sustained release of a amphetamine compound at a particular target site.

The preparations of the present invention may be given orally, parenterally, topically, or rectally. They are of course given by forms suitable for each administration route. For example, they are administered in tablets or capsule form, by injection, infusion, inhalation, eye lotion, ointment, rectal suppository, or controlled release patch. Oral and controlled release patch administrations are preferred.

In certain preferred embodiments, the subject therapeutic is delivered by way of a transdermal patch. A patch is generally a flat hollow device with a permeable membrane on one side and also some form of adhesive to maintain the patch in place on the patient's skin, with the membrane in contact with the skin so that the medication can permeate out of the patch reservoir and into and through the skin. The outer side the patch is formed of an impermeable layer of material, and the membrane side and the outer side are joined around the perimeter of the patch, forming a reservoir for the medication and carrier between the two layers.

Patch technology is based on the ability to hold an active ingredient in constant contact with the epidermis. Over substantial periods of time, drug molecules, held in such a state, will eventually find their way into the bloodstream. Thus, patch technology relies on the ability of the human body to pick up drug molecules through the skin. Transdermal drug delivery using patch technology has recently been applied for delivery of nicotine, in an effort to assist smokers in quitting, the delivery of nitroglycerine to angina sufferers, the delivery of replacement hormones in post menopausal women, etc. These conventional drug delivery systems comprise a patch with an active ingredient such as a drug incorporated therein, the patch also including an adhesive for attachment to the skin so as to place the active ingredient in close proximity to the skin. Exemplary patch technologies are available from Ciba-Geigy Corporation and Alza Corporation. Such transdermal delivery devices can be readily adapted for use with the subject amphetamine compounds.

The flux of the subject amphetamines across the skin can be modulated by changing either (a) the resistance (the diffusion coefficient), or (b) the driving force (the solubility of the drug in the stratum corneum and consequently the gradient for diffusion). Various methods can be used to increase skin permeation by the subject amphetamines, including penetration enhancers, use of pro-drug versions, superfluous vehicles, iontophoresis, phonophoresis and thermophoresis. Many enhancer compositions have been developed to change one or both of these factors. See, for example, U.S. Pat. Nos. 4,006,218; 3,551,154; and 3,472,931, for example, respectively describe the use of dimethylsulfoxide (DMSO), dimethyl formamide (DMF), and N,N-dimethylacetamide (DMA) for enhancing the absorption of topically applied drugs through the stratum corneum. Combinations of enhancers consisting of diethylene glycol monoethyl or monomethyl ether with propylene glycol monolaurate and methyl laurate are disclosed in U.S. Pat. No. 4,973,468. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of C2 to C4 alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a C2 or C3 alkanol; and an inert diluent such as water. Other examples are included in the teachings of U.S. Pat. No. 4,933,184 which discloses the use of menthol as a penetration enhancer; U.S. Pat. No. ,229,130 discloses the use of vegetable oil (soybean and/or coconut oil) as a penetration enhancer; and U.S. Pat. No. 4,440,777 discloses the use of eucalyptol as a penetration enhancer.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular amphetamine compounds employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic iL effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one is not entirely disappeared when the subsequent is administered.

While it is possible for a compound of the present invention to be administered alone, it is preferable to administer the compound as a pharmaceutical formulation (composition). The amphetamine compounds according to the invention may be formulated for administration in any convenient way for use in human or veterinary medicine.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid forr, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water.

The phrase "pharmaceutically acceptable carrier" as used herein means a pharmaceutically acceptable rnaterial, composition or vehicle, such as a liquid or solid filter, diluent, excipient, solvent or encapsulating material, involved in carrying or transporting the subject regulators from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as cthyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present amphetamine compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention; or by separately reacting a purified compound of the invention in its free base form with a suitable organic or inorganic acid, and isolating the salt thus formed. Representative salts include but are not limited to following: 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, finnarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphateldiphosphate, picrate, pivalate, polygalacturonate, propionate, p-toluenesulfonate, salicylate, stearate, subacetate, succinate, sulfate, sulfosaliculate, suramate, tannate, tartrate, teoclate, thiocyanate, tosylate, triethiodide, undecanoate, and valerate salts, and the like. (See, for example, Berge et al. (1977) "Pharmaceutical Salts", *J Pharm. Sci.* 66:1–19)

In certain embodiments, the pharmaceutically acceptable salts of the subject compounds include the conventional non-toxic salts of the compounds, e.g., from non-toxic organic or inorganic acids. Particularly suitable are salts of weak acids. For example, such conventional non-toxic salts include those derived from inorganic acids such as hydrochloric, hydrobromic, hydriodic, cinnamic, gluconic, suliric, sulfamnic, phosphoric, nitric, and the like; and the salts prepared from organic acids such as acetic, propionic, succinic, glycolic, stearic, lactic, maleic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediarnine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxyrnethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymnethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharrnaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active amphetamine compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

In certain embodiments, the subject compound(s) are formulated as part of a transdermal patch. Transdermal patches have the added advantage of providing controlled delivery of a compound of the present invention to the body. Such dosage forms can be made by dissolving or dispersing the amphetamine compounds in the proper medium. Absorption enhancers can also be used to increase the flux of the amphetamine compounds across the skin. The rate of such flux can be controlled by either providing a rate-controlling membrane or dispersing the compound in a polymer matrix or gel.

The "free base form" of amphetamine relates to a form in which amphetamine is not complexed with an acid, e.g., is not an ammonium salt. Such forms may be incorporated into a patch. It will be appreciated that the amphetamine compounds may be complexed, for example, with elements of the drug-retaining matrix of the patch and, as such, the amphetamine compounds may not necessarily be in the form of the free base, when actually retained by the patch.

The patch preferably comprises a drug-impenneable backing layer. Suitable examples of drug-impermeable backing layers which may be used for transdermal or medicated patches include films or sheets of polyolefins, polyesters, polyurethanes, polyvinyl alcohols, polyvinyl chlorides, polyvinylidene chloride, polyamides, ethylene-vinyl acetate copolymer (EVA), ethylene-ethylacrylate copolymer (EEA), vinyl acetate-vinyl chloride copolymer, cellulose acetate, ethyl cellulose, metal vapour deposited films or sheets thereof, rubber sheets or films, expanded. synthetic resin sheets or films, non-woven fabrics, fabrics, knitted fabrics, paper and foils. Preferred drug-impermeable, elastic backing materials are selected from polyethylene tereplithalate (PET), polyurethane, ethylene-vinyl acetate copolymer (EVA), plasticised polyvinylchloride, woven and non-woven fabric. Especially preferred is non-woven poly-ethylenetereplithalate (PET). Other backings will be readily apparent to those skilled in the art.

The term 'block copolymer', in the preferred adhesives of the invention, refers to a macromolecule comprised of two or more chemically dissimilar polymer structures, terminally connected together (Block Copolymers: Overview and Critical Survey, Noshay and McGrath, 1977). These dissimilar polymer structures, sections or segments, represent the 'blocks' of the block copolymer. The blocks may generally be arranged in an A—B structure, an A—B—A structure, or a multi-block —(A—B)$_n$— system, wherein A and B are the chemically distinct polymer segments of the block copolymer.

It is generally preferred that the block copolymer is of an A—B—A structure, especially wherein one of A and B is an acrylic-type polymeric unit. It will be appreciated that the present invention is also applicable using block copolymers which possess three or more different blocks, such as an A—B—C block copolymer. However, for convenience, reference hereinafter to block copolymers will assume that there are only A and B sub-units, but it will be appreciated that such reference also encompasses block copolymers having more than two different sub-units, unless otherwise specified.

It will be appreciated that the properties of block copolymers are very largely determined by the nature of the A and B blocks. Block copolymers commonly possess both 'hard' and 'soft' segments. A 'hard' segment is a polymer that has a glass transition temperature (Tg) and/or a melting temperature (Tm) that is above room temperature, while a 'soft' segment is a polymer that has a Tg (and possibly a Tm) below room temperature. The different segments are thought to impart different properties to the block copolymer. Without being constrained by theory, it is thought that association of the hard segments of separate block copolymer units result in physical cross-links within the block copolymer, thereby promoting cohesive properties of the block copolymer. It is particularly preferred that the hard segments of the block copolymers form such physical close associations.

The block copolymers useful in the present invention preferably are acrylic block copolymers. In acrylic block copolymers, at least one of the blocks of the block copolymer is an acrylic acid polymer, or a polymer of an acrylic acid derivative. The polymer may be composed of just one repeated monomer species. However, it will be appreciated that a mixture of monomeric species may be used to form each of the blocks, so that a block may, in itself, be a copolymer. The use of a combination of different monomers can affect various properties of the resulting block copolymer. In particular, variation in the ratio or nature of the monomers used allows properties such as adhesion, tack and cohesion to be modulated, so that it is generally advantageous for the soft segments of the block copolymer to be composed of more than one monomer species.

It is preferred that alkyl acrylates and alkyl methacrylates are polymerized to form the soft portion of the block copolymer. Alkyl acrylates and alkyl methacrylates are thought to provide properties of tack and adhesion. Suitable alkyl acrylates and alkyl methacrylates include n-butyl acrylate, n-butyl methacrylate, hexyl acrylate, 2ethylbutyl acrylate, isooctyl acrylate, 2-ethylhexyl acrylate, 2-ethylhexyl methacrylate, decyl acrylate, decyl methacrylate, dodecyl acrylate, dodecyl methacrylate, tridecylacrylate and tridecyl methacrylate, although other suitable acrylates and methacrylates will be readily apparent to those skilled in the art. It is preferred that the acrylic block copolymer comprises at least 50% by weight of alkyl acrylate or alkyl methacrylate(co)polymer.

Variation in the components of the soft segment affects the overall properties of the block copolymer, although the essential feature remains the cross-linking of the soft segments. For example, soft segments essentially consisting of diacetone acrylamide with either butyl acrylate and/or 2-ethylhexyl acrylate, in approximately equal proportions, work well, and a ratio by weight of about 3:4:4 provides good results. It is preferred that diacetone acrylamide, or other polar monomer, such as hydroxyethylmethacrylate or vinyl acetate, be present in no more than 50% w/w of the monomeric mix of the soft segment, as this can lead to reduced adhesion, for example. The acrylate component may generally be varied more freely, with good results observed with both2-ethylhexyl acrylate and butyl acrylate together or individually.

As noted above, ratios of the various monomers are generally preferred to be approximately equal. For adhesives, this is preferred to be with a polar component of 50% or less of the soft segment, with the apolar portion forming up to about 85% w/w, but preferably between about 50 and 70% w/w. In the example above, this is about 72% (4+4) a polar to about 18% (3) polar.

In general, it is particularly preferred that any apolar monomer used does not confer acidity on the adhesive. Adhesives of the invention are preferably essentially neutral, and this avoids any unnecessary degeneration of the amphetamine compounds.

Limiting active functionalities, especially those with active hydrogen, is generally preferred, in order to permit wide use of any given formulation of adhesive without having to take into account how it is likely to interact, chemically, with its environment. Thus, a generally chemically inert adhesive is preferred, in the absence of requirements to the contrary.

As discussed above, polymers suitable for use as the hard. portion of the block copolymer possess glass transition temperatures above room temperature. Suitable monomers for use in forming the hard segment polymer include styrene,(x-methylstyrene, methyl methacrylate and vinyl pyrrolidone, although other suitable monomers will be readily apparent to those skilled in the art. Styrene and polymethylmethacrylate have been found to be suitable for use in the formation of the hard segment of the block copolymers. It is preferred that the hard portion of the block copolymer forms from 3–30% w/w of the total block copolymer, particularly preferably from 5–15% w/w.

The block copolymer is further characterized in that the soft portions contain a degree of chemical cross-linking. Such cross-linking may be effected by any suitable cross-linking agent. It is particularly preferable that the cross-linking agent be in the form of a monomer suitable for incorporation into the soft segment during polymerization. Preferably the cross-linking agent has two, or more, radically polymerizable groups, such as a vinyl group, per molecule of the monomer, at least one tending to remain unchanged during the initial polymerization, thereby to permit cross-linking of the resulting block copolymer.

Suitable cross-linking agents for use in the present invention include divinylbenzene, methylene bis-acrylamide, ethylene glycol di(meth)acrylate, ethyleneglycol tetra(meth)acrylate, propylene glycol di(meth)acrylate, butylene glycoldi(meth)acrylate, or trimethylolpropane tri(meth)acrylate, although other suitable cross-linking agents will be readily apparent to those skilled in the art. A preferred cross-linking agent is tetraethylene glycol dimethacrylate. It is preferred that the cross-linking agent comprises about 0.01–0.6% by weight of the block copolymer, with 0.1–0.4% by weight being particularly preferred.

Methods for the production of block copolymers from their monomeric constituents are well known. The block copolymer portions of the present invention may be produced by any suitable method, such as step growth, anionic, cationic and free radical methods (Block Copolymers, supra). Free radical methods are generally preferred over other methods, such as anionic polymerization, as the solvent and the monomer do not have to be purified.

Suitable initiators for polymerization include polymeric peroxides with more than one peroxide moiety per molecule. An appropriate choice of reaction conditions is well within the skill of one in the art, once a suitable initiator has been chosen.

The initiator is preferably used in an amount of 0.005–0.1% by weight of the block copolymer, with 0.01–0.05% by weight being particularly preferred, although it will be appreciated that the amount chosen is, again, well within the skill of one in the art. In particular, it is preferred that the amount should not be so much as to cause instant gelling of the mix, nor so low as to slow down polymerization and to leave excess residual monomers. A preferred level of residual monomers is below 2000 ppm.

It will also be appreciated that the amount of initiator will vary substantially, depending on such considerations as the initiator itself and the nature of the monomers.

The block copolymers are adhesives, and preferably are pressure sensitive adhesives. Pressure sensitive adhesives can be applied to a surface by hand pressure and require no activation by heat, water or solvent. As such, they are particularly suitable for use in accordance with the present invention.

The block copolymers may be used without tackifiers and, as such, are particularly advantageous. However, it will be appreciated that the block copolymers may also be used in combination with a tackifier, to provide improved tack, should one be required or desired. Suitable tackifiers are well known and will be readily apparent to those skilled in the art.

Without being constrained by theory, it is thought that the combination of chemical cross-links between the soft segments of the copolymer combined with the, generally, hydrophobic interaction, or physical cross-linking, between the hard portions results in a "matrix-like" structure. Copolymers having only physical cross-linking of the hard segments are less able to form such a matrix. It is believed that the combination of both forms of cross-linking of the block copolymers provides good internal strength (cohesion) and also high drug storage capacity.

More particularly, it is believed that the hard segments associate to form "islands", or nodes, with the soft segments radiating from and between these nodes.

There is a defined physical structure in the "sea" between the islands, where the soft segments are cross-linked, so that there is no necessity for extensive intermingling of the soft segments. This results in a greater cohesion of the whole block copolymer while, at the same time, allowing shortened soft segment length and still having as great, or greater, distances between the islands, thereby permitting good drug storage capacity.

The block copolymer preferably cross-links as the solvent is removed, so that cross-linking can be timed to occur after coating, this being the preferred method.

Accordingly, not only can the block copolymer easily be coated onto a surface, but the complete solution can also be stored for a period before coating. Accordingly, in the manufacturing process of the patches, the process preferably comprises polymerizing the monomeric constituents of each soft segment in solution, then adding the constituents of the hard segment to each resulting solution and polymerizing the resulting mix, followed by cross-linking by removal of any solvent or solvent system, such as by evaporation. If the solution is to be stored for any length of time, it may be necessary to keep the polymer from precipitating out, and this may be achieved by known means, such as by suspending agents or shaking. It may also be necessary to select the type of polymers that will be subject to substantially no cross-linking until the solvent is evaporated.

In general, it is preferred that the adhesive possesses a minimum number of functionalities having active hydrogen, in order to avoid undesirable reactions/interactions, such as with any drug that it is desired to incorporate into the adhesive material. It will be appreciated that this is only a preferred restriction, and that any adhesive may be tailored by one skilled in the art to suit individual requirements.

Suitable monomers for use in forming the hard segment include styrene, a-methy styrene, methyl methacrylate and vinyl pyrrolidone, with the preferred proportion of the hard segment being between 5 and 15 percent w/w. In particular, it is advantageous to use the compounds of WO 99/02141, as it is possible to load over 30 percent of drug into such a system.

Thus, in the patches of the present invention, it is generally possible to calculate the amount of drug required and determine the appropriate patch size with a given drug loading in accordance with a patient's body weight, and this can be readily calculated by those skilled in the art.

In certain embodiments, small amounts of plasticizer, such as isopropyl myristate (IPM), are incorporated. This has the advantage of helping to solubilize the amphetamine as well as rendering the adhesive less rough on the skin. Levels of between 2 and 25%, by weight, are generally useful, with levels of between 3 and 20% being more preferred and levels of 5 to 15%, especially about 10%, being most preferred. Other plasticizers may also be used, and suitable plasticizers will be readily apparent to those skilled in the art.

Plasticizers generally take the form of oily substances introduced into the adhesive polymer. The effect of the introduction of such oily substances is to soften the physical structure of the adhesive whilst, at the same time, acting at the interface between the adhesive and the skin, thereby helping to somewhat weaken the adhesive, and to reduce exfoliation.

The free base oil may be obtained by basifying amphetamine salts, or any other suitable salt, with a suitable base, in the presence of a hydrophilic solvent, especially water, and an organic solvent. For instance, water and ethyl acetate, in approximately equal proportions, work well, with ammonia serving as the basifying agent. The water may then be removed and the preparation washed with further water, or other aqueous preparation, after which the preparation may be suitably extracted with ether, for example, after having removed the ethyl acetate. It is preferred to keep the preparation under an inert atmosphere, especially after completion.

Whilst it will be appreciated that patches of the present invention may be removed from the patient at any time, once it is desired to terminate a given dose, this can have the disadvantage of providing an opportunity for potential drug abuse of the partially discharged patch. Abuse of amphetamines is highly undesirable.

In certain embodiments, it may be advantage to use a patch tailored to have delivered the majority of the amphetamine that it is capable of delivering, in a 24 hour period, by about 8 hours after application, so that a patch can be left in place, and levels of drug still diminish appreciably. It is advantageous that the drug delivery profile has first order kinetics, so that the majority of the drug is delivered during the main part of the day and, even if the patient omits to remove the patch, the drug is moving towards exhaustion by the end of the day, and the amount of drug is dropping rapidly.

It will be appreciated that patches of the invention may be constructed in any suitable manner known in the art for the manufacture of transdermal patches. The patches may simply comprise adhesive, drug and backing, or may be more complex, such as having edging to prevent seepage of drug out of the sides of the patch. Patches may also be multi-layered.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active cornpound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and Co., San Francisco, U.S.A., 1969 or "Livestock Feeds and Feeding" O and B books, Corvallis, Oreg., U.S.A., 1977).

IV. Exemplary Uses of the Compounds of the Invention.

In various embodiments, the present invention contemplates modes of treatment and prophylaxis which utilize one or more of the subject amphetamine compounds. These agents may be useful for increasing the occurrence of memory consolidation (LTP) or decreasing or preventing the effects of defects in an animal which mitigate memory consolidation. In other embodiments, the preparations of the present invention can be used simply to enhance normal memory function.

In certain embodiments, the subject method can be used to treat patients who have been diagnosed as having or at risk of developing disorders in which diminished declarative memory is a symptom, e.g., as opposed to procedural memory. The subject method can also be used to treat normal individuals for whom improved declarative memory is desired.

Memory disorders which can be treated according to the present invention may have a number of origins: a functional mechanism (anxiety, depression), physiological aging (age-associated memory impairment, mild cognitive impairment, etc.), drugs, or anatomical lesions (dementia). Indications for which such preparations may be useful include learning disabilities, memory impairment, e.g., due to toxicant exposure, brain injury, brain aneurysm, age, schizophrenia, epilepsy, mental retardation in children, and senile dementia, including Alzheimer's disease.

Although in certain embodiments, attention deficit disorder (ADD), attention deficit hyperactivity disorder (ADHD), and AIDS-related dementia may respond to treatment with a subject compound, in certain embodiments, the patient's memory loss is not associated with one of these conditions.

An attention-deficit disorder (ADD) is a developmental disorder characterized by developmentally inappropriate degrees of inattention, overactivity, and impulsivity. Symptoms are neurologically based, arise in early childhood, and are chronic in nature in most cases. Symptoms are not due to gross neurological impairment, sensory impairment, language or motor impairment, mental retardation, or emotional disturbance.

ADD with and without hyperactivity are separate and unique childhood disorders. They are not subtypes of an identical attention disturbance. It has been noted that children with ADD/-H are more frequently described as depressed, learning disabled, or "lazy" while children with ADD/+H are more frequently labeled as conduct or behavior disordered.

Characteristics of ADHD have been demonstrated to arise in early childhood for most individuals. This disorder is marked by chronic behaviors lasting at least six months with an onset often before seven years of age. At this time, four subtypes of ADHD have been defined. These include the following:

1. ADHD—Inattentive type
2. ADHD—hyperactive/impulsive type
3. ADHD—combined type
4. ADHD—not otherwise specified is defined by an individual who demonstrates some characteristics but an insufficient number of symptoms to reach a full diagnosis. These symptoms, however, disrupt everyday life.

The American Psychiatric Association Diagnostic and Statistical Manual (DSM-IV) criteria for diagnosing ADHD include:

A. Either (1) or (2)
   (1). six (or more) of the following symptoms of inattention have persisted for at least 6 months to a degree that is maladaptive and inconsistent with developmental level:

Inattention
   (a) often fails to give close attention to details or makes careless mistakes in schoolwork, work, or other activities
   (b) often has difficulty sustaining attention in tasks or play activities
   (c) often does not seem to listen when spoken to directly
   (d) often does not follow through on instructions and fails to finish schoolwork, chores, or duties in the workplace (not due to oppositional behavior or failure to understand instructions)
   (e) often has difficulty organizing tasks and activities (f) often avoids, dislikes, or is reluctant to engage in tasks that require sustained mental effort (such as schoolwork or homework).
(g) often loses things necessary for tasks or activities (e.g. toys, school assignments, pencils, books, or tools)
(h) is often easily distracted by extraneous stimuli
(i) is often forgetful in daily activities (2). six (or more) of the following symptoms of hyperactivity-impulsivity have persisted for at least 6 months to a degree that is maladaptive and inconsistent with developmental level Hyperactivity
(a) often fidgets with hands or feet or squirms in seat
(b) often leaves seat in classroom or in other situations in which remaining seated is expected
(c) often runs about or climbs excessively in situations in which it is inappropriate (in adolescents or adults, may be limited to subjective feelings of restlessness)
(d) often has difficulty playing or engaging in leisure activities quietly
(e) is often "on the go" or often acts as if "driven by a motor"
(f) often talks excessively Impulsivity
(g) often blurts out answers before questions have been completed
(h) often has difficulty awaiting turn
(i) often interrupts or intrudes on others (e.g. butts into conversations or games)

B. Some hyperactive-impulsive or inattentive symptoms that caused impairment were present before age 7 years.
C. Some impairment from the symptoms is present in two or more settings (e.g. at school [or work] and at home).
D. There must be clear evidence of clinically significant impairment in social, academic, or occupational functioning. E. The symptoms do not occur exclusively during the course of a Pervasive Developmental Disorder, Schizophrenia, or other Psychotic Disorder and are not better accounted for by another mental disorder (e.g., Mood Disorder, Anxiety Disorder, Dissociative Disorder, or a Personality Disorder)

One aspect of the present invention relates to the combination of amphetamine (or analog metabolic derivative thereof) and a dopamine reuptake inhibitor. A variety of dopamine transporter inhibitors (also called dopamine uptake inhibitors; herein referred to as active compounds) of diverse structure are known. See, e.g., S. Berger, U.S. Pat. No. 5,217,987; J. Boja et al., Molec. Pharmacol. 47, 779–786 (1995); C. Xu et al., Biochem. Pharmacol. 49, 339–50 (1995); B. Madras et al., Eur. J. Pharmacol. 267, 167–73 (1994); F. Carroll et al., 3. Med. Chem. 37, 2865–73 (1994); A. Eshleman et al., Molec. Pharmacol. 45, 312–16 (1994); R. Heikkila and L. Manzino, Eur. J. Pharmacol. 103, 241-8 (1984). Dopamine transporter inhibitors are, in general, ligands that bind in a stereospecific manner to the dopamine transporter protein. Examples of such compounds are:

(1) tricyclic antidepressants such as buprion, nomifensine, and amineptin;
(2) 1,4disubstituted piperazines, or piperazine analogs, such as 1-[2-[bis(4-fluorophenyl)methoxy]ethyl]-4(3-phenylpropyl)piperazine dihydrochloride (or GBR 12909), 1-[2-[bis(phenyl) methoxy]ethyl]-4-(3-phenylpropyl)piperazine dihydrochloride (for $GBR_{12934}$), and $GBR_{13069}$;
(3) tropane analogs, or (disubstituted phenyl) tropane-2 beta-carboxylic acid methyl esters, such as 3 [beta]-(4-fluorophenyl) tropane-2 [beta]-carboxylic acid methyl ester (or WIN 35,428) and 3 [beta]-(4-iodophenyl) tropane-2 [beta]-carboxylic acid isopropyl ester (RTI-121);
(4) substituted piperidines, or piperidine analogs, such as N-[1-(2-benzo[b]-thiophenyl)cyclohexyl]piperidine, indatraline, and 4[2-[bis(4 fluorophenyl)methoxy] ethyl]-1-(3-phenylpropyl)piperidine (or O-526);
(5) quinoxaline derivatives, or quinoxaline analogs, such as 7-trifluoromethyl-4-(4-methyl-1-piperazinyl) pyrrolo[1,2-[alpha]]-quinoxaline (or CGS 12066b); and
(6) other compounds that are inhibitors of dopamine reuptake, such as mazindol, benztropine, bupropion, phencyclidine, methylphenidate, etc.

Accordingly, certain embodiments of the invention relates to a method for treating ADHD (adult or child), comprising co-administering (e.g., simultaneously or at different times) to the patient (human or other animal) an amount of an amphetamine (or analog or metabolite thereof) sufficient to treat the attention component of ADHD, and an amount of a dopamine reuptake inhibitor sufficient to treat the movement disorder component. In certain embodiments, the amphetamine and the dopamine reuptake inhibitor are administered simultaneously. In certain embodiments, the amphetamine and the dopamine reuptake inhibitor are administered as part of a single composition. In certain embodiments, the single composition is for oral administration or for transdermal administration.

In yet another aspect, the invention relates to a method for preparing a pharmaceutical preparation, comprising combining an amphetamine (or an analog or metabolite thereof), a dopamine reuptake inhibitor, and a pharmaceutically acceptable excipient in a composition for simultaneous administration of the two drugs.

In still another aspect, the invention relates to a method for conducting a pharmaceutical business, by manufacturing a preparation of amphetamine (or an analog or metabolite thereof) and a dopamine reuptake inhibitor or a kit including separate formulations of each, and marketing to healthcare providers the benefits of using the preparation or kit in the treatment of ADHD.

In yet another aspect, the invention provides a method for conducting a pharmaceutical business, by providing a distribution network for selling the combinatorial preparations and kits, and providing instruction material to patients or physicians for using such preparation to treat ADHD.

In still a further aspect, the invention relates to a method for conducting a pharmaceutical business, by determining an appropriate formulation and dosage of a amphetamine (or an analog or metabolite thereof), a dopamine reuptake inhibitor to be co-administered in the treatment of ADHD, conducting therapeutic profiling of identified formulations for efficacy and toxicity in animals, and providing a distribution network for selling a preparation as having an acceptable therapeutic profile. In certain embodiments, the method further includes an additional step of providing a sales group for marketing the preparation to healthcare providers.

In yet another aspect, the invention provides a method for conducting a pharmaceutical business by determining an appropriate formulation and dosage of a amphetamine (or an analog or metabolite thereof), a dopamine reuptake inhibitor to be co-administered in the treatment of ADHD, and licensing, to a third party, the rights for further development and sale of the formnulation.

In certain embodiments, the invention contemplates the treatment of amnesia. Amnesias are described as specific defects in declarative memory. Faithful encoding of memory requires a registration, rehearsal, and retention of information. The first two elements appear to involve the hippocampus and medial temporal lobe structures. The retention or storage appears to involve the heteromodal association areas. Amnesia can be experienced as a loss of stored memory or an inability to form new memories. The loss of stored memories is known as retrograde amnesia. The inability to form new memories is known as anterograde amnesia.

Complaints of memory problems are common. Poor concentration, poor arousal and poor attention all may disrupt the memory process to a degree. The subjective complaint of memory problems therefore must be distinguished from true amnesias. This is usually done at the bedside in a more gross evaluation and through specific neuropsychological tests. Defects in visual and verbal memory can be separated through such tests. In amnesias there is by definition a preservation of other mental capacities such as logic. The neurobiologic theory of memory described above would predict that amnesias would have relatively few pathobiologic variations. Clinically the problem of amnesias often appears as a result of a sudden illness in an otherwise healthy person.

Exemplary forms of amnesias which may be treated by the subject method include amnesias of short duration, alcoholic blackouts, Wernicke-Korsakoff's (early), partial complex seizures, transient global amnesia, those which are related to medication, such as triazolam (Halcion), and basilar artery migraines. The subject method may also be used to treat amnesias of longer duration, such as post concussive or as the result of Herpes simplex encephalitis.

In certain embodiments, this invention contemplates the treatment of the Anterior Communicating Artery Syndrome. This syndrome is prevalent among survivors of Anterior Communicating artery aneurysms and often includes anterograde amnesia, a specific deficit in new memory formation, with relative sparing of older memories as well as intelligence and attention. The Anterior Communicating Artery Syndrome may also include some personality changes and confabulation. There is a considerable anatomic and clinical evidence that the Anterior Communicating Artery Syndrome in man is a result of a focal lesion in the basal forebrain area particularly the medial septal area), secondary to combined damage from the aneurysm and the surgical or endovascular treatment of the aneurysm.

In addition, the compounds of the invention may be usefwl in enhancing memory in normal individuals.

Exemplification

The invention now being generally described, it will be more readily understood by reference to the following examples which are included merely for purposes of illustration of certain aspects and embodiments of the present invention, and are not intended to limit the invention.

The Inhibitory Avoidance (IA) task and the Spontaneous Object Recognition (SOR) task are well-studied behavioral paradigms which can provide the researcher with a consistent and long lasting measure of memory. The paradigms consists of one training trial and one retention trial. Test substances may be administered to the rats either before or after training. Improved memory, as a result of test substance administration, is evident as increased latency on the retention trial. The objective of the following experiments was to investigate the effects of amphetamine on IA and SOR memory in the rat.

General Experimental Procedures
Inhibitory Avoidance

The Inhibitory Avoidance apparatus (Coulboum Instruments) consisted of a light chamber and a dark chamber, which were joined by means of a sliding guillotine door. The floor of the dark compartment consisted of 2.4 mm diameter steel rods, through which a foot-shock could be administered to the animal by a constant current 18-pole shock scrambler. The test apparatus was enclosed in a ventilated, sound-attenuating cabinet, and was controlled by Graphic State Notation Software (Version 1.013) and a Hewlett Packard Pavilion Computer. Training involved the rat being placed in the light hamber for a ten second period, after which time the sliding door was opened, allowing the rat access to the dark chamber. Two seconds after entering the dark chamber, a continuous 0.46 mA foot-shock was delivered through the floor grid for two seconds. The animal was then removed from the apparatus and returned to the home cage. The animals received a retention test 24 hours following training. The retention test was identical to training except that no foot-shock was delivered. Latency to enter the dark chamber was recorded, and the animals were then returned to their home cages. Data was collected by the Graphic State Notation software, and was recorded onto an appropriate data sheet.

Spontaneous Object Recognition

Apparatus for Object Recognition testing consisted of a plexiglass open field activity chamber, measuring 30 by 30 cm. A video camera was mounted on the wall above the chamber. Three plastic objects served as stimuli for the experiment. Two of the objects were identical to one another, and the third was different. Rats were individually habituated to the open-field box for three consecutive days. Habituation sessions were six minutes in duration. Twenty-four hours after the last day of habituation, a training session was conducted, in which two identical objects were placed in the open-field box, 10 cm from the back wall. The animal was placed into the box and was allowed to explore freely for a period of four minutes. Twenty-four hours after the training session, retention testing was conducted. During retention testing, the rat was placed back into the same activity box with one of the familiar objects used during the training session and a novel object that the rat had not seen before. The rat was allowed to explore the box and objects for a period of four minutes. Testing was conducted at the same time each day, and was videotaped for off-line analysis. Two discrimination indices, D1 and D2 were calculated in order to measure the strength of recognition memory. D1 reflects the amount of time spent exploring the novel object minus the amount of time spent exploring the familiar object, and D2 reflects D1 divided by total exploration time.

Activity Monitoring

Locomotor activity monitoring utilizes an apparatus that consists of photocell activity cages with a wire grid base in which the photocell beam is placed. The animals are placed in individual activity cages some period of time prior to administration of agents. Locomotor activity is measured by the number of interruptions of the photoelectric beam during An maximum locomotor activity corresponds to a maximum number of interruptions of the light beam. General behavior and activity levels were recorded by a computerized monitoring system for a period of ten minutes. The analyzed behaviors included but were not limited to; horizontal activity, total distance moved, movement time, number of movements, number of rears, number of stereotyped movements, and time spent resting. Data was collected on-line using Versa Max (Version 1.83) computer software and a Hewlett Packard Pavilion computer.

Tail Flick

For Tail-Flick Analgesia Testing, the animal was placed on top of the Tail-Flick monitor and gently held in place with a cotton towel. The tail of the animal was placed in a shallow groove lying between two sensors and over the top of a radiant heat wire. The Tail Flick monitor was activated, and the latency for the animal to flick its tail out of the groove and away from the heat source was recorded. The animal was returned to its home cage immediately following testing.

Fornix Lesions

Rats were anesthetized with Nembutal (55 mg/kg) and prepared for surgery. The rat was placed in the stereotaxic apparatus, a midline incision made, and the scalp retracted to expose the skull. The skull was cleaned and dried using sterile saline and cotton swabs, and four stereotaxically determined holes were drilled in the skull at the following coordinates: 0.3 and 0.8 mnm posterior to Bregina, and O.5 and 0.7 mm lateral to the midline. An electrode (Teflon-coated wire, 125 $\mu$m in diameter) was lowered into the brain to a depth of 4.6 mm, and DC current at 1.0 mA was passed through the electrodes for a duration of 10 seconds. The electrodes were then removed, and the wound was sutured. Animals were removed from the stereotaxic apparatus and received postoperative care and monitoring until fully conscious. The rats were lefi to recover for a period of seven days prior to behavioral testing. The health status of the animals was checked in a daily basis during the recovery period.

Experiment 1: Dose Restoonse Testing

Effects of S-(+)-amphetamine on Inhibitory Avoidance

Figure 2:
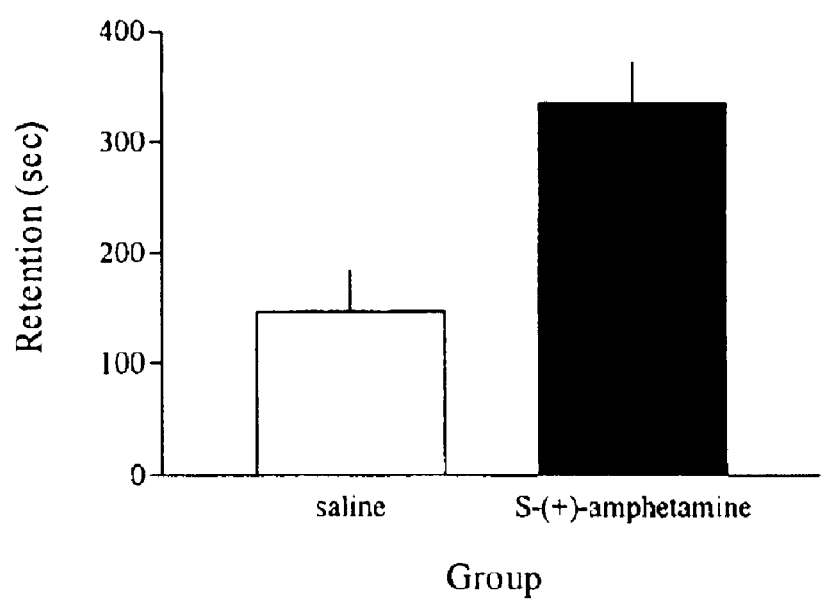
FIG. 2 demonstrates the effect of 2 mg/kg of S-(+)-amphetamine on Performance in the Inhibitory Avoidance Task.

In this experiment, rats were injected with three different doses of S-(+) amphetamine thirty minutes prior to being trained on the IA task. As can be seen from FIG. 1, a dose of 2 mg/kg of amphetamine improved retention of the task, while doses of 0.25, 0.50 and 1.0 mg/kg had no effect. In order to verify this result, a second experiment was conducted. Rats were injected with 2.0 mg/kg of amphetamine and trained on the IA task. As can be seen from FIG. 2, this dose of S-(+)-amphetamine significantly improved retention of the task. An unpaired t-test demonstrated that this enhancement was statistically significant ($p<0.01$).

Effects of R-(−)-amphetamine (C105) on Inhibitory Avoidance

The first experiment to be conducted using C105 was a dose response experiment, in which different doses of C105 (0.4, 0.5, 0.75, 1.0 and 2.0 mg/kg) were administered to the rats one hour prior to training on the Inhibitory Avoidance task. Retention for the task was tested 24-hours later. A one way ANOVA was conducted on the data, and the results revealed a statistically significant difference between the dose level groups ($F(5,59)=168600$, $p<0.01$). Subsequent post hoc analysis (Student Newman Keuls) demonstrated that the 1.0 mg/kg group performed significantly better than saline injected controls ($p<0.05$). The 0.5 mg/kg dose also appeared to be effective in enhancing the animals performance, however, this trend did not reach statistical significance. This experiment was subsequently replicated using 0.5 mg/kg as the target dose in order to verify this result (see section 9.1.4). Dose Response data is presented individually in Table 3.

Effects of R-(−)-amphetamine (C105) on Inhibitory Avoidance

Figure 8:
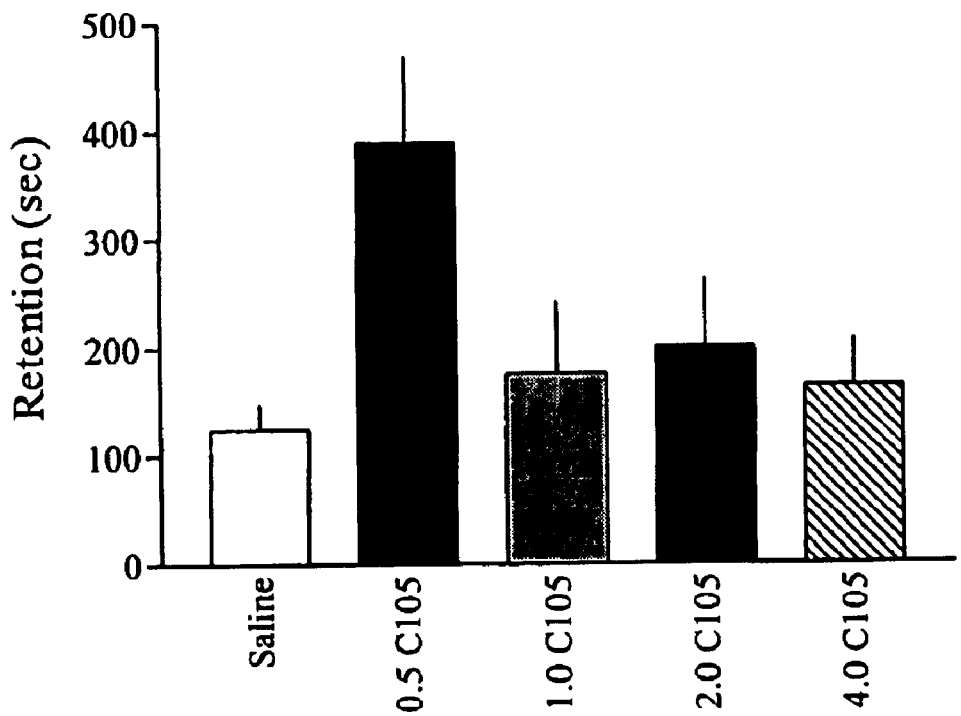
FIG. 8 presents the effectiveness of various doses of R-(−)-amphetamine on memory retention.

In this experiment, four groups of 10 rats were injected with different doses (0.5 mg/kg, 1.0 mg/kg, 2.0 mg/kg or 4.0 mg/kg) of the R-(−) enantiomer of amphetamine one hour prior to being trained on the IA task. The experiments were conducted with a 24 hour retention interval and a 0.46 mA shock intensity. As can be seen in FIG. 8, a much lower dose of R-(−)-amphetamine is required for the same improved retention effect as obtained with S-(+)-amphetamine (compare to FIG. 1). Increasing the dose above 0.5 kg/mg did not further improve the retention results obtained with this dose possibly indicating a saturation effect.

Effects of R-(−)-amphetamine (C105) on Inhibitory Avoidance

In order to investigate whether doses of C105 lower than 0.5 mg/kg enhanced performance, rats were injected with 0.1, 0.25 or 0.5 mg/kg of C105 one hour prior to training. Retention was tested 24-hours later. This experiment revealed that doses of C105 lower than 0.5 mg/kg were not effective in improving the mnemonic performance of the rats. In contrast, the 0.5 mg/kg dose significantly enhanced performance on the task ($F(3,39)=67450$, $p<0.0477$). These data are presented individually in Table 4.

Experiment 2: Time Course of Effectiveness

Figure 3:
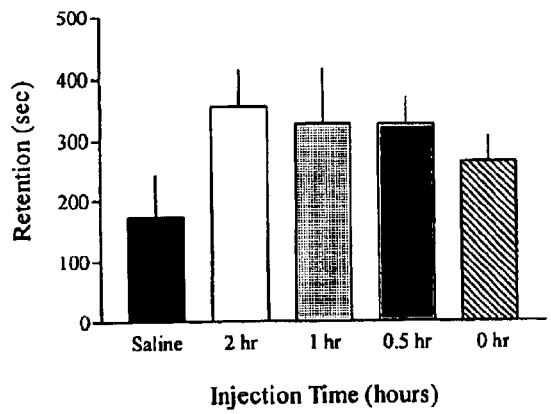
FIG. 3 shows the varying effect of S-(+)-amphetamine depending on the time between administration and inception of training.

In this experiment, the time of drug administration was varied in order to determine the optimal pre-training drug administration time. FIG. 3 shows that S-(+) amphetamine (2.0 mg/kg) is effective when administered to the rats between 0 and 2 hours prior to training.

Experiment 3: Long Term Retention

Figure 4:
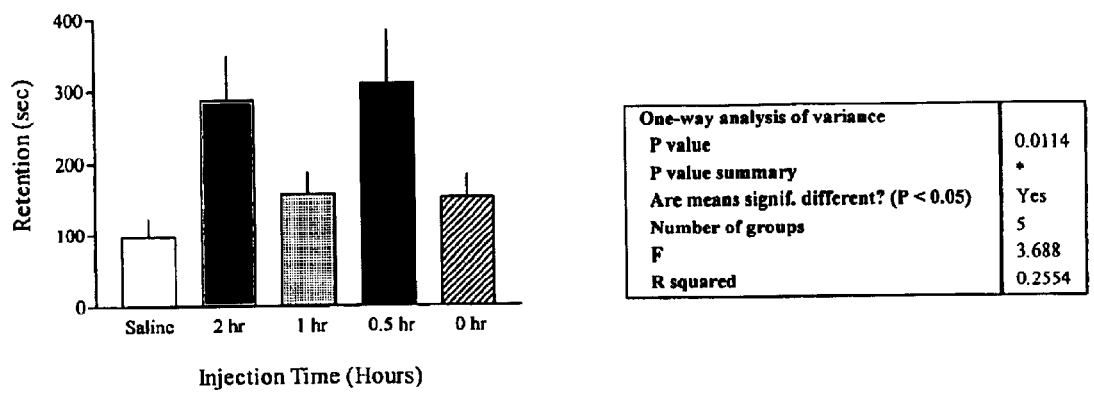
FIG. 4 illustrates the effect of S-(+)-amphetamine on memory retention one week after the initial training.

This experiment was conducted in order to determine whether the enhanced retention observed in Experiment 2 was long-lasting. Rats received a second retention test one week after the first retention test. No additional training or drug was administered to the animals in the interim period. FIG. 4 illustrates that rats that had received S-(+)-amphetamine the previous week performed significantly better than rats that had received control injections of vehicle solution ($F(4,47)=3.688$, $p<0.01$).

Experiment 4: Effects on Lesioned Animals

Effects of S-(+)-amphetamine on Lesioned Animals

The findings of the above experiments are important, as they identify the most effective dose and time of administration for this compound. Moreover, the results demonstrate that S-(+)-amphetamine improves memory in normal rats, and that this improvement is long-lasting. In the next experiment, we investigated whether the performance of amnesic rats could be improved by administration of amphetamine. In this experiment, control rats and rats with lesions of the fornix received injections of either saline or amphetamine (2.0 mg/kg), and one hour later, were tested on the IA task.

Figure 5:
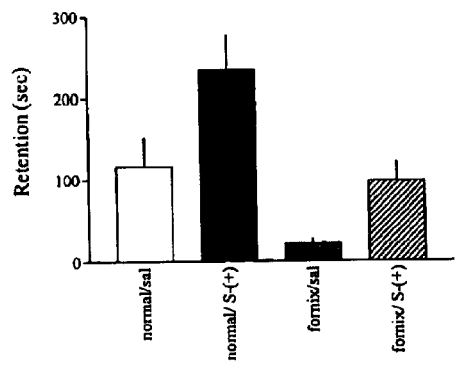
FIG. 5 depicts the effects of S-(+)-amphetamine on normal and fornix-lesioned animals.

As FIG. 5 illustrates, S-(+)-amphetamine dramatically enhanced the performance of normal rats and in addition, appeared to improve the performance of the fornix lesion rats. A one way ANOVA demonstrated that there was a significant difference between the performance of the four groups ($F(3,36)=8.687$, $p<0.002$). Student-Newman-Keuls post hoc tests revealed firstly that the performance of normal rats that received S-(+)-amphetamine was significantly enhanced relative to all other experimental groups ($p<0.05$). In addition, the performance of fomix animals that received S-(+)-amphetamine was not significantly different from normal, saline injected animals. These results demonstrate that amphetamine is capable of enhancing memory in normal rats and has beneficial effects in brain damaged, amnesic rats.

Effects of R-(−)-amphetamine on Lesioned Animals

Figure 12:
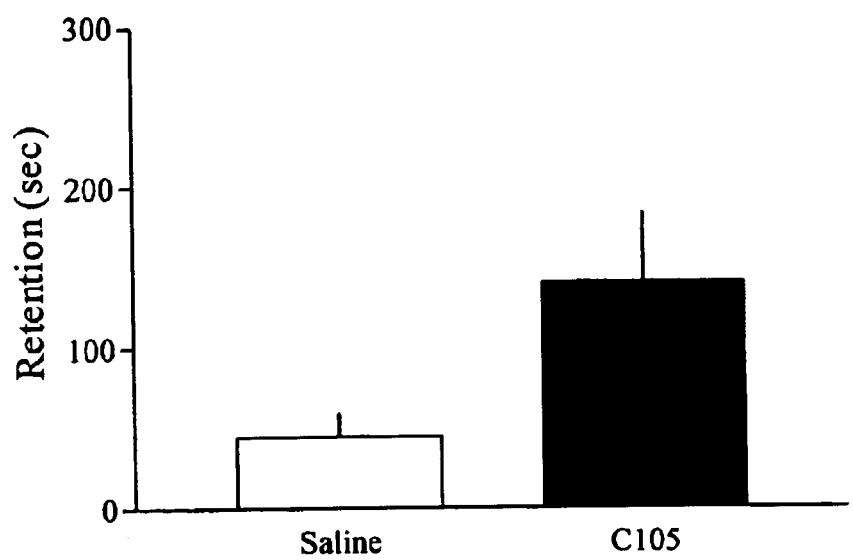
FIG. 12 shows the effect of R-(−)-amphetamine (1.0 mg/kg) on Inhibitory Avoidance Performance in Fornix Lesion Rats.

Rats with bilateral lesions of the fornix were tested on the Inhibitory Avoidance task. All rats were injected with test (0.5, 1.0, 2.0 and 4.0 mg/kg) or control article one hour prior to testing. A one-way ANOVA demonstrated that there was a significant main effect of dose (F(4,45)=15580, p<0.0316). A dose of 1.0 mg/kg of C105 appeared to be most effective in improving the performance of the fornix lesion animals. Data from this experiment are illustrated in FIG. 12 and presented individually in Table 7.

Figure 13:
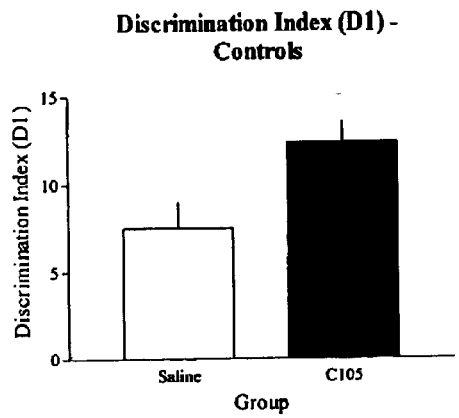
FIG. 13 shown the effect of R-(−)-amphetamine on Performance in the Object Recognition Task in Normal and Fornix Lesion Rats.
Figure 13:
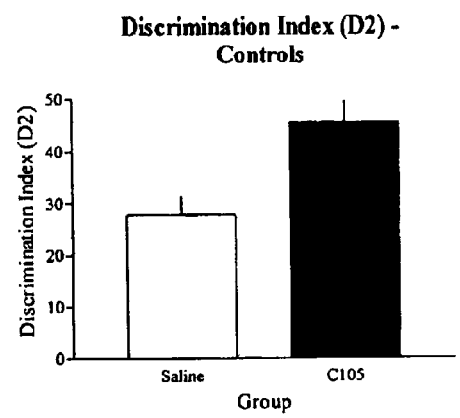
Figure 13:
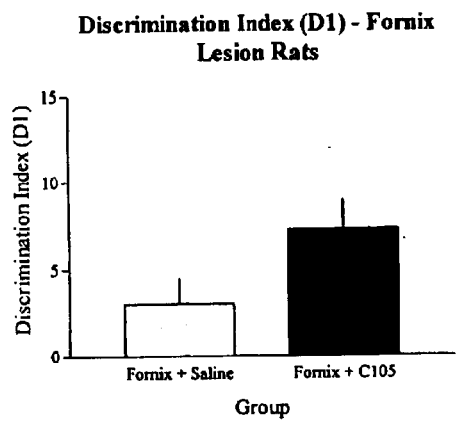
Figure 13:
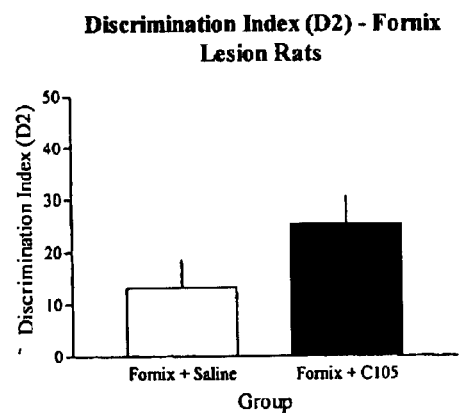

Rats with lesions of the fornix were also tested on the Object Recognition task. Rats received I.P injections of C105 (1.0 mg/kg) or saline immediately after the training session, and were tested for retention 24-hours later. As can be seen from FIG. 13, when compared with controls, lesions of the fornix had a detrimental effect on performance of this task. Administration of C105 produced a trend towards improving discrimination performance in D1 (p=0.0685), and slightly improved performance in D2.

Experiment 5: Effects of R-(-) vs. S-(+) Amphetamine Enantiomers on Stimulation of Memory Consolidation The effects of R-(-) vs. S-(+) amphetamine enantiomers on stimulation of memory consolidation and motor stimulation were compared. The R-(-) enantiomer of amphetamine is referred to as C105 in the figures.

Effects of S-(+)-amphetamine on Inhibitory Avoidance

Figure 6:
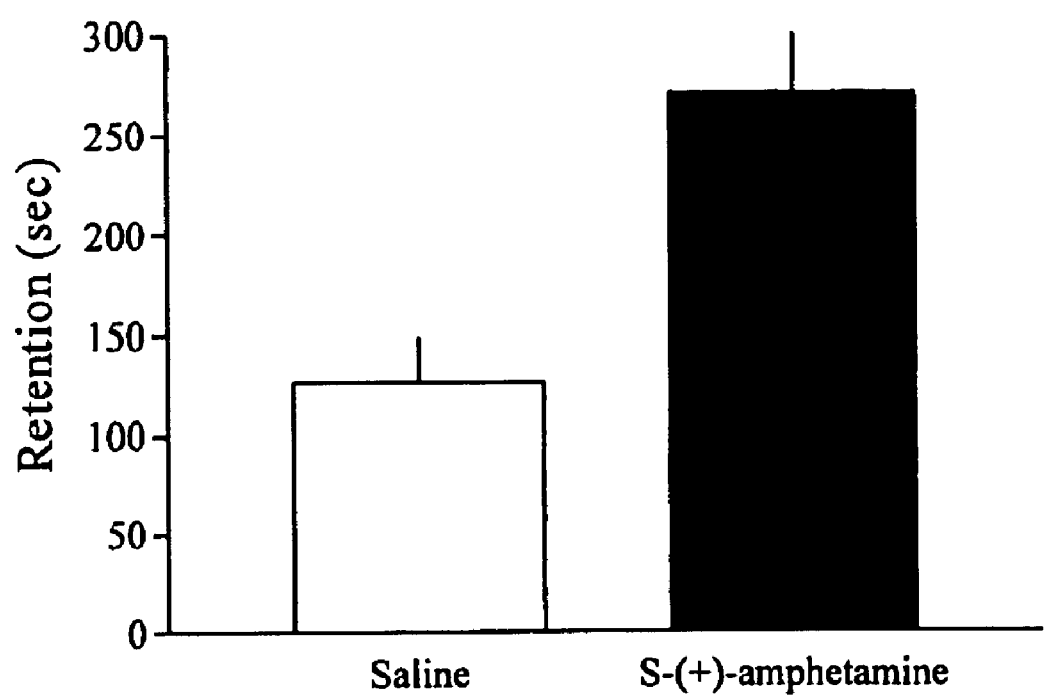
FIG. 6 shows the effect of S-(+)-amphetamine (2.0 mg/kg) on Performance in Inhibitory Avoidance.

An experiment was conducted in which different doses of S-(+)-amphetamine were administered to rats one hour before training on the Inhibitory Avoidance task and were compared to a control group of rats injected with saline. Retention for the task was tested 24 hours later with a 0.46 mA shock intensity. Results for this experiment are presented individually in Tables 1 and 2, and demonstrated that S-(+)-amphetamine appeared to enhance performance when administered at a dose of 2.0 mg/kg. The experiment was subsequently replicated several times using a test-article dose of 2.0 mg/kg. Results from these experiments are represented in FIG. 6, and demonstrate that S-(+)-amphetamine significantly enhanced memory for the Inhibitory Avoidance task (t (76)=3.416, p<0.001). These results are in agreement with previous research and help to demonstrate the effectiveness of S-(+)-amphetamine as a memory-enhancing drug.

Effects of R-(-)-amphetamine (C105) on Inhibitory Avoidance

Figure 9:
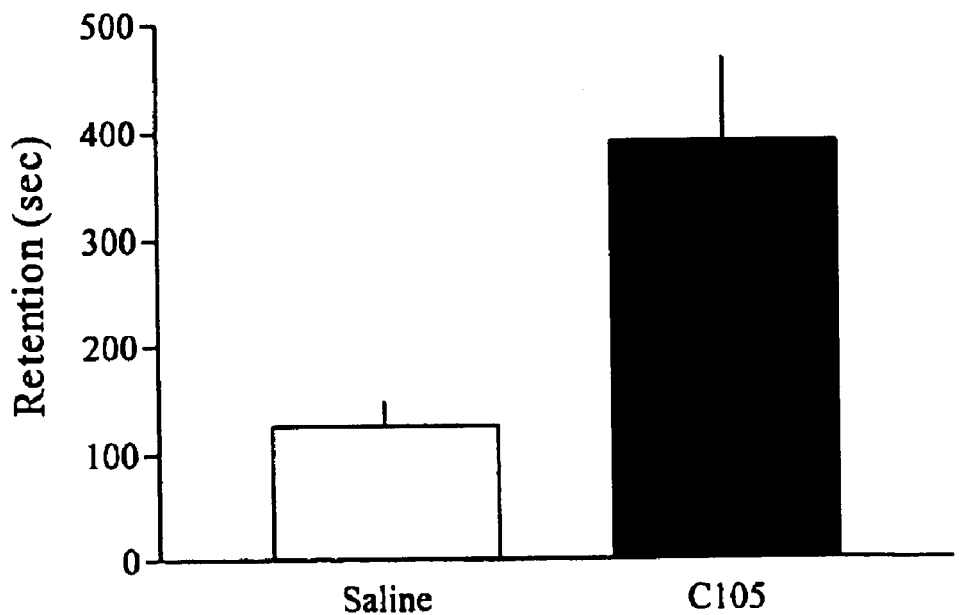
FIG. 9 demonstrates the effectiveness of R-(−)-amphetamine on memory retention.

In order to verify the results from the dose response test, a second experiment with R-(-)amphetamine was conducted. Eighteen rats were injected with a dose of 0.5 mg/kg of R-(-)-amphetamine one hour prior to being trained on the IA task. The R-(-) amphetamine treated rats were compared to control rats injected with saline. The experiments were conducted with a 24 hour retention interval and a 0.46 mA shock intensity. As can be seen in FIG. 9, this dose of R-(-)-amphetamine significantly improved retention of the task. An unpaired t-test demonstrated that this enhancement was statistically significant (p<0.002).

Figure 10:
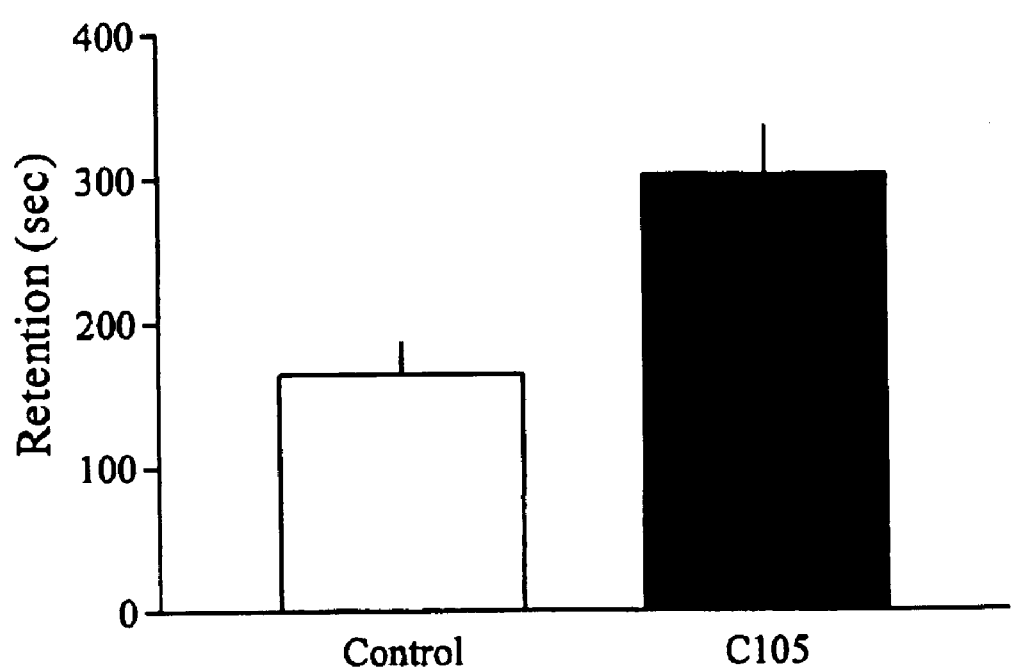
FIG. 10 shown the effect of R-(−)-amphetamine (0.5 mg/kg) on Performance in the Inhibitory Avoidance Task.

Based on the results obtained from the experiments described above, several more experiments were conducted investigating the effects of a 0.5 mg/kg dose of C105 on Inhibitory Avoidance. The data presented in FIG. 10, and individually in Table 5, represent a summary of all such experiments. The results of these experiments clearly demonstrate a memory enhancing effect as measured by the Inhibitory Avoidance task. Rats that had been injected with C105 (0.5 mg/kg) one hour prior to training performed significantly better than control animals on the 24-hour retention test (t (132)=3.438, p<0.0008).

Effects of R-(-)-amphetamine (C105) on Object Recognition

In order to investigate the effects of C105 on recognition memory, rats were trained on the Spontaneous Object Recognition task. Normal rats were injected with 0.5 mg/kg C105 immediately following the training session, and were tested for retention 24-hours later. The results of the experiment indicate that C105 significantly improved recognition memory. Rats that had received injections of test article immediately after the training session, performed significantly better than their saline injected counterparts, as they spent more time exploring the novel object during retention testing. Both discrimination indices, D1 and D2, which reflect discrimination between the familiar and novel object, were significantly higher in C105 treated animals [(t(51)=2.526, p<0.0147) and (t(51)=3.197, p<0.0024) respectively]. These results are particularly interesting, as recognition memory is the process by which a subject is aware that a stimulus has previously been experienced. This process requires that incoming stimuli be identified and compared with representations of previously encountered stimuli stored in memory. Recognition memory is used during everyday life and failures of recognition memory undoubtedly contribute to the problems encountered by amnesic patients. Results from this experiment are presented in FIG. 13, and individual data are presented in Table 8.

It is interesting at this point to compare the results obtained with R-(-)-amphetamine (C105) to those obtained with S-(+)-amphetamine. S-(+)-Amphetamine had a memory enhancing effect at a dose of 2.0 mg/kg, while R-(-)-amphetamine had a memory enhancing effect on the same task at a dose of 0.5 mg/kg. Although definitive dose-response relationship experiments between these two compounds have not been conducted, it seems likely that C105 is a more potent memory enhancer for this particular task in rats. It should be noted however, that the maximal efficacy of the two compounds are the same.

Experiment 6: Effects-of R-(-) vs. S-(+)-amphetamine on Motor Stimulation

Effects of S-(+)-amphetamine on Activity Levels

In order to provide a comparison point for the results described above, a second experiment was conducted in which rats were injected with 2 mg/kg of S-(+)-amphetamine prior to activity testing. Results for this experiment are presented in FIG. 7. The results demonstrated that S-(+)-amphetamine produced a clear and significant enhancement in locomotor activity for the entire 10 minute session. Significant main effects for the variables of total distance (F(9, 70)=1514000, p<0.0001); number of movements (F(9,70)=45.89, p<0.0001); movement time (F(9,70)=53.07, p<0.0001); rears (F(9,70)=49.47, p<0.0001), stereotyped movements (F(9,70)=24.65, p<0.0001) and rest time (F(9,70)=44.34, p<0.0001) were observed. No significant effects of time or time-drug interactions were observed.

Effects of R-(-)-amphetamine (C105) on Activity Levels

Figure 14:
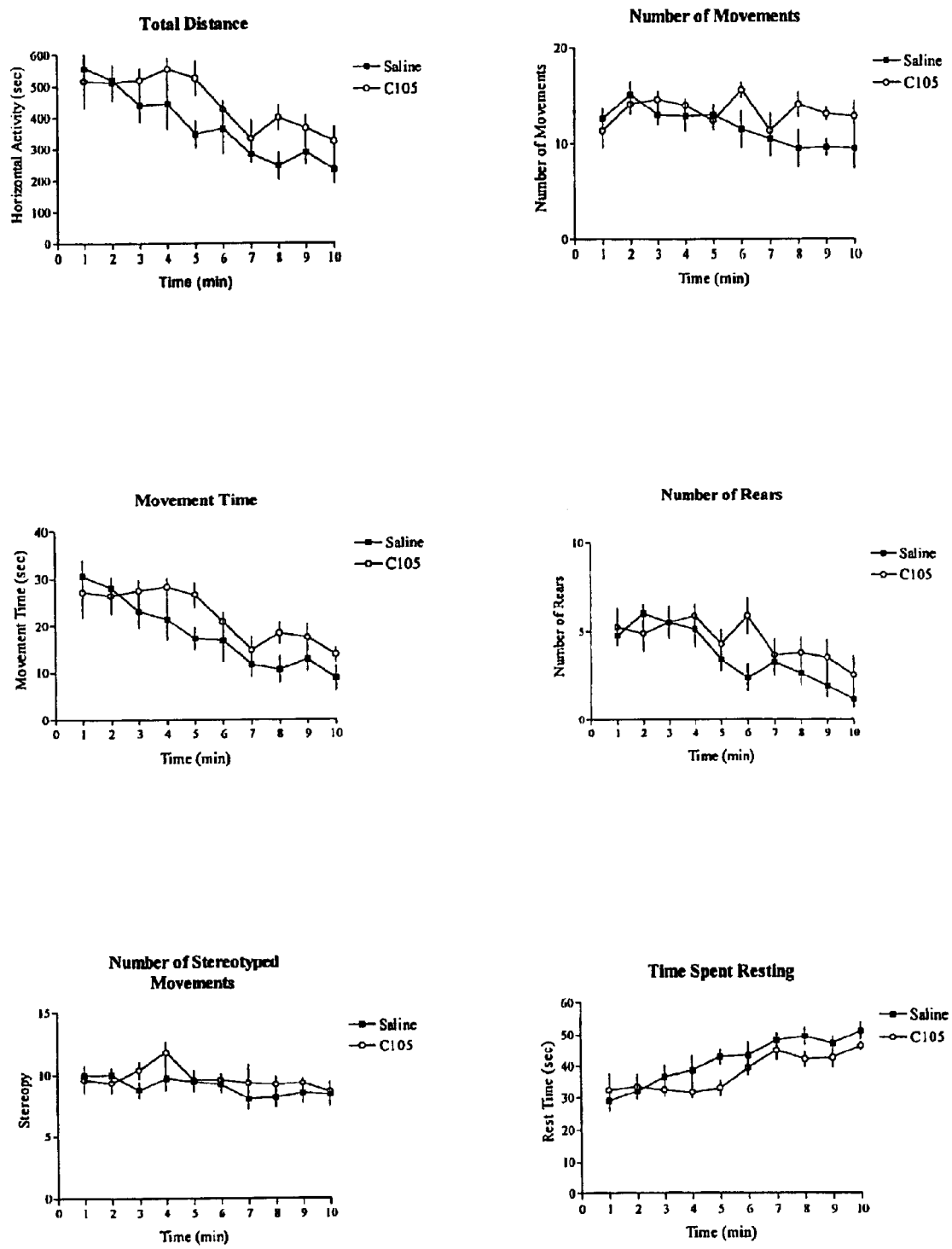
FIG. 14 shows the effect of R-(−)-amphetamine (0.5 mg/kg) on Activity Levels.
Figure 15:
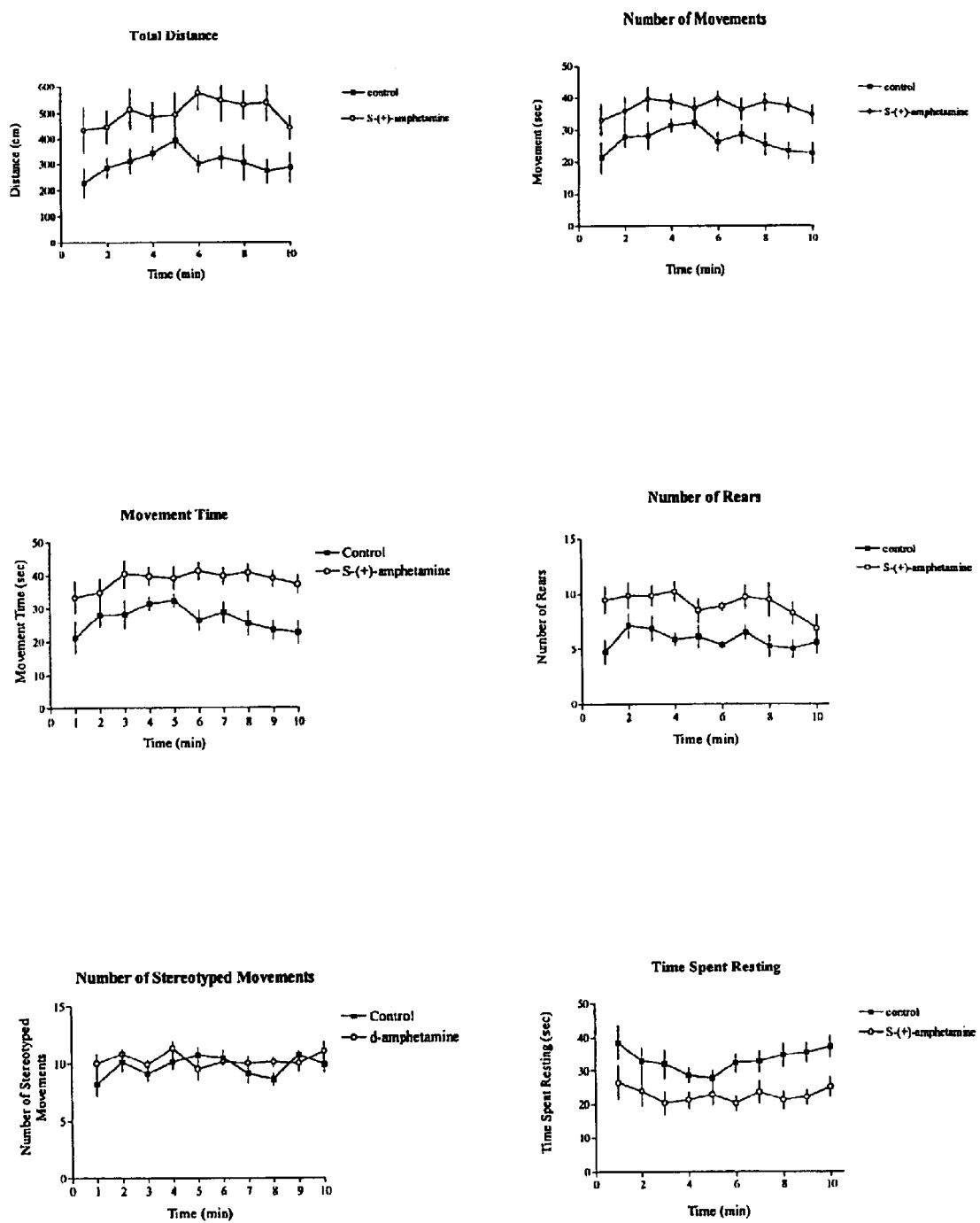
FIG. 15 shows the effect of S-(+)-amphetamine (2 mg/kg) on Activity Levels.

In this experiment, rats were injected with 0.5 mg/kg of R-(-)-amphetamine (C105) and compared to a control group of rats injected with saline. Rat activity was monitored for a 10 minute period one hour after R-(-)-amphetamine injection. As can be seen in FIG. 14, treatment with R-(-)-amphetamine had no significant effects on the activity levels of the rats as compared to the control group.

Figure 7:
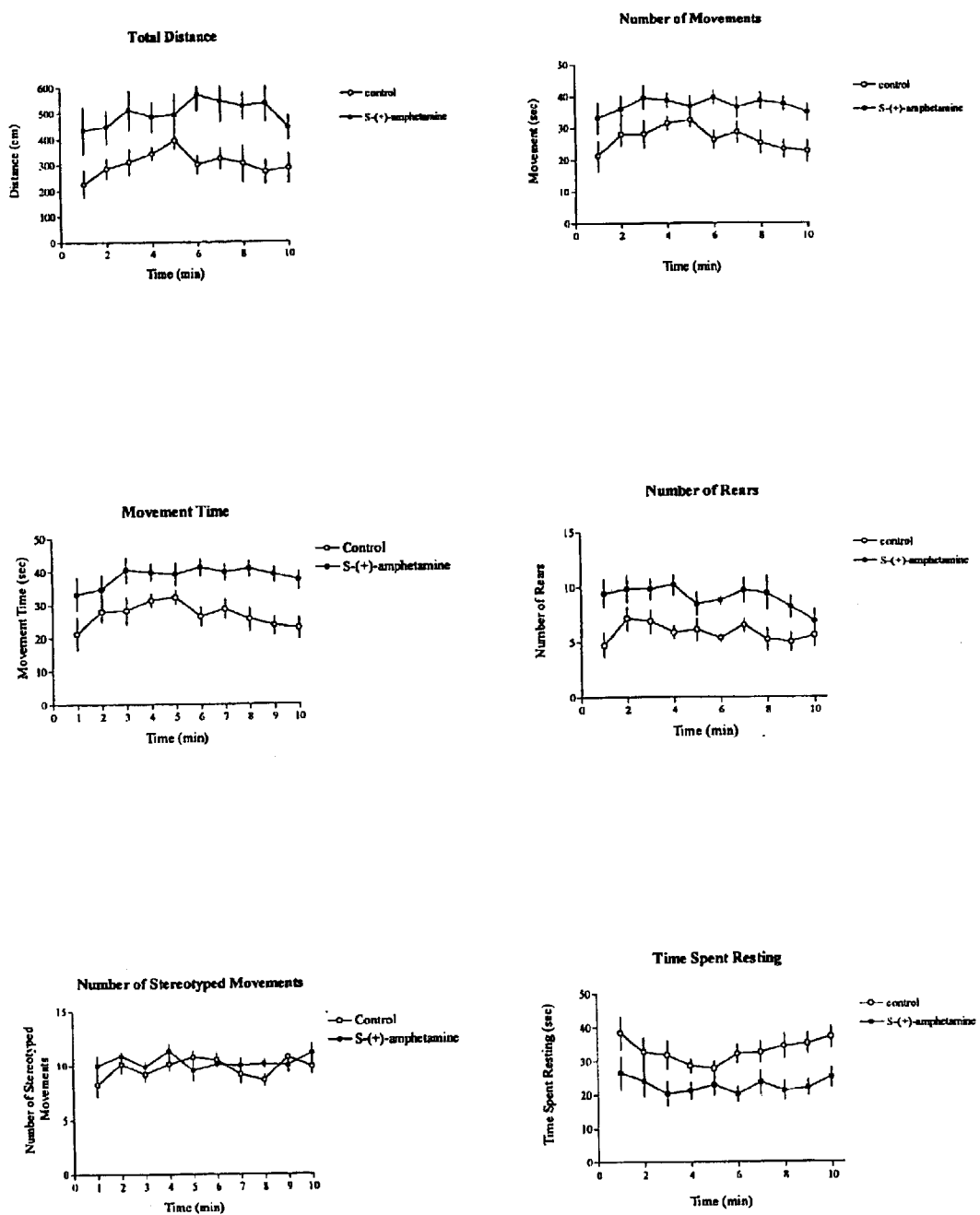
FIG. 7 shows the effect of S-(+)-amphetamine on Activity Levels.

This data indicates that R-(-)-amphetamine can provide improved memory consolidation without producing the motor stimulatory effects observed in the S-(+)-amphetamine treated rats (compare to FIG. 7). A comparison of the results obtained for (S)-(+)-versus R-(-)-amphetamine indicates that S-(+)-amphetamine produced a larger locomotor effect than R-(-)-amphetamine, at doses that are equally effective in enhancing memory. This observation is consistent with previous research, which has repeatedly demonstrated that S-(+)-amphetamine is between 4 and 10 times more potent than R-(-)-amphetamine in producing elevated locomotor responses.

Experiment 7: Tail Flick

Figure 16:
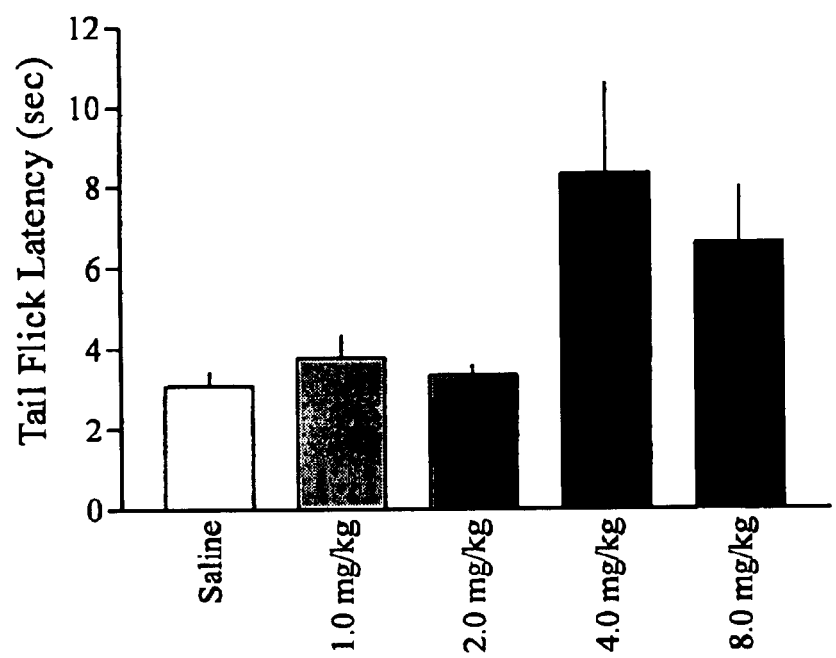
FIG. 16 shown the effect of R-(−)-amphetamine on Tail-Flick Analgesia.

Tail Flick Analgesia data is presented in FIG. 16, and individual data in Table 12. Administration of 1.0, 2.0, 4.0 or 8.0 mg/kg of C105 one hour prior to testing resulted in varying degrees of analgesia. 1.0 and 2.0 mg/kg had no analgesic properties, while 4.0 and 8.0 did. Statistical significance was observed at the 4.0 mg/kg dose (F(4,39)= 43.18, p<0.0117). This experiment indicates that the therapeutic dose of R-(-)-amphetamine had no effect on analgesia, as measured by the tail-flick analgesiometer.

Experiment 8: Post Training Administration

Figure 11:
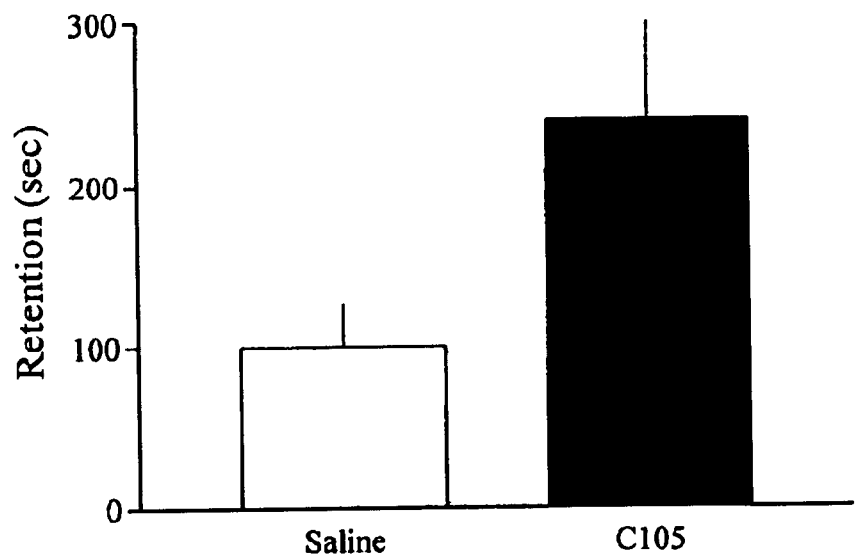
FIG. 11 shows the effect of Post Training Administration of R-(−)-amphetamine (0.5 mg/kg) on Performance in the Inhibitory Avoidance Task.

While the results described above provide evidence to suggest that C105 enhances memory, it is possible that these results are due to non-mnemonic factors. Because the drug was administered prior to training, it is possible that learning or acquisitional processes were affected by drug administration. For this reason, a post training experiment was conducted in which C105 was administered to the rats immediately after the training session. Injecting the drug after the training session affects memory consolidation rather than acquisition, primarily because the drug is not on board at the time of training. The results of this experiment are represented in FIG. 11 and presented individually in Table 6. As can be seen from FIG. 11, post training administration of 0.5 mg/kg of C105 significantly enhanced performance on the Inhibitory Avoidance task (t(26)=2.160, p<0.0402). This experiment therefore, provides strong evidence that C105 works by selectively enhancing memory consolidation.

TABLE 1

Effects of Different Doses of S-(+)-Amphetamine on Inhibitory Avoidance

| Saline | 0.25 mg/kg | 0.5 mg/kg | 1.0 mg/kg | 2.0 mg/kg |
|---|---|---|---|---|
| 22.0 | 6.0 | 2.0 | 7.0 | 33.0 |
| 25.0 | 19.0 | 26.0 | 17.0 | 63.0 |
| 26.0 | 29.0 | 38.0 | 19.0 | 82.0 |
| 33.0 | 29.0 | 39.0 | 25.0 | 84.0 |
| 41.0 | 44.0 | 63.0 | 31.0 | 101.0 |
| 71.0 | 59.0 | 65.0 | 34.0 | 190.0 |
| 121.0 | 94.0 | 110.0 | 35.0 | 230.0 |
| 216.0 | 124.0 | 153.0 | 47.0 | 245.0 |
| 234.0 | 310.0 | 207.0 | 157.0 | 457.0 |
| 358.0 | 452.0 | 207.0 | 263.0 | 517.0 |

Data are expressed as latency to enter the dark side of the apparatus in seconds for each animal (10 animals per treatment group). Data is rank-ordered.

TABLE 2

Summary of Effects of S-(+)-Amphetamine (2.0 mg/kg) on Inhibitory Avoidance

| Saline | S-(+)-Amphetamine |
|---|---|
| 3.0 | 5.0 |
| 6.0 | 15.0 |
| 11.0 | 26.0 |
| 17.0 | 32.0 |
| 19.0 | 33.0 |
| 22.0 | 60.0 |
| 25.0 | 63.0 |
| 26.0 | 82.0 |
| 30.0 | 84.0 |
| 33.0 | 100.0 |

TABLE 2-continued

Summary of Effects of S-(+)-Amphetamine (2.0 mg/kg) on Inhibitory Avoidance

| Saline | S-(+)-Amphetamine |
|---|---|
| 33.0 | 101.0 |
| 33.0 | 127.0 |
| 36.0 | 148.0 |
| 40.0 | 167.0 |
| 41.0 | 169.0 |
| 42.0 | 188.0 |
| 44.0 | 190.0 |
| 53.0 | 201.0 |
| 53.0 | 204.0 |
| 57.0 | 222.0 |
| 63.0 | 230.0 |
| 71.0 | 237.0 |
| 80.0 | 245.0 |
| 105.0 | 248.0 |
| 110.0 | 289.0 |
| 121.0 | 296.0 |
| 148.0 | 300.0 |
| 204.0 | 300.0 |
| 214.0 | 364.0 |
| 216.0 | 365.0 |
| 234.0 | 371.0 |
| 242.0 | 457.0 |
| 262.0 | 461.0 |
| 266.0 | 517.0 |
| 286.0 | 557.0 |
| 297.0 | 636.0 |
| 349.0 | 736.0 |
| 358.0 | 820.0 |
| 673.0 | 900.0 |

Data are expressed as latency to enter the dark side of the apparatus in seconds for each animal (39 animals per treatment group). Data is rank-ordered.

TABLE 3

Effects of Different Doses of C105 on Inhibitory Avoidance

| Saline | 0.4 mg/kg | 0.5 mg/kg | 0.75 mg/kg | 1.0 mg/kg | 2.0 mg/kg |
|---|---|---|---|---|---|
| 17.0 | 45.0 | 16.0 | 9.0 | 101.0 | 30.0 |
| 55.0 | 62.0 | 38.0 | 15.0 | 115.0 | 59.0 |
| 60.0 | 80.0 | 137.0 | 16.0 | 121.0 | 59.0 |
| 77.0 | 87.0 | 203.0 | 21.0 | 202.0 | 127.0 |
| 103.0 | 170.0 | 267.0 | 150.0 | 265.0 | 137.0 |
| 107.0 | 231.0 | 332.0 | 157.0 | 343.0 | 230.0 |
| 116.0 | 236.0 | 556.0 | 229.0 | 729.0 | 231.0 |
| 129.0 | 250.0 | 698.0 | 237.0 | 813.0 | 253.0 |
| 240.0 | 265.0 | 741.0 | 288.0 | 824.0 | 366.0 |
| 280.0 | 629.0 | 900.0 | 650.0 | 900.0 | 384.0 |

Data are expressed as latency to enter the dark side of the apparatus in seconds for each animal (10 animals per treatment group). Data is rank-ordered.

TABLE 4

Effects of Low Doses of C105 on Inhibitory Avoidance

| Saline | 0.1 mg/kg | 0.25 mg/kg | 0.5 mg/kg |
|---|---|---|---|
| 33.0 | 37.0 | 24.0 | 127.0 |
| 38.0 | 37.0 | 28.0 | 137.0 |
| 55.0 | 39.0 | 29.0 | 144.0 |
| 62.0 | 39.0 | 71.0 | 164.0 |
| 80.0 | 55.0 | 71.0 | 167.0 |
| 100.0 | 55.0 | 100.0 | 182.0 |
| 216.0 | 110.0 | 113.0 | 219.0 |
| 235.0 | 113.0 | 117.0 | 265.0 |

TABLE 4-continued

Effects of Low Doses of C105 on Inhibitory Avoidance

| Saline | 0.1 mg/kg | 0.25 mg/kg | 0.5 mg/kg |
|---|---|---|---|
| 370.0 | 124.0 | 120.0 | 362.0 |
| 518.0 | 366.0 | 205.0 | 886.0 |

Data are expressed as latency to enter the dark side of the apparatus in seconds for each animal (10 animals per treatment group). Data is rank-ordered.

TABLE 5

Summary of the Effects of C105 (0.5 mg/kg) or Saline on Inhibitory Avoidance

| Saline | C105 |
|---|---|
| 21.0 | 21.0 |
| 21.0 | 33.0 |
| 24.0 | 40.0 |
| 26.0 | 41.0 |
| 27.0 | 43.0 |
| 27.0 | 63.0 |
| 33.0 | 65.0 |
| 38.0 | 65.0 |
| 39.0 | 66.0 |
| 39.0 | 79.0 |
| 55.0 | 126.0 |
| 59.0 | 127.0 |
| 59.0 | 137.0 |
| 62.0 | 154.0 |
| 75.0 | 164.0 |
| 79.0 | 167.0 |
| 80.0 | 181.0 |
| 96.0 | 182.0 |
| 100.0 | 188.0 |
| 109.0 | 219.0 |
| 109.0 | 225.0 |
| 113.0 | 225.0 |
| 113.0 | 261.0 |
| 121.0 | 265.0 |
| 121.0 | 357.0 |
| 168.0 | 362.0 |
| 179.0 | 418.0 |
| 179.0 | 444.0 |
| 193.0 | 521.0 |
| 216.0 | 540.0 |
| 235.0 | 556.0 |
| 235.0 | 595.0 |
| 248.0 | 660.0 |
| 370.0 | 880.0 |
| 431.0 | 886.0 |
| 431.0 | 900.0 |
| 518.0 | 900.0 |
| 17.0 | 16.0 |
| 23.0 | 37.0 |
| 27.0 | 38.0 |
| 33.0 | 52.0 |
| 36.0 | 137.0 |
| 40.0 | 170.0 |
| 41.0 | 184.0 |
| 46.0 | 203.0 |
| 47.0 | 209.0 |
| 48.0 | 231.0 |
| 55.0 | 267.0 |
| 55.0 | 273.0 |
| 56.0 | 293.0 |
| 60.0 | 332.0 |
| 74.0 | 426.0 |
| 77.0 | 556.0 |
| 82.0 | 582.0 |
| 92.0 | 698.0 |
| 103.0 | 741.0 |
| 105.0 | 900.0 |
| 107.0 | |
| 108.0 | |
| 114.0 | |
| 116.0 | |
| 120.0 | |
| 120.0 | |
| 129.0 | |
| 154.0 | |
| 176.0 | |
| 204.0 | |
| 218.0 | |
| 225.0 | |
| 240.0 | |
| 281.0 | |
| 334.0 | |
| 518.0 | |
| 680.0 | |
| 900.0 | |
| 900.0 | |
| 900.0 | |

Data are expressed as latency to enter the dark side of the apparatus in seconds for each animal. This table reflects data gathered from all experiments conducted using C105. The numbers of animals in the saline (n = 77) and drug conditions (n = 57) differ because in several experiments, extra control animals were run. Data is rank-ordered.

Data are expressed as latency to enter the dark side of the apparatus in seconds for each animal. This table reflects data gathered from all experiments conducted using C105. The numbers of animals in the saline (n=77) and drug conditions (n=57) differ because in several experiments, extra control animals were run. Data is rank-ordered.

TABLE 6

Effects of Post-Training Administration of C105 on Inhibitory Avoidance

| Saline | C105 |
|---|---|
| 17.0 | 38.0 |
| 25.0 | 65.0 |
| 26.0 | 77.0 |
| 34.0 | 112.0 |
| 36.0 | 123.0 |
| 37.0 | 133.0 |
| 41.0 | 170.0 |
| 64.0 | 185.0 |
| 64.0 | 194.0 |
| 120.0 | 223.0 |
| 137.0 | 276.0 |
| 175.0 | 338.0 |
| 271.0 | 603.0 |
| 349.0 | 824.0 |

Data are expressed as latency to enter the dark side of the apparatus in seconds for each animal (14 animals per treatment group). Data is rank-ordered.

TABLE 7

Effects of C105 on Inhibitory Avoidance in Control and Fornix Lesion Rats

| Control Saline | Fornix Saline | Control 0.5 mg/kg | Fornix 0.5 mg/kg | Control 1.0 mg/kg | Fornix 1.0 mg/kg | Control 2.0 mg/kg | Fornix 2.0 mg/kg | Control 4.0 mg/kg | Fornix 4.0 mg/kg |
|---|---|---|---|---|---|---|---|---|---|
| 50.0 | * | 28.0 | 4.0 | 26.0 | ** | 21.0 | 4.0 | 21.0 | 2.0 |
| 72.0 | ** | 28.0 | 7.0 | 26.0 | 4.0 | 25.0 | 17.0 | 36.0 | 8.0 |
| 92.0 | 2.0 | 93.0 | 13.0 | 48.0 | 7.0 | 41.0 | 18.0 | 64.0 | 13.0 |
| 123.0 | 19.0 | 162.0 | 21.0 | 56.0 | 19.0 | 84.0 | 26.0 | 64.0 | 21.0 |
| 126.0 | 22.0 | 214.0 | 21.0 | 106.0 | 19.0 | 86.0 | 28.0 | 83.0 | 25.0 |
| 164.0 | 23.0 | 240.0 | 32.0 | 195.0 | 166.0 | 92.0 | 30.0 | 83.0 | 28.0 |
| 180.0 | 35.0 | 252.0 | 55.0 | 197.0 | 221.0 | 106.0 | 40.0 | 86.0 | 42.0 |
| 217.0 | 40.0 | 271.0 | 65.0 | 213.0 | 246.0 | 160.0 | 70.0 | 98.0 | 96.0 |
| 222.0 | 72.0 | 284.0 | 72.0 | 238.0 | 274.0 | 192.0 | 84.0 | 193.0 | 140.0 |
| 228.0 | 141.0 | 577.0 | 209.0 | 317.0 | 314.0 | 581.0 | 153.0 | 208.0 | 159.0 |

Data are expressed as latency to enter the dark side of the apparatus in seconds for each animal (10 animals per treatment group). Data is rank-ordered.
* animal died during surgery-no data available
** data from these subjects excluded from analysis as they were outliers: more than two SD's away from the mean

TABLE 8

Effects of C105 on Spontaneous Object Recognition:
Control Data, Discrimination Index D1

| Saline | C105 |
|---|---|
| −1.00 | * |
| −1.00 | 1.00 |
| 0.87 | 5.00 |
| 1.59 | 5.00 |
| 2.00 | 6.00 |
| 2.00 | 6.47 |
| 3.00 | 7.00 |
| 3.00 | 8.00 |
| 3.82 | 8.00 |
| 3.92 | 9.00 |
| 4.00 | 9.00 |
| 4.00 | 9.76 |
| 4.84 | 12.00 |
| 4.97 | 12.06 |
| 5.00 | 12.31 |
| 6.00 | 13.00 |
| 7.00 | 13.00 |
| 7.00 | 13.29 |
| 7.60 | 14.03 |
| 8.00 | 16.00 |
| 9.00 | 16.00 |
| 10.00 | 18.59 |
| 11.00 | 20.00 |
| 18.00 | 20.00 |
| 23.00 | 20.00 |
| 23.00 | 22.00 |
| 32.00 | 26.00 |

*data for one subject in the C105 excluded as it was an outlier—more than two SD's away from the mean.
Data is rank-ordered.

TABLE 9

Effects of C105 on Spontaneous Object Recognition:
Fornix Data, Discrimination Index D1

| Fornix + Saline | Fornix + C105 |
|---|---|
| * | −4.79 |
| ** | −0.12 |
| ** | 0.00 |
| −2.60 | 1.92 |
| −0.60 | 3.00 |
| −0.30 | 3.26 |
| 0.00 | 5.00 |
| 0.00 | 6.00 |
| 1.00 | 6.00 |
| 1.00 | 6.00 |
| 2.90 | 8.00 |
| 3.00 | 9.00 |
| 3.00 | 12.30 |
| 4.00 | 14.80 |
| 7.00 | 16.46 |
| 10.00 | 18.00 |
| 17.00 | 19.29 |

*animal died during surgery: no data collected
**data for these two animals not videotaped
Data is rank-ordered.

TABLE 10

Effects of C105 on Spontaneous Object Recognition:
Control Data, Discrimination Index D2

| Saline | C105 |
|---|---|
| −5.88 | * |
| −3.03 | 4.00 |
| 6.48 | 10.20 |
| 8.69 | 24.32 |
| 8.77 | 25.00 |
| 10.00 | 25.30 |
| 14.29 | 27.14 |
| 17.95 | 30.36 |
| 20.67 | 31.33 |
| 22.09 | 33.52 |
| 22.48 | 36.36 |
| 22.58 | 37.14 |
| 23.08 | 39.37 |
| 23.18 | 41.18 |
| 25.00 | 42.11 |
| 27.27 | 47.06 |
| 30.77 | 47.83 |
| 31.43 | 48.15 |
| 33.33 | 52.94 |
| 35.58 | 55.56 |
| 45.45 | 55.56 |
| 50.00 | 55.61 |
| 51.11 | 57.50 |
| 52.84 | 63.29 |
| 53.49 | 76.47 |

TABLE 10-continued

Effects of C105 on Spontaneous Object Recognition:
Control Data, Discrimination Index D2

| Saline | C105 |
|---|---|
| 56.25 | 83.33 |
| 66.67 | 100.00 |

*data excluded because it was more than 2 SD's away from the mean
Data is rank-ordered.

TABLE 11

Effects of C105 on Spontaneous Object Recognition:
Fornix Data, Discrimination Index D2

| Fornix + Saline | Fornix + C105 |
|---|---|
| * | −26.45 |
| ** | −0.75 |
| ** | 0.00 |
| −14.29 | 9.50 |
| −8.78 | 15.55 |
| −5.23 | 17.64 |
| 0.00 | 22.22 |
| 0.00 | 27.09 |
| 2.84 | 29.41 |
| 7.69 | 30.00 |
| 9.09 | 31.25 |
| 10.59 | 36.00 |
| 20.00 | 37.50 |
| 30.28 | 40.91 |
| 33.33 | 42.86 |
| 48.57 | 55.45 |
| 50.00 | 62.34 |

*animal died during surgery: no data collected
**data for these two animals not videotaped
Data is rank-ordered.

TABLE 12

Effects of C105 on Tail-Flick Analgesia

| Saline | 1.0 mg/kg | 2.0 mg/kg | 4.0 mg/kg | 8.0 mg/kg |
|---|---|---|---|---|
| 1.55 | 1.13 | 2.46 | 2.22 | * |
| 2.19 | 2.28 | 2.68 | 3.13 | 3.13 |
| 2.37 | 3.26 | 2.79 | 5.43 | 4.67 |
| 2.71 | 3.30 | 3.05 | 6.26 | 4.72 |
| 3.44 | 4.59 | 3.56 | 6.42 | 5.22 |
| 3.58 | 4.60 | 3.89 | 6.66 | 6.54 |
| 3.64 | 5.09 | 3.96 | 16.44 | 7.39 |
| 5.34 | 6.01 | 4.45 | 20.00 | 14.43 |

*no data for this subject was collected
Data is rank-ordered.

Equivalents

Those skilled in the art will recognize, or be able to ascertain using no more than routine experimentation, many equivalents to the specific embodiments of the invention described herein. Such equivalents are intended to be encompassed by the following claims.

All patents, publications, and other references cited above are hereby incorporated by reference in their entirety.

We claim:

1. A method of improving memory consolidation in a human, comprising the step of administering an amphetamine to a human having an impairment in memory consolidation in an amount effective to improve memory consolidation in the human, wherein the amphetamine is administered as a component of a composition that includes at least 90 mole percent l-amphetamine relative to the total amphetamine content of the composition.

2. The method of claim 1, wherein the amphetamine is administered in a single dose.

3. The method of claim 2, wherein the single dose is a dose between about 0.0001 mg/kg dose to about 100 mg/kg dose.

4. The method of claim 3, wherein the dose is between 0.5 mg/kg dose to 4 mg/kg dose.

5. The method of claim 2, wherein the single dose is a dose between 2.5 mg dose to 125 mg dose.

6. The method of claim 1, wherein the amphetamine is administered in multiple doses.

7. The method of claim 6, wherein each dose of the multiple doses is administered at a dose between about 0.0001 mg/kg dose to about 100 mg/kg dose.

8. The method of claim 7, wherein the dose is between 0.5 mg/kg dose to 4 mg/kg dose.

9. The method of claim 6, wherein each dose of the multiple doses is administered at a dose between 2.5 mg dose to 125 mg dose.

10. A method of improving memory consolidation in a human, comprising the step of administering an amphetamine to a human having an impairment in memory consolidation in an amount effective to improve memory consolidation in the human, wherein the amphetamine is administered as a component of a composition that includes at least 95 mole percent l-amphetamine relative to the total amphetamine content of the composition.

11. The method of claim 10, wherein the amphetamine is administered in multiple doses.

12. A method of improving memory consolidation in a human, comprising the step of administering an amphetamine to a human having an impairment in memory consolidation in an amount effective to improve memory consolidation in the human, wherein the amphetamine is administered as a component of a composition that includes at least 99 mole percent l-amphetamine relative to the total amphetamine content of the composition.

13. The method of claim 12, wherein the amphetamine is administered in multiple doses.

14. A method of improving memory consolidation in a human, comprising the step of administering an amphetamine to a human having an impairment in memory consolidation in an amount effective to improve memory consolidation in the human, wherein the amphetamine is administered as a component of a composition that includes at least 90 mole percent l-amphetamine relative to the total amphetamine content of the composition and the dose of l-amphetamine administered to the human is from about 0.0001 mg/kg dose to about 100 mg/kg dose.

15. The method of claim 14, wherein the amphetamine is administered in multiple doses.

16. A method of improving memory consolidation in a human, comprising the step of administering an amphetamine to a human having an impairment in memory consolidation in an amount effective to improve memory consolidation in the human, wherein the amphetamine is administered as a component of a composition that includes at least 90 mole percent l-amphetamine relative to the total amphetamine content of the composition and the dose of l-amphetamine administered to the human is from 2.5 mg dose to 125 mg dose.

17. The method of claim 16, wherein the amphetamine is administered in multiple doses.

18. A method of improving memory consolidation in a human, comprising the step of administering an amphetamine to a human having an impairment in memory consolidation in an amount effective to improve memory consolidation in the human, wherein the amphetamine is administered as a component of a composition that includes at least 95 mole percent 1-amphetamine relative to the total amphetamine content of the composition and the dose of 1-amphetamine administered to the human is from about 0.0001 mg/kg dose to about 100 mg/kg dose.

19. The method of claim 18, wherein the amphetamine is administered in multiple doses.

20. A method of improving memory consolidation in a human, comprising the step of administering an amphetamine to a human having an impairment in memory consolidation in an amount effective to improve memory consolidation in the human, wherein the amphetamine is administered as a component of a composition that includes at least 95 mole percent 1-amphetamine relative to the total amphetamine content of the composition and the dose of 1-amphetamine administered to the human is from 2.5 mg dose to 125 mg dose.

21. The method of claim 20, wherein the amphetamine is administered in multiple doses.

22. A method of improving memory consolidation in a human, comprising the step of administering an amphetamine to a human having an impairment in memory consolidation in an amount effective to improve memory consolidation in the human, wherein the amphetamine is administered as a component of a composition that includes at least 99 mole percent 1-amphetamine relative to the total amphetamine content of the composition and the dose of 1-amphetamine administered to the human is from 0.5 mg/kg dose to 4 mg/kg dose.

23. The method of claim 22, wherein the amphetamine is administered in multiple doses.

24. A method of improving memory consolidation in a human, comprising the step of administering an amphetamine to a human having an impairment in memory consolidation in an amount effective to improve memory consolidation in the human, wherein the amphetamine is administered as a component of a composition that includes at least 99 mole percent 1-amphetamine relative to the total amphetamine content of the composition and the dose of 1-amphetamine administered to the human is from between 2.5 mg dose to 125 mg dose.

25. The method of claim 24, wherein the amphetamine is administered in multiple doses.

26. A method of improving memory consolidation in a human, comprising the steps of:

a) assessing the degree of impairment in memory consolidation in a human having an impairment in memory consolidation;

b) administering an amphetamine to the human having an impairment in memory consolidation in an amount effective to improve memory consolidation in the human, wherein the amphetamine is administered as a component of a composition that includes at least 90 mole percent 1-amphetamine relative to the total amphetamine content of the composition; and c) determining the improvement in memory consolidation after administering the amphetamine to the human having an impairment in memory consolidation.

27. The method of claim 26, further including the step of comparing the impairment in memory consolidation in the human before administering the amphetamine to the improvement in memory consolidation in the human after administering the amphetamine.

28. The method of claim 26, wherein the amphetamine is administered in multiple doses.

* * * * *

UNITED STATES PATENT AND TRADEMARK OFFICE
CERTIFICATE OF CORRECTION

PATENT NO.   : 6,828,351 B2
DATED        : December 7, 2004
INVENTOR(S)  : Mel Epstein and Kjesten A. Wiig It is certified that error appears in the above-identified patent and that said Letters Patent is hereby corrected as shown below:

Column 64,
Lines 1, 28, 38, 48, 50, 60 and 62, delete "1-amphetamine" and substitute therefor
-- l-amphetamine --.

Column 65,
Lines 5, 7, 17, 19, 29 and 31, delete "1-amphetamine" and substitute therefor
-- l-amphetamine --.

Column 66,
Lines 5, 7 and 23, delete "1-amphetamine" and substitute therefor -- l-amphetamine --.

Signed and Sealed this

Eighth Day of March, 2005

JON W. DUDAS
*Director of the United States Patent and Trademark Office*